US012807716B2

(12) United States Patent
Zhou et al.

(10) Patent No.: US 12,807,716 B2
(45) Date of Patent: Nov. 24, 2026

(54) CLAUDIN 18.2 ANTIBODY AND USE THEREOF

(71) Applicant: Shanghai Escugen Biotechnology Co., Ltd., Shanghai (CN)

(72) Inventors: Qing Zhou, Shanghai (CN); Chuanying Xu, Shanghai (CN); Weihong Nian, Shanghai (CN); Xiangyu He, Shanghai (CN); Xintong Zheng, Shanghai (CN); Xinmin Zhang, Shanghai (CN); Feng He, Shanghai (CN); Jing Xiao, Shanghai (CN)

(73) Assignee: Shanghai Escugen Biotechnology Co., Ltd., Shanghai (CN)

( * ) Notice: Subject to any disclaimer, the term of this patent is extended or adjusted under 35 U.S.C. 154(b) by 919 days.

(21) Appl. No.: 17/798,873

(22) PCT Filed: Feb. 10, 2021

(86) PCT No.: PCT/CN2021/076482
§ 371 (c)(1),
(2) Date: Aug. 10, 2022

(87) PCT Pub. No.: WO2021/160155
PCT Pub. Date: Aug. 19, 2021

(65) Prior Publication Data

US 2023/0096452 A1 Mar. 30, 2023

(30) Foreign Application Priority Data

Feb. 10, 2020 (CN) ........................ 202010086516.8

(51) Int. Cl.
*C07K 16/28* (2006.01)
*C12N 15/63* (2006.01)

(52) U.S. Cl.
CPC .......... *C07K 16/2839* (2013.01); *C12N 15/63* (2013.01); *C07K 2317/24* (2013.01); *C07K 2317/31* (2013.01); *C07K 2317/565* (2013.01)

(58) Field of Classification Search
CPC .......................... C07K 2317/565; C07K 16/28
USPC ...................................................... 424/133.1
See application file for complete search history.

(56) References Cited

U.S. PATENT DOCUMENTS

| | | | |
|---|---|---|---|
| 9,512,232 | B2 | 12/2016 | Sahin et al. |
| 9,770,487 | B2 | 9/2017 | Sahin et al. |
| 10,314,890 | B2 | 6/2019 | Sahin et al. |
| 2015/0374789 | A1 | 12/2015 | Sahin et al. |
| 2018/0000900 | A1 | 1/2018 | Sahin et al. |
| 2018/0319891 | A1 | 11/2018 | Sahin et al. |
| 2019/0233511 | A1 | 8/2019 | Wang et al. |
| 2019/0298803 | A1 | 10/2019 | Sahin et al. |
| 2020/0040101 | A1 | 2/2020 | Lu et al. |
| 2020/0385463 | A1 | 12/2020 | Li |
| 2020/0399364 | A1 | 12/2020 | Wang et al. |
| 2021/0023177 | A1 | 1/2021 | Sahin et al. |
| 2023/0312704 | A1* | 10/2023 | Zhou ....................... A61P 35/00 424/133.1 |

FOREIGN PATENT DOCUMENTS

| | | | | |
|---|---|---|---|---|
| CA | 3167349 | A1 | * | 8/2021 |
| CN | 104321345 | A | | 1/2015 |
| CN | 110606891 | A | | 12/2019 |
| CN | 109790222 | B | | 3/2022 |
| CN | 119264213 | A | * | 1/2025 |
| EP | 3483182 | A1 | | 5/2019 |
| EP | 3808376 | A1 | | 4/2021 |
| WO | WO 2013167259 | A1 | | 11/2013 |
| WO | WO 2014127785 | A1 | | 8/2014 |
| WO | WO 2019/174617 | A1 | | 9/2019 |
| WO | WO 2019173420 | A1 | | 9/2019 |
| WO | WO 2019219089 | A1 | | 11/2019 |
| WO | WO 2019/242505 | A1 | | 12/2019 |
| WO | WO 2020018852 | A2 | | 1/2020 |

OTHER PUBLICATIONS

PCT International Search Report (with English translation), PCT/CN2021/076482, Apr. 28, 2021, 6 Pages.
Chen, Siyuan, et al., "Advances in the Application of Claudins to Tumor Therapy," Chinese Journal of Biotechnology, Jun. 25, 2019, vol. 35, No. 6, pp. 931-941.
Sahin, U., et al., "Claudin-18 Splice Variant 2 is a Pan-Cancer Target Suitable for Therapeutic Antibody Development," Clinical Cancer Research, Dec. 1, 2008, vol. 14, No. 23, pp. 7624-7634.
Türeci, O., et al., "Characterization of Zolbetuximab in Pancreatic Cancer Models," Oncoimmunology, Nov. 10, 2018, vol. 8, No. 1, Document No. e1523096, pp. 1-10.
Xu, Liange, et al., "Advances of CLDN18.2 Protein in the Therapy of Malignant Tumors," Chinese Journal of Clinical Oncology, Mar. 30, 2019, vol. 46, No. 6, pp. 311-315.
Dottermusch, M. et al. "Expression of the Potential Therapeutic Target Claudin-18.2 is Frequently Decreased in Gastric Cancer: Results from a Large Caucasian Cohort Study." Virchows Archiv, vol. 475, Jul. 22, 2019, pp. 563-571.
European Patent Office, Extended European Search Report, European Patent Application No. 21754619.1, Feb. 23, 2024, 11 pages.
European Patent Office, Extended European Search Report, European Patent Application No. 21753717.4, Feb. 23, 2024, 12 pages.
PCT International Search Report, PCT Application No. PCT/CN2021/076481, May 12, 2021, nine pages.
Singh, P. et al. "Anti-Claudin 18.2 Antibody as New Targeted Therapy for Advanced Gastric Cancer." Journal of Hematology & Oncology, vol. 10, No. 105, May 12, 2017, pp. 1-5.

(Continued)

*Primary Examiner* — Lynn A Bristol
(74) *Attorney, Agent, or Firm* — Fenwick & West LLP

(57) ABSTRACT

The present invention relates to a claudin 18.2 (CLDN18.2) antibody and the use thereof in treating cancers, such as gastric cancer, pancreatic cancer, and esophageal cancer.

20 Claims, 24 Drawing Sheets

Specification includes a Sequence Listing.

(56) References Cited

OTHER PUBLICATIONS

Baxevanis, C. N. "Antibody-Based Cancer Therapy." Expert Opinion on Drug Discovery, vol. 3, No. 4, Mar. 26, 2008, pp. 441-452.
Bendig, M. M. "Humanization of Rodent Monoclonal Antibodies by CDR Grafting." Methods: A Companion to Methods in Enzymology, vol. 8, No. 2, Jan. 1995, pp. 83-93.
European Patent Office, Examination Report, European Patent Application No. 21753717.4, Oct. 29, 2015, 10 pages.
Paul, W. E. "Chapter 9: Structure and Function of Immunoglobulins." Fundamental Immunology, Third Edition, Nov. 1, 1993, pp. 292-295.
United States Office Action, U.S. Appl. No. 17/798,863, filed Oct. 22, 2025, 24 pages.

* cited by examiner

| | h9D1V1 | h9D1V3 | h9D1V4 | h9D1V6 | h9D1V7 | h9D1V9 | Chi-9D1 | 175D10 |
|---|---|---|---|---|---|---|---|---|
| EC50 | 0.4543 | 0.4207 | 0.4698 | 0.3470 | 0.4065 | 0.3822 | 0.3919 | 0.6273 |

| | h9D1V2 | h9D1V5 | h9D1V8 | Chi-9D1 | 175D10 |
|---|---|---|---|---|---|
| EC50 | 0.5254 | 0.4344 | 0.5113 | 0.4049 | 0.8287 |

| | h9D1V1 | h9D1V3 | h9D1V4 | h9D1V6 | h9D1V7 | h9D1V9 | Chi-9D1 | 175D10 |
|---|---|---|---|---|---|---|---|---|
| EC50 | 0.1185 | 0.1145 | 0.1234 | 0.1047 | 0.1223 | 0.1143 | 0.1128 | 0.0 |

| | h9D1V2 | h9D1V5 | h9D1V8 | Chi-9D1 | 175D10 |
|---|---|---|---|---|---|
| EC50 | 0.3475 | 0.6210 | 0.3763 | 0.07667 | ~ 2.547e-005 |

CLAUDIN 18.2 ANTIBODY AND USE THEREOF

FIELD OF THE INVENTION

The present application relates to the technical field of antibodies, as well as to the use and preparation method of the antibody. Specifically, it relates to a claudin 18.2 antibody and use thereof.

BACKGROUND OF THE INVENTION

Claudin is a class of transmembrane proteins with a molecular weight of 20 to 30 kDa. Its family has 24 members and is expressed in many tissues. It is an important molecule for the formation of intercellular tight junctions (TJ) structures. Epithelial cells or endothelial cells form a highly ordered tissue binding through tight-binding molecules (including Claudin molecules) expressed on the cell surface, namely intercellular tight junctions, which control the flow of molecules in the intercellular space of the epithelium. TJ plays a crucial role in maintaining the stable state of epithelial cells or endothelial cells under normal physiological conditions and maintaining cell polarity. Among them, the most striking is Claudin18 (CLDN18), which comprises two splicing variants: CLDN18 splice variant 1 (Claudin18.1, CLDN18.1) and CLDN18 splice variant 2 (Claudin 18.2, CLDN 18.2). Among them, CLDN18.2 (Genbank accession numbers NM_001002026, NP_001002026) is a transmembrane protein with a molecular weight of 27.8 kDa, and both the N- and C-termini of the protein are located intracellularly. The main conformation of the protein contains 4 transmembrane domains (TMD) and 2 extracellular loops (ECL). CLDN18.2 is highly conserved in a variety of mammals, with a full length of 261 amino acids, of which amino acids 1-6 are the N-terminal intracellular domain, amino acids 7-27 are the transmembrane domain 1 (TMD1), and amino acids 28-78 are the extracellular loop 1 (ECL1), the amino acids 79-99 are the transmembrane domain 2 (TMD2), the amino acids 123-144 are the transmembrane domain 3 (TMD3), and the amino acids 100-122 are intracellular domain for connecting TMD2 and TMD3, amino acids 145-167 are the extracellular loop 2 (ECL2), amino acids 168-190 are the transmembrane domain 4 (TMD4), and amino acids 191-261 are the C-terminal intracellular region. There is a canonical N-glycosylation motif on the asparagine at position 116.

CLDN18.1 and CLDN18.2 differed only in the first 26 amino acids of the N-terminal in the N-terminal-transmembrane region 1-extracellular loop 1 of the protein, and the rest of the sequences are the same.

There is considerable evidence that the expression level of CLDN18.2 is significantly activated in tumor cells of stomach, pancreas, esophagus and other tissues, especially in adenocarcinoma subtype tumor cells. In normal tissues, CLDN18.1 is selectively expressed in lung and gastric epithelial cells; CLDN18.2 is only expressed in short-lived gastric glandular epithelial mucosal tissue (differentiated glandular epithelial cells), but not expressed in gastric epithelial stem cells, and differentiated glandular epithelial cells can be continuously replenished by gastric epithelial stem cells. These molecular expression characteristics provide potential for antibody-based treatment of CLDN18.2-related cancers.

SUMMARY OF THE INVENTION

The present application provides a CLDN18.2 antibody for treating cancer, which can effectively treat cancer lesions including gastric cancer, pancreatic cancer or esophageal cancer. Specifically, this application relates to:

1. A CLDN18.2 antibody, comprising heavy chain CDRs and light chain CDRs, wherein the heavy chain CDRs are:

CDR1 comprising the amino acid sequence as shown by SEQ ID NO: 18, CDR2 comprising the amino acid sequence as shown by SEQ ID NO: 19, and CDR3 comprising the amino acid sequence as shown by SEQ ID NO: 20; or CDR1 comprising the amino acid sequence as shown by SEQ ID NO:21, CDR2 comprising the amino acid sequence as shown by SEQ ID NO:22, and CDR3 comprising the amino acid sequence as shown by SEQ ID NO:23;

wherein the light chain CDRs are:

CDR1 comprising the amino acid sequence as shown by SEQ ID NO:24, CDR2 comprising the amino acid sequence as shown by SEQ ID NO:25, and CDR3 comprising the amino acid sequence as shown by SEQ ID NO:26; or CDR1 comprising the amino acid sequence as shown by SEQ ID NO:27, CDR2 comprising the amino acid sequence as shown by SEQ ID NO:28, and CDR3 comprising the amino acid sequence as shown by SEQ ID NO:29.

In some embodiments, the application relates to a CLDN18.2 antibody, comprising an amino acid sequence that is at least 95%, at least 96%, at least 97%, at least 98%, or at least 99% identical to heavy chain CDRs and light chain CDRs selected from any one of the following:

wherein the heavy chain CDRs are:

CDR1 comprising the amino acid sequence as shown by SEQ ID NO: 18, CDR2 comprising the amino acid sequence as shown by SEQ ID NO: 19, and CDR3 comprising the amino acid sequence as shown by SEQ ID NO: 20; or CDR1 comprising the amino acid sequence as shown by SEQ ID NO:21, CDR2 comprising the amino acid sequence as shown by SEQ ID NO:22, and CDR3 comprising the amino acid sequence as shown by SEQ ID NO:23;

wherein the light chain CDRs are:

CDR1 comprising the amino acid sequence as shown by SEQ ID NO:24, CDR2 comprising the amino acid sequence as shown by SEQ ID NO:25, and CDR3 comprising the amino acid sequence as shown by SEQ ID NO:26; or CDR1 comprising the amino acid sequence as shown by SEQ ID NO:27, CDR2 comprising the amino acid sequence as shown by SEQ ID NO:28, and CDR3 comprising the amino acid sequence as shown by SEQ ID NO:29.

In some embodiments, the application relates to a CLDN18.2 antibody comprising a conservatively mutated sequence of the amino acid sequences of heavy chain CDRs and light chain CDRs selected from any one of the following, wherein the heavy chain CDRs are:

CDR1 comprising the amino acid sequence as shown by SEQ ID NO: 18, CDR2 comprising the amino acid sequence as shown by SEQ ID NO: 19, and CDR3 comprising the amino acid sequence as shown by SEQ ID NO: 20; or CDR1 comprising the amino acid sequence as shown by SEQ ID NO:21, CDR2 comprising the amino acid sequence as shown by SEQ ID NO:22, and CDR3 comprising the amino acid sequence as shown by SEQ ID NO:23;

wherein the light chain CDRs are:

CDR1 comprising the amino acid sequence as shown by SEQ ID NO:24, CDR2 comprising the amino acid sequence as shown by SEQ ID NO:25, and CDR3 comprising the amino acid sequence as shown by SEQ ID NO:26; or CDR1 comprising the amino acid sequence as shown by SEQ ID NO:27, CDR2 comprising the amino acid sequence as shown by SEQ ID NO:28, and CDR3 comprising the amino acid sequence as shown by SEQ ID NO:29.

2. The antibody of item 1, comprising a heavy chain variable region as shown by SEQ ID NO:30, SEQ ID NO:31, SEQ ID NO:34, SEQ ID NO:36, or SEQ ID NO:40.

In some embodiments, the application relates to a CLDN18.2 antibody comprising an amino acid sequence that is at least 85%, at least 90%, at least 95%, at least 98%, at least 99% identical to: a heavy chain variable region as shown by SEQ ID NO:30, SEQ ID NO:31, SEQ ID NO:34, SEQ ID NO: 36 or SEQ ID NO:40.

3. The antibody of item 1, comprising a light chain variable region as shown by SEQ ID NO:32, SEQ ID NO: 33, SEQ ID NO:35, SEQ ID NO:37, SEQ ID NO:41 or SEQ ID NO:42.

In some embodiments, the present application relates to a CLDN18.2 antibody comprising an amino acid sequence that is at least 85%, at least 90%, at least 95%, at least 98%, at least 99% identical to: a light chain variable region as shown by SEQ ID NO: 32, SEQ ID NO: 33, SEQ ID NO: 35, SEQ ID NO: 37, SEQ ID NO: 41 or SEQ ID NO: 42.

4. The antibody of any one of items 1-3, comprising a heavy chain variable region and a light chain variable region, wherein:

1) the heavy chain variable region is shown by SEQ ID NO:30 and the light chain variable region is shown by SEQ ID NO:32; or 2) the heavy chain variable region is shown by SEQ ID NO:31 and the light chain variable region is shown by SEQ ID NO:33.

In some embodiments, the application relates to a CLDN18.2 antibody comprising an amino acid sequence that is at least 85%, at least 90%, at least 95%, at least 98%, at least 99% identical to:

1) the heavy chain variable region is shown by SEQ ID NO:30 and the light chain variable region is shown by SEQ ID NO:32; or 2) the heavy chain variable region is shown by SEQ ID NO:31 and the light chain variable region is shown by SEQ ID NO:33.

5. The antibody of any one of items 1-3, comprising a heavy chain variable region and a light chain variable region, wherein:

1) the heavy chain variable region as shown by SEQ ID NO:34 and the light chain variable region as shown by SEQ ID NO:35;

2) the heavy chain variable region as shown by SEQ ID NO:36 and the light chain variable region as shown by SEQ ID NO:35;

3) the heavy chain variable region as shown by SEQ ID NO:36 and the light chain variable region as shown by SEQ ID NO:37;

4) the heavy chain variable region as shown by SEQ ID NO:40 and the light chain variable region as shown by SEQ ID NO:41; or 5) the heavy chain variable region as shown by SEQ ID NO:40 and the light chain variable region as shown by SEQ ID NO:42.

In some embodiments, the application relates to a CLDN18.2 antibody comprising an amino acid sequence that is at least 85%, at least 90%, at least 95%, at least 98%, at least 99% identical to:

1) the heavy chain variable region is shown by SEQ ID NO:34 and the light chain variable region is shown by SEQ ID NO:35;

2) the heavy chain variable region is shown by SEQ ID NO:36 and the light chain variable region is shown by SEQ ID NO:35;

3) the heavy chain variable region is shown by SEQ ID NO:36 and the light chain variable region is shown by SEQ ID NO:37;

4) the heavy chain variable region is shown by SEQ ID NO:40 and the light chain variable region is shown by SEQ ID NO:41; or 5) the heavy chain variable region is shown by SEQ ID NO:40 and the light chain variable region is shown by SEQ ID NO:42.

6. The antibody of any one of items 1-5, which is a chimeric antibody, a humanized antibody, or a fully human antibody.

7. The antibody of any one of items 1-6, which is a full-length antibody.

8. The antibody according to item 7, which is an IgG antibody.

9. The antibody of any one of items 1-6, which is an antibody fragment that binds to CLDN18.2.

10. The antibody of item 9, wherein the antibody fragment is Fab, Fab'-SH, Fv, scFv or $(Fab')_2$.

11. The antibody of any one of items 1-8, which is a multispecific antibody or a bispecific antibody.

12. The antibody of item 11, wherein the multispecific antibody or bispecific antibody comprises a binding domain that binds to a second biomolecule, and the second biomolecule is a cell surface antigen.

13. The antibody of item 12, wherein the cell surface antigen is a tumor antigen.

14. The antibody of item 12, wherein the cell surface antigen is selected from the group consisting of: CD3, CD20, FcRH5, HER2, LYPD1, LY6G6D, PMEL17, LY6E, CD19, CD33, CD22, CD79A, CD79B, EDAR, GFRA1, MRP4, RET, Steap1 and TenB2.

15. An immunoconjugate, comprising a therapeutic agent, a stimulating factor for interferon gene (STING) receptor agonist, a cytokine, a radionuclide or an enzyme linked to the antibody of any one of items 1-10.

16. The conjugate of item 15, wherein the therapeutic agent is a chemotherapeutic drug.

17. The conjugate of item 15, wherein the therapeutic agent is a cytotoxic agent.

18. A fusion protein or polypeptide comprising the antibody or antigen-binding fragment of any one of items 1-10.

19. A pharmaceutical composition comprising the antibody of any one of items 1-14, the immunoconjugate of any one of items 15-17, and the fusion protein or polypeptide of item 18.

20. An isolated nucleic acid comprising a polynucleotide sequence encoding the amino acid sequence of any one of SEQ ID NOs: 18-29.

21. The nucleic acid of item 20, comprising a polynucleotide sequence encoding the amino acid sequence of any one of SEQ ID NOs: 30-33.

22. The nucleic acid of item 21, comprising a polynucleotide sequence encoding the antibody or antigen-binding fragment of any one of items 1-10.

23. A vector comprising the polynucleotide sequence of any one of items 20-22.

24. A host cell, comprising the polynucleotide sequence of any one of items 20-22 or the vector of item 23.

25. A method for preparing the antibody of any one of items 1 to 10, comprising culturing the host cell of item 24 and isolating and obtaining the antibody from the culture.

26. Use of a pharmaceutical composition in the preparation of a medicament for treating cancer, the composition comprising the antibody of any one of items 1-14, the immunoconjugate of any one of items 15-17, the fusion protein or polypeptide of item 18.

27. The use of item 26, wherein the cancer is a digestive system cancer.

28. The use of item 27, wherein the digestive system cancer is selected from any one of the following: a gastric cancer, a pancreatic cancer or an esophageal cancer.

29. A cancer detection reagent comprising the antibody of any one of items 1-10 or antigen-binding fragment thereof.

30. The cancer detection reagent of item 29, wherein the antibody or antigen-binding fragment thereof is chemically labeled.

31. The cancer detection reagent of item 30, wherein the label is an enzymatic label, a fluorescent label, an isotopic label or a chemiluminescent label.

32. A cancer diagnosis kit comprising the cancer detection reagent of any one of Items 29-31.

33. The kit of item 32, wherein the cancer is a gastric cancer, a pancreatic cancer or an esophageal cancer.

34. A method for diagnosing a cancer in a subject, comprising: contacting the antibody of any one of items 1-14, the fusion protein or polypeptide of item 18, or the detection reagent of any one of items 29-31 with a tissue sample derived from the subject.

35. The method of item 34, the tissue sample being a subject body fluid (e.g., blood, urine) and a tissue section (e.g., a tissue biopsy sample).

36. The method of item 34 or 35, wherein the cancer is selected from any one of the following: a gastric cancer, a pancreatic cancer or an esophageal cancer.

37. A method of treating cancer in a subject, comprising administering to the subject a therapeutically effective amount of the antibody of any one of items 1-14, the immunoconjugate of any one of items 15-17, the fusion protein or polypeptide of item 18, or the pharmaceutical composition of item 19.

38. The method of item 37, wherein the cancer is a digestive system cancer.

39. The method of item 38, wherein the digestive system cancer is selected from any one of the following: a gastric cancer, a pancreatic cancer or an esophageal cancer.

DETAIL DESCRIPTION OF THE INVENTION

Figure 1:
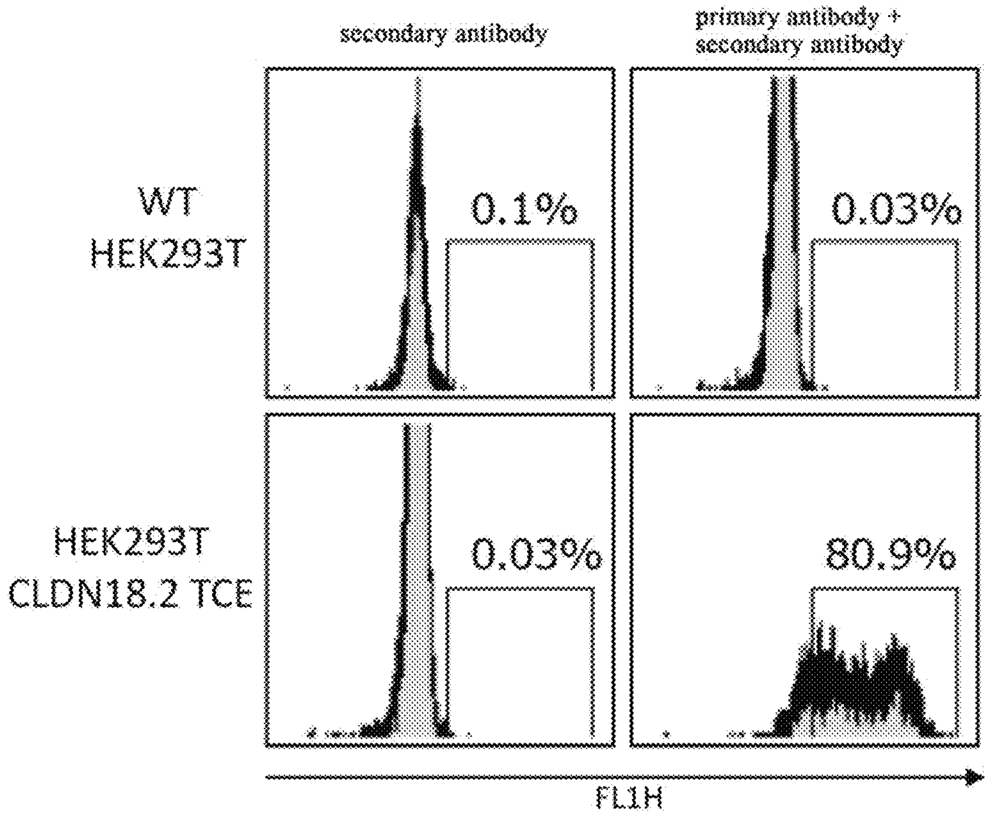
FIG. 1. Human hCLDN18.2-TCE (T-cell epitope peptide) retrovirus expression plasmid was transiently transfected into HEK293-T cells.

Specific examples of the present application will be described in more detail below with reference to the accompanying drawings. While specific examples of the present application are shown by the drawings, it should be understood that the present application may be implemented in various forms and should not be limited by the examples set forth herein. Rather, these examples are provided so that the present application will be more thoroughly understood, and will fully convey the scope of the present application to those skilled in the art.

1. Definition

The term "antibody" is used herein in a broad sense to encompass various antibody structural molecules that bind to CLDN18.2 and comprise one or more of the CDR domains disclosed herein, including but not limited to monoclonal antibodies, polyclonal antibodies, polyclonal specific antibodies (e.g., bispecific antibodies) as well as antibody fragments (e.g., Fv, Fab, Fab', Fab'-SH, $F(ab')_2$), linear antibodies and single chain antibody molecules (e.g., scFv) etc, as long as it exhibits the desired binding activity to CLDN18.2.

Those skilled in the art can fuse one or more CDR domains disclosed in the present application with one or more other polypeptide sequences to prepare functional fusion proteins or polypeptide molecules that bind to CLDN18.2 molecules, such as vaccines, cell membrane receptor antagonists, signaling pathway modulators, and chimeric antigen receptor molecules, etc. For example, one or more CDR domains disclosed in the present application can be used to prepare a CLDN18.2 CAR-T (Chimeric Antigen Receptor T-Cell Immunotherapy) molecule. These fusion protein molecules derived and prepared based on the sequence content disclosed in the present application are also comprised in the protection scope of the present application.

As used herein, the modifier "monoclonal" in the term "monoclonal antibody" means that the antibody is obtained from a substantially homogeneous population of antibodies, containing only trace amounts of naturally occurring mutations or those that occur during the preparation of the monoclonal antibody mutation. In contrast to polyclonal antibody preparations, which typically comprise different antibodies directed against different epitopes, each monoclonal antibody in a monoclonal antibody preparation is directed against a single epitope on an antigen. Monoclonal antibodies of the present application can be made by a variety of techniques including, but not limited to, hybridoma methods, recombinant DNA methods, phage display methods, and methods using transgenic animals containing all or part of the human immunoglobulin loci.

The terms "full-length antibody", "intact antibody" refer to an antibody having a structure substantially similar to that of a native antibody, and the terms are used interchangeably herein.

The "class" of an antibody refers to the type of constant domain or constant region possessed by its heavy chain. There are five major classes of antibodies: IgA, IgD, IgE, IgG, and IgM, and several of these can be further divided into subclasses (isotypes), e.g., IgG1, IgG2, IgG3, IgG4, IgA1, and IgA2. The heavy chain constant domains corresponding to the different classes of immunoglobulins are called a, 8, &, Y, and u, respectively.

A "chimeric antibody" is an antibody having at least a portion of a heavy chain variable region and at least a portion of a light chain variable region derived from one species and at least a portion of the constant region derived from another species. For example, in one embodiment, a chimeric antibody may comprise murine variable regions and human constant regions.

A "humanized" antibody refers to a chimeric antibody comprising amino acid residues from a non-human HVR and amino acid residues from a human FR. In certain embodiments, a humanized antibody will comprise at least one, usually two, substantially the entire variable domain, wherein all or substantially all of the HVRs (e.g., CDRs) correspond to those of the non-human antibody, and all or substantially all FRs correspond to those of a human antibody. Optionally, a humanized antibody may comprise at least a portion of an antibody constant region derived from a human antibody. A "humanized form" of an antibody (e.g., a non-human antibody) refers to an antibody that has undergone humanization.

A "human common framework" is a framework that represents the amino acid residues most frequently found in a selection of human immunoglobulin VL or VH framework sequences. Generally, human immunoglobulin VL or VH sequences are selected from a subgroup of variable domain sequences. Generally, a subgroup of sequences is a subgroup as described in Kabat et al., Sequences of Proteins of Immunological Interest, 5th edition, NIH Publication 91-3242, Bethesda MD (1991), vols. 1-3. In one embodiment, for VH, the subgroup is subgroup III as described in Kabat et al. (supra).

A "human antibody" which may also be referred to as a "human being antibody," "fully human-derived antibody," or "fully human antibody," is an antibody whose amino acid sequence corresponds to that produced by humans or by human cells. This definition of human antibody specifically excludes humanized antibodies comprising non-human antigen-binding residues. Human antibodies can be prepared using a variety of techniques known in the art, comprising phage display library techniques, as described in Hoogenboom and Winter, J. Mol. Biol., 227:381 (1991); Marks et al., J. Mol. Biol., 222:581 (1991). Cole et al., Monoclonal Antibodies and Cancer Therapy, Alan R. Liss, p. 77 (1985); Boerner et al., J. Immunol., 147 (1): 86-95 (1991). Human antibodies can be prepared by administering the antigen to transgenic animals (e.g., immunized xenogeneic mice) that have been modified to produce such antibodies in response to antigenic challenge, but whose endogenous loci have been disabled (for XENOMOUSE™ technology, see, e.g., U.S. Pat. Nos. 6,075,181 and 6,150,584). For human antibodies produced via human B cell hybridoma technology, see also, e.g., Li et al., Proc. Natl. Acad. Sci. USA, 103: 3557-3562 (2006).

The term "hypervariable region" or "HVR" as used herein refers to a region of the variable domain of an antibody having a sequence of hypervariable region (also referred to as "complementarity determining region" or "CDR") and/or forming structurally defined loops ("hypervariable loops") and/or regions containing antigen-contacting residues ("antigen contacts"). In general, an antibody comprises 6 HVRs (CDR regions): 3 in the VH (H1, H2, and H3) and 3 in the VL (L1, L2, and L3). Exemplary HVRs (CDR regions) herein comprise:

(a) the hypervariable loop occurs at amino acid residues 26-32 (L1), 50-52 (L2), 91-96 (L3), 26-32 (H1), 53-55 (H2) and 96-101 (H3) (Chothia and Lesk, J. Mol. Biol. 196:901-917 (1987));

(b) HVRs (CDR regions) occur at amino acid residues 24-34 (L1), 50-56 (L2), 89-97 (L3), 31-35b (H1), 50-65 (H2) and 95-102 (H3) (Kabat et al., Sequences of Proteins of Immunological Interest, 5th Edition, Public Health Service, National Institutes of Health, Bethesda, MD (1991));

(c) antigen contacts occur at amino acid residues 27c-36 (L1), 46-55 (L2), 89-96 (L3), 30-35b (H1), 47-58 (H2) and 93-101 (H3) (MacCallum et al., J. Mol. Biol. 262:732-745 (1996)); and (d) a combination of (a), (b) and/or (c) comprising amino acid residues 46-56 (L2), 47-56 (L2), 48-56 (L2), 49-56 (L2), 26-35 (H1), 26-35b (H1), 49-65 (H2), 93-102 (H3) and 94-102 (H3) of HVR (CDR region).

Unless otherwise indicated, HVR (CDR region) residues and other residues in the variable domain (e.g., FR residues) are numbered herein according to Kabat et al. (supra).

The term "variable region" or "variable domain" refers to the antibody heavy or light chain domain involved in binding an antibody to an antigen. The variable domains of the heavy and light chains (VH and VL, respectively) of native antibodies generally have similar structures, wherein each domain comprises 4 conserved framework regions (FR) and 3 complementarity determining regions (CDR regions). (See, e.g., Kindt et al., Kuby Immunology, 6th ed.) A single VH or VL domain may be sufficient to confer antigen-binding specificity.

An "antibody fragment" refers to a molecule other than an intact antibody that comprises a portion of an intact antibody that binds the antigen to which the intact antibody binds. Examples of antibody fragments include, but are not limited to, Fv, Fab, Fab', Fab'-SH, $F(ab')_2$; diabodies; linear antibodies; single-chain antibody molecules (e.g., scFv); and multispecific antibodies formed from antibody fragments.

The term "cytotoxic agent" as used herein refers to a substance that inhibits or prevents cell function and/or causes cell death or destruction. Cytotoxic agents include, but are not limited to, radioisotopes (e.g., radioisotopes of At211, I131, I125, Y90, Re186, Re188, Sm153, Bi212, P32, Pb212, and Lu); chemotherapeutic agents or drugs (e.g., methotrexate, adriamycin, *vinca* alkaloids (vincristine, vinblastine, etoposide), doxorubicin, melphalan, mitomycin C, chlorambucil, daunorubicin or other insertions); growth inhibitors; enzymes and fragments thereof, such as nucleolytic enzymes; antibiotics; toxins, such as small molecule toxins or enzymatically active toxins of bacterial, fungal, plant or animal origin, comprising fragments and/or variants thereof; various antitumor drugs or anticancer agents known in the art.

An "immunoconjugate" is a conjugate of an antibody with one or more heterologous molecules, including but not limited to cytotoxic agents.

A stimulator of interferon genes (STING) receptor agonist is a molecule that activates STING-dependent signaling pathways to promote the secretion of type I interferon and promote the expression of proteins related to antiviral and antitumor immunity, block viral replication, and promote the immune response to cancer cells. Such molecules are STING agonists of structural classes such as cyclic dinucleotides, aminobenzimidazoles, xanthones and acridinones, benzothiophenes and benzodioxoles.

A "subject" or "individual" is a mammal. Mammals include, but are not limited to, domesticated animals (e.g., cows, sheep, cats, dogs, and horses), primates (e.g., humans and non-human primates, such as monkeys), rabbits, and rodents (e.g., mice and rats). In certain embodiments, the subject or individual is a human.

The term "package insert" is used to refer to instructions typically comprised in commercial packages of therapeutic products that contain information regarding indications, usage, dosage, administration, combination therapy, contraindications and/or warnings regarding the use of such therapeutic products.

"Affinity" refers to the strength of the sum of non-covalent interactions between a single binding site of a molecule (e.g., an antibody) and its binding partner (e.g., an antigen). Unless otherwise indicated, as used herein, "binding affinity" refers to intrinsic binding affinity, which reflects a 1:1 interaction between members of a binding partner (e.g., antibody and antigen). The affinity of a molecule X for its partner Y can generally be represented by the dissociation constant (Kd). Affinity can be measured by common methods known in the art, comprising those described herein. Specific illustrative and exemplary embodiments for measuring binding affinity are described below. "Amino acid sequence homology percentage" with respect to a reference polypeptide sequence is defined as the percentage of amino acid residues in a candidate sequence that are identical with the amino acid residues in the reference polypeptide sequence, after aligning the candidate sequence with the reference polypeptide sequence and introducing gaps if necessary to achieve maximum percent sequence homology and in the event that any conservative substitutions are not considered part of the sequence homology. The determination of amino acid sequence homology percentage can be accomplished in a variety of ways in the art, for example, homology alignment can be performed using software such as BLAST, BLAST-2, ALIGN or Megalign (DNASTAR®). Those skilled in the art can determine suitable parameters for aligning sequences, including any algorithms needed to achieve maximal alignment over the full length of the sequences being aligned.

For example, in the case of amino acid sequence alignment using ALIGN-2, the percentage of an amino acid sequence homology to, with, or relative to a given amino acid sequence B is calculated as follows:

$$100\times\text{fraction } X/Y$$

wherein X is the number of amino acid residues scored as identical matches by the sequence alignment program ALIGN-2 when the program aligns A with B, and wherein Y is the total number of amino acid residues in B. It will be appreciated that where the length of amino acid sequence A is not equal to the length of amino acid sequence B, the percentage of an amino acid sequence homology of A to B will not equal the percentage of an amino acid sequence homology of B to A. Unless otherwise indicated, all percentage values of amino acid sequence homology used herein are obtained using the ALIGN-2 computer program.

2. Antibody, Preparation Method, Composition and Article Thereof

1) Antibody

The present application relates to anti-CLDN18.2 antibodies. In certain embodiments, the present application provides an anti-CLDN18.2 antibody, comprising at least 1, 2, 3, 4, 5 or 6 hypervariable regions (HVRs) or binding domains referred to as complementarity determining regions (CDRs) selected from any of the following: (a) HVR-H1, comprising the amino acid sequence of SEQ ID NO: 18 or SEQ ID NO: 21, or the amino acid sequence with at least 90%, 95%, 96%, 97%, 98%, 99% homology to SEQ ID NO: 18 or SEQ ID NO: 21; (b) HVR-H2, comprising the amino acid sequence of SEQ ID NO: 19 or SEQ ID NO: 22, or the amino acid sequence with at least 90%, 95%, 96%, 97%, 98%, 99% homology to SEQ ID NO: 19 or SEQ ID NO: 22; (c) HVR-H3, comprising the amino acid sequence of SEQ ID NO: 20 or SEQ ID NO: 23, or the amino acid sequence with at least 90%, 95%, 96%, 97%, 98%, 99% homology to SEQ ID NO: 20 or SEQ ID NO: 23; (d) HVR-L1, comprising the amino acid sequence of SEQ ID NO: 24 or SEQ ID NO: 27, or the amino acid sequence with at least 90%, 95%, 96%, 97%, 98%, 99% homology to SEQ ID NO: 24 or SEQ ID NO: 27; (e) HVR-L2, comprising the amino acid sequence of SEQ ID NO: 25 or SEQ ID NO: 28, or the amino acid sequence with at least 90%, 95%, 96%, 97%, 98%, 99% homology to SEQ ID NO: 25 or SEQ ID NO: 28; and (f) HVR-L3, comprising the amino acid sequence of SEQ ID NO: 26 or SEQ ID NO: 29, the amino acid sequences with at least 90%, 95%, 96%, 97%, 98%, 99% homology to SEQ ID NO: 26 or SEQ ID NO: 29. In some cases, the heavy chain variable (VH) domain (region) possessed by the anti-CLDN18.2 antibody may comprise the amino acid sequence with at least 90% sequence homology to SEQ ID NO: 30 or SEQ ID NO: 31 (e.g., at least 91%, 92%, 93%, 94%, 95%, 96%, 97%, 98% or 99% sequence homology) or the amino acid sequence of SEQ ID NO: 30 or SEQ ID NO: 31, and/or the light chain variable (VL) domain (region) possessed by the anti-CLDN18.2 antibody may comprise the amino acid sequence with at least 90% sequence homology to SEQ ID NO: 32 or SEQ ID NO: 33 (e.g., at least 91%, 92%, 93%, 94%, 95%, 96%, 97%, 98% or 99% sequence homology) or the amino acid sequence of SEQ ID NO: 32 or SEQ ID NO: 33.

In some embodiments, the anti-CLDN18.2 antibody comprises a heavy chain variable region and a light chain variable region, wherein the heavy chain variable region comprises the following amino acid sequence:

2) Antibody Fragment

In certain embodiments, the antibodies provided herein are antibody fragments. Antibody fragments include, but are not limited to, Fab, Fab', Fab'-SH, $(Fab')_2$, Fv and scFv fragments and others described below. For a review of certain antibody fragments, see Hudson et al., Nat. Med. 9:129-134 (2003). For scFv fragments, see e.g., WO 93/16185.

Bifunctional antibodies are antibody fragments with two antigen-binding sites, which can be bivalent or bispecific. See e.g., EP 404,097; WO 1993/01161. Trifunctional and tetrafunctional antibodies can be found in, e.g., Hudson et al., Nat. Med. 9:129-134 (2003).

Single domain antibodies are antibody fragments comprising all or part of the heavy chain variable domain or all or part of the light chain variable domain of an antibody. In certain embodiments, the single domain antibody is a human single domain antibody (see, e.g., U.S. Pat. No. 6,248,516 B1). Antibody fragments can be produced by various techniques including, but not limited to, proteolytic digestion of intact antibodies and recombinant host cell (e.g., *E. coli* or phage) production.

3) Chimeric and Humanized Antibodies

In certain embodiments, the antibodies provided herein are chimeric antibodies. The preparation of chimeric antibodies can be found in, e.g., U.S. Pat. No. 4,816,567.

In certain embodiments, the chimeric antibody is a humanized antibody. Typically, non-human antibodies are humanized to reduce immunogenicity to humans while retaining the specificity and affinity of the parental non-human antibody. In general, humanized antibodies comprise one or more variable domains, wherein all HVR (CDR) regions, or portions thereof, are derived from non-human antibodies, and FRs (or portions thereof) are derived from human antibody sequences. Humanized antibodies optionally comprise at least a portion of a human constant region. In some embodiments, some FR residues in a humanized antibody may be replaced with corresponding residues from a non-human antibody to repair or improve the affinity of the antibody.

For humanized antibodies and their production methods, refer to U.S. Pat. Nos. 5,821,337, 7,527,791, 6,982,321 and 7,087,409.

4) Human Antibody

In certain embodiments, the antibodies provided herein are human antibodies. Human antibodies can be produced using various techniques known in the art.

Intact human antibodies or intact antibodies with human variable regions can be prepared by administering an immunogen to a modified transgenic animal, followed by challenge with the antigen. Such animals typically contain all or part of the human immunoglobulin loci that replace the endogenous immunoglobulin loci or are present extrachromosomally or randomly integrated into the animal's chromosomes. In such transgenic mice, the endogenous immunoglobulin loci are generally inactivated. For methods for obtaining human antibodies from transgenic animals, see, e.g., U.S. Pat. Nos. 6,075,181 and 6,150,584 (describing XENOMOUSE™ technology); U.S. Pat. Nos. 5,770,429; 7,041,870 (describing K-M technology); and US Application Publication No. US 2007/0061900. Human variable regions derived from intact antibodies produced by such animals can be further modified, e.g., by combining them with different human constant regions.

Human antibodies can also be made by hybridoma-based methods. Human myeloma and mouse-human hybrid myeloma cell lines have been described for the production of human monoclonal antibodies, see e.g., Boerner et al., J. Immunol., 147:86 (1991). Human antibodies produced via human B cell hybridoma technology are also described in Li et al., Proc. Natl. Acad. Sci. USA, 103:3557-3562 (2006). Other methods comprise, methods described for example, in U.S. Pat. No. 7,189,826 (describing production of monoclonal human IgM antibodies from hybridoma cell lines) and Ni, Xiandai Mianyixue, 26 (4): 265-268 (2006) (describing human-human hybridomas). Human antibodies can also be prepared by isolating Fv clone variable domain sequences selected from phage display libraries of human origin. Such variable domain sequences can then be combined with the desired human constant domains.

Specifically, antibodies of the present application with high affinity can be isolated by screening combinatorial libraries for antibodies with binding activity to CLDN18.2. For example, various methods are known in the art for generating phage display libraries and screening such libraries for antibodies with desired binding characteristics. Such methods can be found, for example, in Hoogenboom et al., Methods in Molecular Biology 178:1-37 (O'Brien et al., eds., Human Press, Totowa, NJ, 2001), Marks and Bradbury, Methods in Molecular Biology 248:161-175 (Edited by Lo, Human Press, Totowa, NJ, 2003) and Lee et al., J. Immunol. Methods 284 (1-2): 119-132 (2004).

In some phage display methods, the VH and VL gene lineages are individually cloned by polymerase chain reaction (PCR) and randomly recombined in a phage library, followed by screening against antigen-binding phage. Phages typically present antibody fragments as single-chain Fv (scFv) fragments or Fab fragments. Patents describing human antibody phage libraries comprise, for example: U.S. Pat. No. 5,750,373 and US Patent Publication No. 2005/0079574, No. 2005/0119455, No. 2005/0266000, No. 2007/0117126, No. 2007/0237764, No. 2007/0292936 and No. 2009/0002360.

Antibodies or antibody fragments isolated from human antibody libraries are considered herein to be human antibodies or human antibody fragments.

5) Multispecific Antibody

In any of the above aspects, the anti-CLDN18.2 antibodies provided herein are multispecific antibodies, e.g., bispecific antibodies. Multispecific antibodies are monoclonal antibodies that have binding specificities for at least two different sites. In certain embodiments, one binding specificity is for CLDN18.2 and the other binding specificity is for any other antigen (e.g., a second biomolecule, e.g., a cell surface antigen, e.g., a tumor antigen). Accordingly, bispecific anti-CLDN18.2 antibodies can have binding specificity for CLDN18.2 and cell surface antigens such as CD3, CD20, FcRH5, HER2, LYPD1, LY6G6D, PMEL17, LY6E, CD19, CD33, CD22, CD79A, CD79B, EDAR, GFRA1, MRP4, RET, Steap1 or TenB2. Bispecific antibodies can be prepared as full-length antibodies or antibody fragments.

Techniques for making multispecific antibodies include, but are not limited to, recombinant co-expression of two immunoglobulin heavy chain-light chain pairs with different specificities, see WO 93/08829, WO2009/08025, and WO 2009/089004A1, etc.

6) Antibody Variants

The antibodies of the present application encompass amino acid sequence variants of the anti-CLDN18.2 antibodies of the present application. For example, antibody variants prepared to further improve the binding affinity and/or other biological properties of the antibody may be desired. Amino acid sequence variants of an antibody can be prepared by introducing appropriate modifications into the nucleotide sequence encoding the antibody. Such modifications comprise, for example, deletions and/or insertions and/or substitutions of residues within the amino acid sequence of the antibody. Any combination of deletions, insertions and substitutions can be made to obtain the final construct, provided that the final construct has the desired characteristics, such as binding properties to the CLDN18.2 antigen.

In certain embodiments, antibody variants with one or more amino acid substitutions are provided. Substitution mutants (including conservative substitution mutants or non-conservative substitution mutants) can be obtained by substitution at one or more sites in the HVR (CDR) region and/or FR region.

Amino acids can be grouped according to common side chain properties:

(1) Hydrophobicity: Norleucine, Met, Ala, Val, Leu, Ile;
(2) Neutral hydrophilicity: Cys, Ser, Thr, Asn, Gln;
(3) Acidic: Asp, Glu;
(4) Alkaline: His, Lys, Arg;
(5) Residues affecting chain orientation: Gly, Pro;
(6) Aromatic: Trp, Tyr, Phe.

Conservative substitutions are defined as substitutions between the same group of amino acids, and non-conservative substitutions are defined as substitutions of amino acids from one of the different classes by amino acids from another class. Antibody variants of the present application can be obtained by introducing amino acid substitutions into the antibodies of the present application and screening the products for the desired activity (e.g., retention/improvement of antigen binding or improvement of ADCC or CDC).

The present application encompasses antibody variants obtained in accordance with the antibodies disclosed herein that contain non-conservative mutations and/or conservative mutations, so long as the variants still possess the desired CLDN18.2 binding activity.

One type of substitutional variant involves antibody variants that substitute one or more hypervariable region residues of a parent antibody (e.g., a humanized or human antibody). In general, the resulting variant selected for further study will be modified (e.g., improved) relative to the parent antibody with respect to certain biological properties (e.g., increased affinity) and/or will substantially retain certain biology nature of the parent antibody. Exemplary substitutional variants are affinity matured antibodies, which can be conveniently produced using, for example, phage display-based affinity maturation techniques such as those described herein. Briefly, one or more HVR (CDR) residues are mutated and the mutated antibody is displayed on phage, and the mutated antibody is screened for a particular biological activity (e.g., binding affinity).

In certain embodiments, substitutions, insertions or deletions may occur within one or more of the HVRs (CDRs), so long as such changes do not substantially impair the ability of the antibody to bind CLDN18.2. For example, conservative changes can be made in the HVR (CDR) that do not substantially reduce binding affinity. For example, such changes may be outside the antigen-contacting residues in the HVR, e.g., conservative or non-conservative amino acid substitutions may occur at one 1, 2, 3, 4, 5 amino acid residues of the FR region.

7) Recombination Method

Anti-CLDN18.2 antibodies of the present application can be prepared using recombinant methods, e.g., as described in U.S. Pat. No. 4,816,567. In one embodiment, an isolated nucleic acid encoding the anti-CLDN18.2 antibody described herein is provided. Such nucleic acids may encode the VL amino acid sequence and/or the VH amino acid sequence of the antibody. In another embodiment, one or more vectors (e.g., expression vectors) comprising such nucleic acids are provided. In another embodiment, host cells comprising such nucleic acids are provided. In one such embodiment, the host cell comprises (e.g., transformed to have): (1) a vector comprising a nucleic acid encoding an amino acid sequence comprising the VL of the antibody and an amino acid sequence comprising the VH of the antibody; or (2) a first vector comprising a nucleic acid encoding an amino acid sequence comprising the VL of the antibody and a second vector comprising a nucleic acid encoding an amino acid sequence comprising the VH of the antibody. In one embodiment, the host cell is a eukaryotic cell, such as a Chinese hamster ovary (CHO) cell or a lymphoid cell (e.g., Y0, NSO, Sp20 cells). In one embodiment, there is provided a method of making an anti-CLDN18.2 antibody, wherein the method comprises culturing a host cell comprising a nucleic acid encoding the antibody as provided above under conditions suitable for expression of the antibody, and optionally recovering the antibody from the host cell (or host cell culture medium).

For recombinant production of anti-CLDN18.2 antibodies, nucleic acid encoding the antibody is isolated (e.g., as described above) and inserted into one or more vectors for further cloning and/or expression in host cells. Such nucleic acids can be readily isolated and sequenced using conventional procedures (e.g., by using oligonucleotide probes capable of binding specifically to the genes encoding the heavy and light chains of the antibody).

Suitable host cells for cloning or expressing antibody-encoding vectors comprise prokaryotic or eukaryotic cells as described herein. For example, antibodies can be produced in bacteria, especially when glycosylation and Fc effector functions are not required. For expression of antibody fragments and polypeptides in bacteria, see, e.g., U.S. Pat. Nos. 5,648,237, 5,789,199, and 5,840,523. Following expression, the antibody in the soluble fraction can be isolated from the bacterial cytoplasm and can be further purified.

In addition to prokaryotes, eukaryotic microorganisms such as filamentous fungi or yeast are also suitable cloning or expression hosts for antibody-encoding vectors, including fungal and yeast strains in which the glycosylation pathway has been "humanized" to produce antibodies with partially or fully human glycosylation patterns. See Li et al., Nat. Biotech. 24:210-215 (2006).

Host cells suitable for expression of glycosylated antibodies can also be derived from multicellular organisms (invertebrates and vertebrates). Examples of invertebrate cells comprise plant and insect cells. A number of baculovirus strains have been identified that can be used for binding to insect cells, especially for transfection of *Spodoptera frugiperda* cells.

Plant cell cultures can also be used as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells can also be used as hosts. For example, mammalian cell lines suitable for growth in suspension may be suitable. Other examples of suitable mammalian host cell lines are SV40-transformed monkey kidney CV1 cell line (COS-7); human embryonic kidney cell line (e.g., 293 cells); baby hamster kidney cells (BHK); mouse Selto Cells (e.g., TM4 cells); monkey kidney cells (CV1); African green monkey kidney cells (VERO-76); human cervical carcinoma cells (HELA); Canine kidney cells (MDCK); Buffalo rat hepatocytes (BRL3A); human lung cells (W138); human hepatocytes (Hep G2); mouse breast tumors (MMT 060562); TRI cells; MRC 5 cells; Chinese hamster ovary (CHO) cells, including DHFR-CHO cells; and myeloma cell lines, such as Y0, NSO and Sp2/0.

8) Immunoconjugate

The present application also provides immunoconjugates comprising the anti-CLDN18.2 antibody herein in combination with one or more cytotoxic agents, such as chemotherapeutic or chemotherapeutic drugs, growth inhibitors, toxins (e.g., protein toxins, enzymatically active toxins of bacterial, fungal, plant or animal origin or fragments thereof) or radioisotopes.

In one embodiment, the immunoconjugate is an antibody-drug conjugate (ADC), wherein the antibody is conjugated to one or more drugs, including but not limited to maytansine, orlistatin, dolastatin, methotrexate, vindesine, taxanes, trichothecene and CC1065.

In another embodiment, the immunoconjugate comprises a conjugate of the anti-CLDN18.2 antibody as described herein with an enzymatically active toxin, or a fragment thereof, including but not limited to diphtheria A chain, non-binding active fragments of diphtheria toxin, exotoxin A chain and trichothecene, etc.

In another embodiment, the immunoconjugate comprises a radioconjugate formed by combining the anti-CLDN18.2 antibody as described herein with a radioactive atom. A variety of radioisotopes are available for the production of radioconjugates. Examples comprise $At^{211}$, $I^{131}$, $I^{125}$, $Y^{90}$, $Re^{186}$, $Re^{188}$, $Sm^{153}$, $Bi^{212}$, $P^{32}$, $Pb^{212}$, and radioisotopes of Lu.

Conjugates of antibodies and cytotoxic agents can be made using a variety of bifunctional protein coupling agents, such as N-succinimidyl-3-(2-pyridyldithio) propionate (SPDP), succinimidyl-4-(N-maleimidomethyl)cyclohexane-1-carboxylate (SMCC), iminothiolane (IT), imidoester bifunctional derivatives (such as dimethyl adipate hydrochloride), active esters (such as disuccinimidyl suberate), aldehydes (such as glutaraldehyde), bisazido compounds (such as bis(p-azidobenzoyl) hexamethylenediamine), double nitrogen derivatives (such as bis(p-diazobenzoyl) ethylenediamine), diisocyanates (such as toluene 2,6-diisocyanate) and double reactive fluorine compounds (such as 1,5-difluoro-2,4-dinitrobenzene).

9) Pharmaceutical Formulation

Pharmaceutical formulations of the anti-CLDN18.2 antibodies of the present application are prepared by mixing the antibody of the desired purity with one or more optional pharmaceutically acceptable carriers in the form of a lyophilized formulation or an aqueous solution. Pharmaceutically acceptable carriers are generally non-toxic to the recipient at the dosages and concentrations employed, and include, but are not limited to: buffers, such as phosphates, citrates, and other organic acids; antioxidants, including ascorbic acid and methylsulfide amino acids; preservatives (such as octadecyldimethylbenzyl ammonium chloride; hexahydrocarbon quaternary ammonium chloride; benzalkonium chloride; benzethonium chloride; phenol, butanol benzyl alcohol; p-hydroxybenzoic acid alkyl esters such as methylparaben or propylparaben; catechol; resorcinol; cyclohexanol; 3-pentanol; and m-cresol); low molecular weight (less than about 10 residues) polypeptides; proteins such as serum albumin, gelatin or immunoglobulins; hydrophilic polymers such as polyvinylpyrrolidone; amino acids such as glycine, glutamic acid, asparagine, histidine, arginine or lysine; monosaccharides, disaccharides and other carbohydrates including glucose, mannose or dextrin; chelating agents such as EDTA; sugars such as sucrose, mannitol, fucose or sorbitol; salt counterions, such as sodium; metal complexes (e.g., zinc-protein complexes); and/or nonionic surfactants, such as polyethylene glycol (PEG).

Exemplary lyophilized antibody formulations are described in U.S. Pat. No. 6,267,958. Aqueous antibody formulations comprise those described in U.S. Pat. No. 6,171,586 and WO2006/044908.

The formulations herein may also contain more than one active ingredient as necessary for the particular indication being treated, preferably active ingredients having complementary activities that do not adversely affect each other. For example, it may be desirable to further provide additional therapeutic agents (e.g., chemotherapeutic agents, cytotoxic agents, growth inhibitors and/or antihormonal agents). Such active ingredients are suitably present in combination in amounts effective for the intended purpose.

10) Article of Manufacture

In another aspect of the present application, an article of manufacture containing the antibody or pharmaceutical composition of the present application is provided. The article of manufacture comprises a container and a label or package insert on or associated with the container. Suitable containers comprise, for example, bottles, vials, syringes, IV solution bags, and the like. Such containers may be formed from various materials, such as glass or plastic. The container holds the composition of the present application alone or in combination with another composition, and may have a sterile access port (e.g., the container may be an intravenous solution bag or a vial with a stopper pierceable by a hypodermic needle). At least one active agent in the composition is the antibody of the present application. The label or package insert indicates that the composition is used to treat the selected tumor. In addition, the article of manufacture may comprise (a) a first container containing a composition therein, wherein the composition comprises the antibody of the present application; and (b) a second container containing a composition therein, wherein the composition comprises another tumor treatment drug or another antibody. The article of manufacture in this embodiment of the present application may further comprise a package insert indicating that such compositions can be used to treat tumors. Alternatively, or in addition, the article of manufacture may further comprise a second (or third) container comprising a pharmaceutically acceptable buffer, such as bacteriostatic water for injection (BWFI), phosphate buffered saline, Ringer's solution and dextrose solution. It may further comprise other materials as may be desirable from a commercial and user standpoint, including other buffers, diluents, filters, needles and syringes.

EXAMPLE

Example 1. Preparation of Immunization and Screening Materials (1) Construction of Human hCLDN18.2-TCE (T Cell Epitope Peptide) Retrovirus Expression Plasmid The hCLDN18.2 cDNA (SEQ ID NO: 1) was cloned and C-terminally fused with a T-cell epitope peptide, resulting in hCLDN18.2-TCE. T-cell epitope peptides can make antigens break through immune tolerance and promote antibody production (Percival-Alwyn J. et al., mAbs, 2015, 7 (1), 129-137). The hCLDN18.2-TCE was cloned into a retroviral vector to obtain the hCLDN18.2-TCE retroviral expression plasmid. The hCLDN18.2-TCE retrovirus expression plasmid was transiently transfected into HEK293-T cells, and the expression of hCLDN18.2 on the surface of HEK293-T cells was analyzed by flow cytometry 72 hours after transfection. The primary antibody (1st Ab) was the self-made positive control (Benchmarker) chimeric antibody 163E12. Cells were first incubated with the primary antibody (1 μg/mL) at 4° C. for 45 minutes, washed with PBS, and then incubated with Alexa Fluor® 488-labeled goat anti-human IgG secondary antibody (ThermoFisher, Cat. No. A-11013) (2nd Ab, diluted 1:200) at 4° C. for 45 minutes. Flow cytometry (FACS) analysis was performed after washing twice with PBS, and the negative control cells were incubated with secondary antibody only. The results were shown in FIG. 1, showing that there was no hCLDN18.2 expression on the surface of wild HEK293-T cells; HEK293-T cells transiently transfected with hCLDN18.2-TCE retrovirus expression plasmid (HEK293T CLDN18.2TCE) had 80.9% of cells with positive expression of hCLDN18.2. This vector plasmid would be used in (1) DNA immunization protocol in Example 2.

(2) Mouse Tumor Cells Expressing High Levels of hCLDN18.2-TCE

Figure 2:
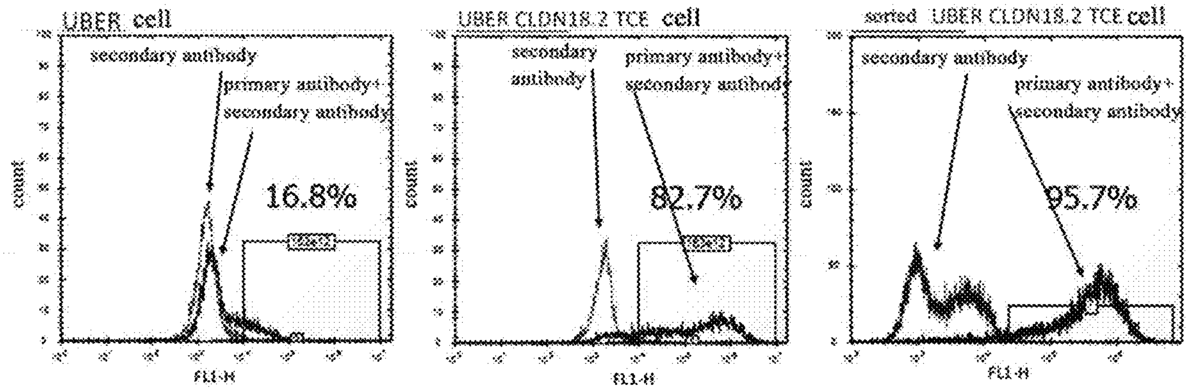
FIG. 2. Mouse tumor cell lines were transfected with hCLDN18.2-TCE lentiviral particles and the mouse tumor cells expressing high levels of hCLDN18.2-TCE were sorted by flow cytometry.

The hCLDN18.2-TCE retrovirus expression plasmid was mixed with the lentiviral packaging plasmid and transfected into 293-T cells to prepare hCLDN18.2-TCE lentiviral particles. The hCLDN18.2-TCE lentiviral particles were transfected into mouse tumor cell lines, and 72 hours later, the pool of mouse tumor cells with high expression of hCLDN18.2 was detected and sorted by flow cytometry. The primary antibody (1st Ab) was the self-made positive control (Benchmarker) chimeric antibody 163E12. Cells were first incubated with primary antibody (1 μg/mL) at 4° C. for 45 minutes, washed with PBS and then incubated with Alexa Fluor® 488-labeled goat anti-human Fc secondary antibody (2nd Ab, 1:200 dilution) at 4° C. for 45 minutes. Flow cytometry (FACS) analysis was performed after washing twice with PBS, and the negative control cells were incubated with secondary antibody only. The results were shown in FIG. 2, indicating that wild-type mouse tumor cells (UBER parental) had only 16.8% positive signals was on the surface; hCLDN18.2-TCE retrovirus-transfected mouse tumor cells (UBER CLDN18.2 TCE) had 82.7% positive cells. After sorting by flow cytometry analysis, up to 95.7% of mouse tumor cells had high levels of hCLDN18.2-TCE expression. The mouse tumor cells of hCLDN18.2-TCE would be used in (2) cellular immunization protocol in Example 2.

(3) Preparation of hCLDN18.2 Extracellular Loop Class 1 Virus Particles

According to the method published by Thorsten K. (Thorsten K., et al, Cancer Res, 2011, 71 (2), 515-527), inserting the Extra Cellular Loop1 (ECL1) (SEQ ID NO: 2) of hCLDN18.2 to the major immunodominant region (MIR) of Hepatitis B virus core antigen (HBcAg) and the G4SG4 linker were introduced at the N-terminal and C-terminal of ECL1 respectively, and a 6×His tag (SEQ ID NO: 3) was added to the C-terminal of the full-length fusion protein. The full-length gene of the fusion protein was synthesized, cloned into pET24a (+) plasmid, and transfected into BL21 (DE3) *E. coli* expression system for fusion protein expression. After purification of the fusion protein, virus-like particles of HBV hCLDN18.2 extracellular loop 1 were prepared in renaturation buffer. The preparation of this virus-like particles of HBV hCLDN18.2 extracellular loop 1 would be used in the (3) virus-like particle multiple-point repeat immunization-cellular immunization protocol and (4) virus-like particle tarsus joint immunization-cell immunization protocol in Example 2.

(4) Construction of CLDN18 Stably Transfected Cell Line

Figure 3:
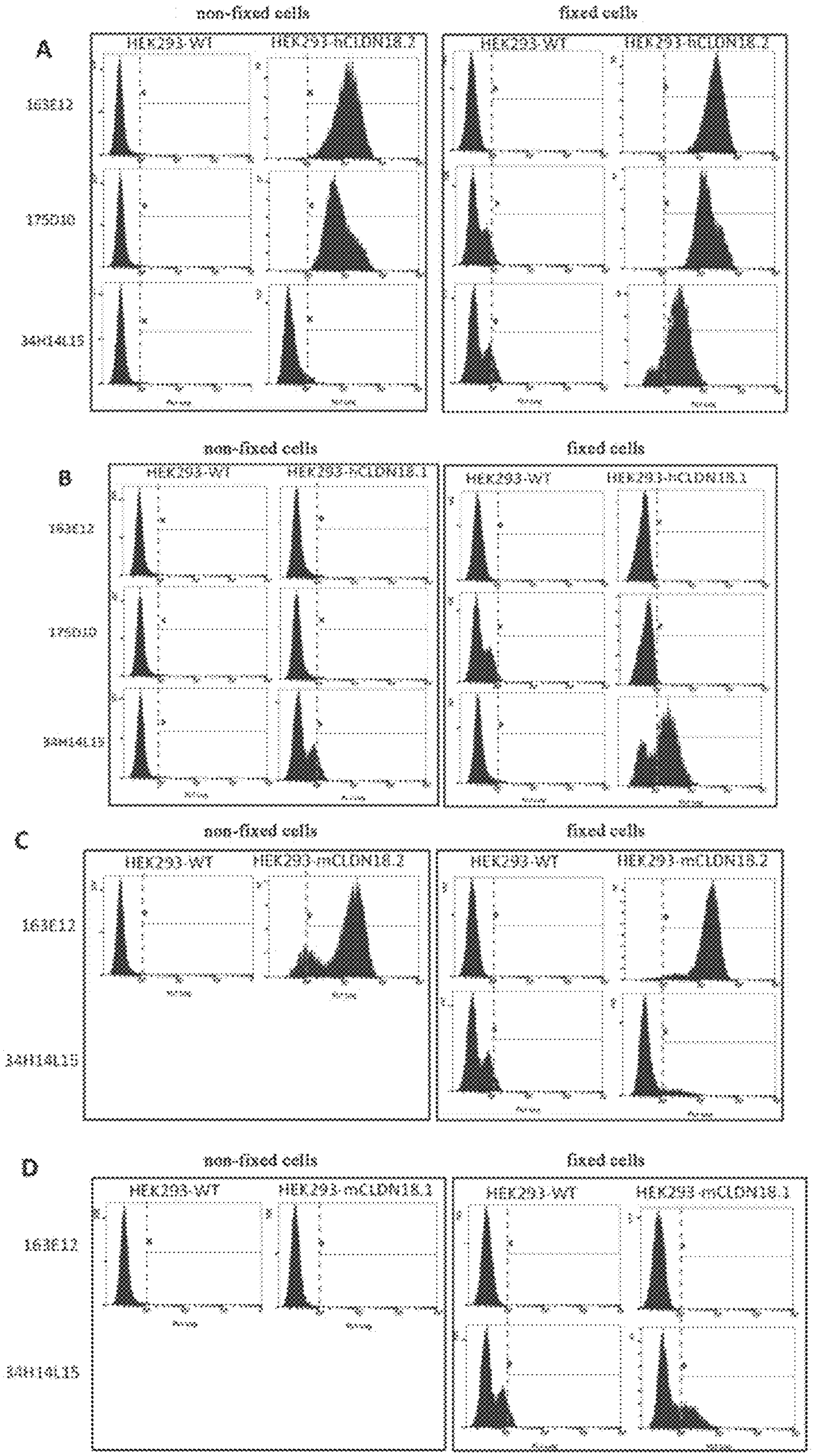
FIG. 3. Flow cytometric analysis of hCLDN18.2, hCLDN18.1 and mCLDN18.2, mCLDN18.1 stably transfected cell lines.

The full-length genes of hCLDN18.2 (SEQ ID NO: 4), hCLDN18.1 (SEQ ID NO: 5), mouse m hCLDN18.2 (SEQ ID NO: 6), and mCLDN18.1 (SEQ ID NO: 7) were synthesized respectively, and cloned into pcDNA3.4 vector plasmid respectively. Plasmids were transfected into HEK293 cells and neomycin (G418) was added for pressure selection. The HEK293 stably transfected cell lines with high expression of hCLDN18.2, hCLDN18.1, m hCLDN18.2 and mCLDN18.1 were selected by limiting dilution method. The results of flow cytometry showed that the HEK293 stably transfected cell lines transfected with hCLDN18.2 and mCLDN18.2 (HEK293-hCLDN18.2, HEK293-mCLDN18.2), both paraformaldehyde-fixed and non-fixed cells could be specifically recognized by self-made anti-CLDN18.2 positive control antibody 163E12 or 175D10 (FIG. 3. A, C), and could be recognized by a commercial broad anti-CLDN18 antibody (34H14L15, Abcam Cat. No. ab203563) (FIG. 3. A, C). HEK293 stably transfected cell lines transfected with hCLDN18.1 and mCLDN18.1 (HEK293-hCLDN18.1, HEK293-mCLDN18.1), paraformaldehyde-fixed and non-fixed cells could not be specifically recognized by the self-made anti-CLDN18.2 positive control antibody 163E12 or 175D10 (FIG. 3. B, D), but could be recognized by a commercial broad anti-CLDN18 antibody (34H14L15) (FIG. 3. B, D). The HEK293 stable transfection described above would be used for hybridoma screening in Example 3.

(5) Preparation of Positive Control Antibodies 43A11, 175D10 and 163E12

Figure 4:
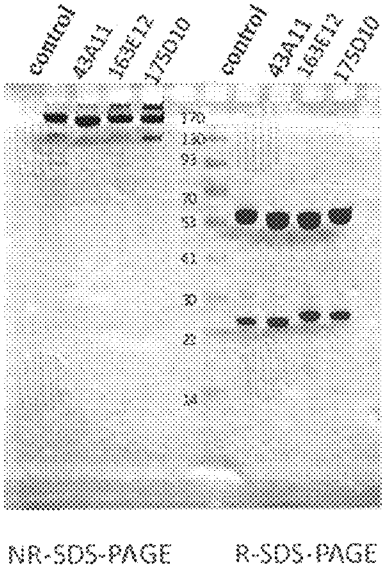
FIG. 4. SDS-PAGE detection of positive control antibodies 43A11, 175D10 and 163E12.

Human-mouse chimeric positive control antibodies 43All heavy chain (SEQ ID NO:8) and light chain (SEQ ID NO:9), 175D10 heavy chain (SEQ ID NO:10) and light chain (SEQ ID NO:11) and 163E12 heavy chain (SEQ ID NO: 12) and light chain (SEQ ID NO: 13) antibody gene full-length were synthesized, respectively, and respectively added a signal peptide at the N-terminus, and then cloned into pcDNA3.4 eukaryotic expression vector. The 43A11, 175D10 and 163E12 heavy chain and light chain expression plasmids were mixed and co-transfected into CHOS cells for transient protein expression, and the supernatant was collected for affinity purification with Protien A and SDS-PAGE detection. The results were shown in FIG. 4.

Example 2. Mouse Immunization Program and Hybridoma Preparation

A total of 4 immunization protocols were used (Table 1), and at least two different strains of mice were used for each immunization protocol (Table 2). In each immunization protocol, some individual mice show higher levels of serum immune titers. Mice individuals with high levels of immune titers in each immunization protocol were sacrificed and their spleens were removed. B lymphocytes were isolated and mixed, and then electrofused with mouse myeloma cell lines to prepare hybridomas. A total of three batches of hybridoma preparation were performed (Table 2).

TABLE 1

| number | Immunization protocol | Immunization material | Mouse strain and number | Immunological methods and detection of immune titers |
|---|---|---|---|---|
| 1 | DNA Immunization protocol | CLDN18.2-TCE viral expression vector | NZB/W(M1, M2) BALB/c(M3, M4) | Preliminary immunization was performed using (Zhang GF, et al. Human Gene Ther. 1999, 10, 1735-1737; Liu F, et al. Gene Ther. 1999, 6, 1258-1266) tail vein high pressure injection of CLDN18.2-TCE virus expression plasmid method was, and three weeks after immunization, flow cytometry was performed to detect the immune titer of mouse serum, and the mice with serum reaction were boosted by HEK293 cells expressing high levels of human CLDN18.2 (Sotoshi N, et al. al. J Immunol Method, 2003, 280, 59-72), one week after boosting immunization, the immune titer of mouse serum was detected by flow cytometry, and the mice with high immune titer were selected to be sacrificed and spleen B cells were fused to prepare hybridomas. |
| 2 | Cellular immunization protocol | Mouse tumor cell line expressing high levels of CLDN18.2-TCE | NZB/W(M1, M2, M3, M4) BALB/c(M1, M2, M3, M4) | Mice were subcutaneously inoculated with mouse tumor cell lines expressing high levels of CLDN18.2-TCE, and the immune titer of mouse serum was detected by flow cytometry in the second and fourth weeks. Serum-reactive mice with insignificant tumor growth were boosted at the fifth week with a mouse tumor cell line of CLDN18.2-TCE (Sotoshi N, et al. J Immunol Method, 2003, 280, 59-72). And three days after boosting immunization, mice with high immune titers were selected to be sacrificed and spleen B cells were fused to prepare hybridomas. |
| 3 | Virus-like particle multiple-point repeat immunization-cellular immunization protocol | Virus-like particles fused to express extracellular loop 1 of CLDN18.2 | NZB/W(M1, M2) B6; 129(M3, M4) | Virus-like particles fused to express extracellular loop 1 of CLDN18.2 were preliminarily immunized by the multiple-point repeat immunization method (Edward AG, Antibodies: A laboratory manual (Second Edition), 2012, Chapter 6, Protocol 30), and one week later, the immune titer of mouse serum against virus-like particles was detected by the ELISA method. The mice with high immune titer were selected for further immunization with the mouse tumor cell line of CLDN18.2-TCE, and the immune titer of the mouse serum was detected by flow cytometry at the fourth week after cell immunization. |

TABLE 1-continued

| number | Immunization protocol | Immunization material | Mouse strain and number | Immunological methods and detection of immune titers |
|---|---|---|---|---|
| | | | | Serum-reactive mice were boosted with cells (Sotoshi N, et al. J Immunol Method, 2003, 280, 59-72), and three days later, the mice were sacrificed and spleen B cells were fused to prepare hybridomas. |
| 4 | Virus-like particle tarsus joint immunization-cellular immunization protocol | Virus-like particles fused to express extracellular loop 1 of CLDN18.2 | NZB/W(M1, M2) B6; 129(M3, M4) SJL(M5, M6, M7) BALB/c(M8, M9, M10, M11) | Virus-like particles fused to express extracellular loop 1 of CLDN18.2 were preliminarily immunized by the mouse tarsus joint immunization method (Edward AG, Antibodies: A laboratory manual (Second Edition), 2012, Chapter 6, Protocol 18), followed by one week later, the immune titer of mouse serum against virus-like particles was detected by the ELISA method. The mice with high immune titer were selected for further immunization with the mouse tumor cell line of CLDN18.2-TCE, and the immune titer of the mouse serum was detected by flow cytometry at the fourth week after cell immunization. Serum-reactive mice were boosted with cells (Sotoshi N, et al. J Immunol Method, 2003, 280, 59-72), and three days later, the mice were sacrificed and spleen B cells were fused to prepare hybridomas. |

TABLE 2

| Mouse Hybridoma Preparation Batch | batch 1 | batch 2 | batch 3 |
|---|---|---|---|
| High-level immune titer mouse source | DNA Immunization protocol: BALB/c mouse M3, M4 | Virus-like particle multiple-point repeat immunization-cellular immunization protocol: NZB/W mice M1, M2, B6; 129 mice M3; Virus-like particle tarsus joint immunization-cellular immunization protocol: B6; 129 mouse M4, SJL mouse M6, BALB/c mouse M9 | Cellular immunization protocol: NZB/W mouse M3; Virus-like particle multiple-point repeat immunization-cellular immunization program: B6; 129 mouse M4; Virus-like particle tarsus joint immunization-cellular immunization protocol: B6; 129 mouse M3 |

Example 3. Hybridoma Screening

The hybridomas from three batches were cloned and cultured by the limiting dilution method, and the cloned supernatant was taken for three rounds of binding or reverse binding screening, antibody typing and antibody-dependent cytotoxicity assay by flow cytometry. A hybridoma clone that could specifically and strongly bound to CLDN18.2 but not or weakly bound to CLDN18.1, and had antibody-dependent cell-mediated cytotoxicity (ADCC) function were selected. The screening steps and the hybridoma clones obtained by screening at each stage were summarized in Table 3.

TABLE 3

| | Mouse Hybridoma Batch | | |
|---|---|---|---|
| | batch 1 | batch 2 | batch 3 |
| Cloning by the limiting dilution method | Ten 384-well plates (plates 1-10), 0.8 cells/well | Ten 384-well plates (plate 11-20), 4.8 cells/well (plate 11-15) and 3.4 cells/well (plate 16-20) | 10 of 384-well plates (Plate 21-30), 1.3 cells/well |
| After 2 weeks of culture, the supernatant was taken from the 384-well plate for primary screening | | | |
| Primary screening | 341 positive clones (amplify, cryopreserve, and save saturated supernatant), MFI > 100,000 | 336 positive clones, MFI > 75,000 (plate 11-15), MFI > 80,000 (plate 16-20) | 89 positive clones, MFI > 90,000 |
| Confirmation Screening | 165 positive clones, HEK293-hCLDN18.2 MFI > 200,000 and HEK293-hCLDN18.1 MFI < 100,000. (Amplify, cryopreserve, and save saturated supernatant) | 120 positive clones, HEK293-hCLDN18.2 MFI > 50,000 and HEK293-hCLDN18.1 MFI < 40,000. (Amplify, freeze, and save saturated supernatant) | 21 positive clones, HEK293-hCLDN18.2 MFI > 70,000 and HEK293-hCLDN18.1 MFI < 30,000. (Amplify, freeze, and save saturated supernatant) |
| Verification Screening | The supernatants of 306 positive clones derived from three confirmation screenings were subjected to validation screening in 5 engineered cell lines (HEK293-hCLDN18.2 cells, HEK293-hCLDN18.1 cells, HEK293-mCLDN18.2 cells, HEK293-mCLDN18.1 cells and HEK293 wild-type cells) | | |
| Antibody typing | Antibody subtyping was performed on the supernatants of 306 positive clones derived from three confirmation screenings | | |
| Antibody-dependent cytotoxicity assay | Based on the results of the aforementioned experimental methods, the saturated supernatants of 128 positive clones were selected for antibody-dependent cytotoxicity detection. | | |
| Based on the results of the aforementioned experimental methods, the first 20 positive clones (18 clones belong to mouse IgG2a or IgG2b or IgG3, 2 clones belong to mouse IgG1) were screened for subcloning and sequencing | | | |

1) Primary screening: Flow cytometry was used to analyze the binding of the supernatant expression product of each clone to a mouse tumor cell line expressing high levels of CLDN18.2-TCE (UBER CLDN18.2 TCE). The fused hybridomas were inoculated into 384-well plates by the limiting dilution method, and the supernatant was collected after ten days of culture to screen positive hybridoma clones by flow cytometry. After co-incubating the supernatant with UBER CLDN18.2 TCE cells (20,000 cells/well) at 4° C. for 45 minutes, the plate was washed and flown with Alexa Fluor®-488-goat anti-mouse IgG (ThermoFisher Cat. No. A28175) as the secondary antibody for cytometry detection, clones with an average fluorescence intensity above 100,000 were screened for amplification, and saturated supernatants were collected for confirmation screening.

3 Batches of hybridomas were cloned by limiting dilution in 10 of 384-well plates per batch. After primary screening, 341 (MFI>100,000), 336 (MFI>75,000 or MFI>80,000) and 89 (MFI>90,000) hybridoma clones that positively bound to the mouse tumor cell line of CLDN18.2-TCE were obtained from three batches of hybridomas.

2) Confirmation screening: the supernatant expression products of the primary screened positive clones in the previous step were incubated with HEK293-hCLDN18.2 cells, HEK293-hCLDN18.1 cells and HEK293 wild-type cells respectively (20,000 cells/well, 4° C., 45 minutes), Alexa Fluor®-488-goat anti-mouse IgG (ThermoFisher, Cat. No. A28175) was used as the secondary antibody to screen for clones positive binding to HEK293-hCLDN18.2 cells, but negative binding to HEK293-hCLDN18.1 cells and HEK293 wild type cells by flow cytometry for amplification, were and saturated supernatants were collected for validation screening.

Figure 5:
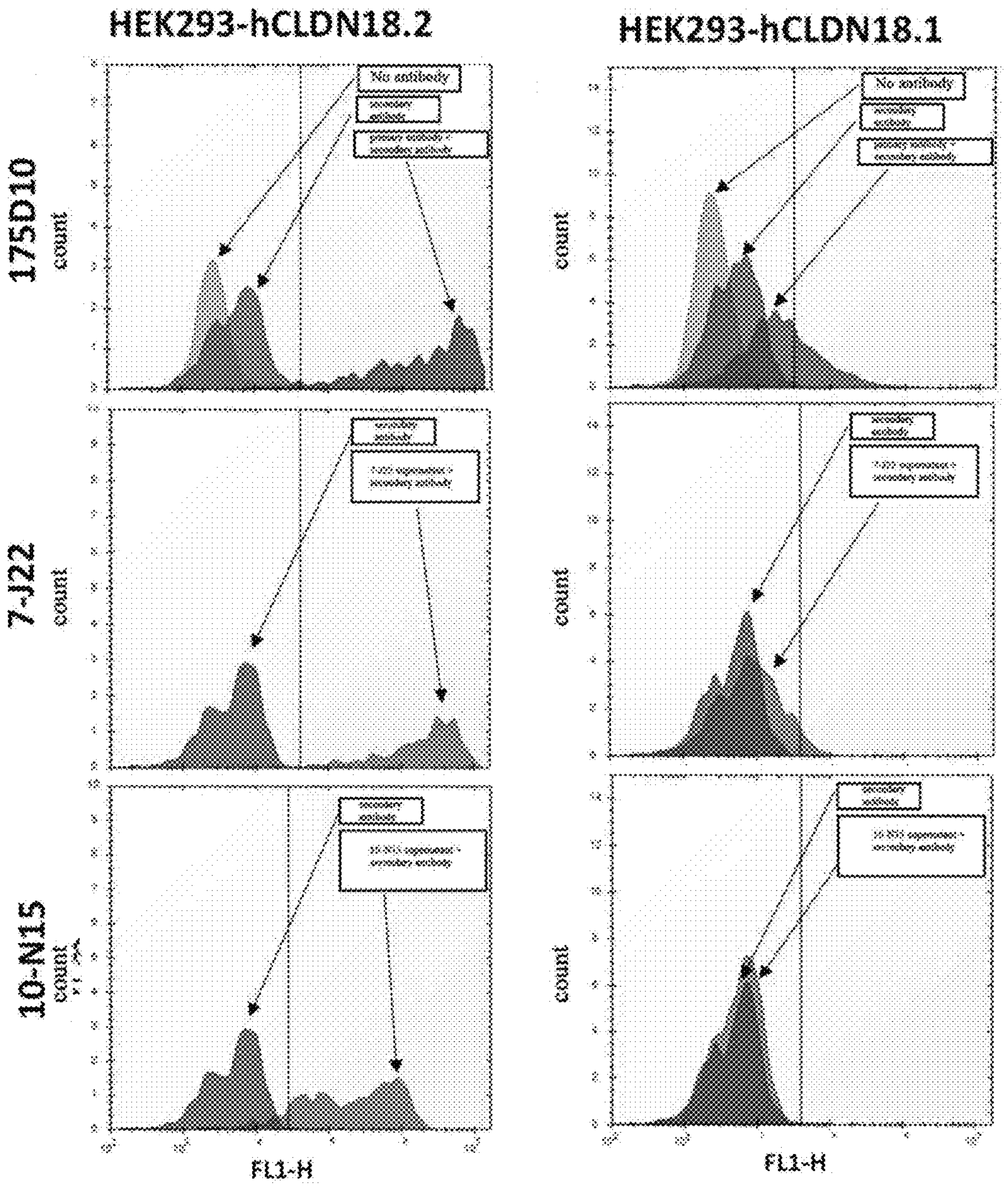
FIG. 5. The binding of positive hybridoma-positive clones in the confirmation screening to HEK293-hCLDN18.2 cells and HEK293-hCLDN18.1 cells.

After confirmation screening, three batches of hybridomas obtain 165 (HEK293-hCLDN18.2 MFI>200,000, HEK293-hCLDN18.1 MFI<100,000), 120 (HEK293-hCLDN18.2 MFI>50,000, HEK293-hCLDN18.1 MFI<40,000) and 21 (HEK293-hCLDN18.2 MFI>70,000, HEK293-hCLDN18.1 MFI<30,000) clones that could specifically and strongly bound to HEK293-hCLDN18.2 cells, but weakly bound to HEK293-hCLDN18.1 cells, and did not bind to HEK293 wild-type cells. FACS analysis of some positive clones was shown in FIG. 5.

Figure 6:
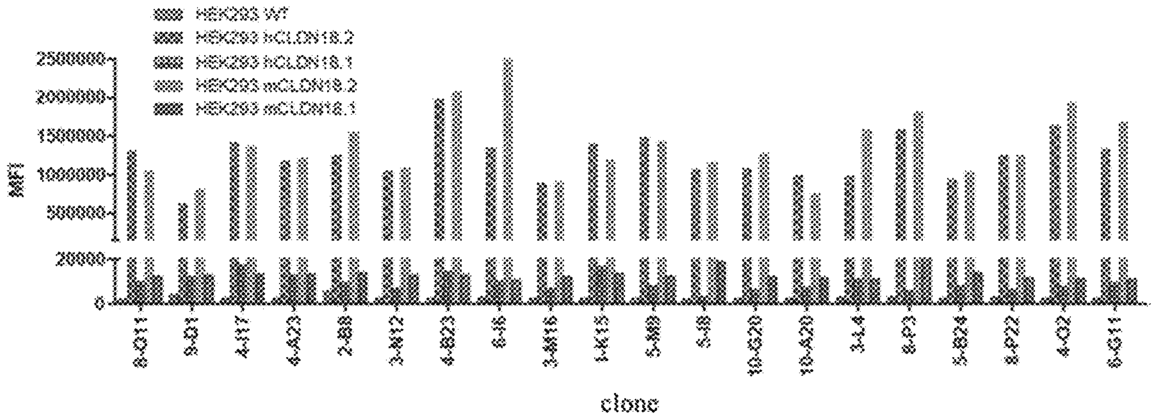
FIG. 6. The flow cytometry analysis of some positive hybridoma clones in the verification screening on 5 cell lines.

3) Verification screening: The supernatant expression products of 306 (165+120+21) positive hybridomas obtained in the confirmation screening of three batches of hybridomas were incubated with HEK293-hCLDN18.2 cells and HEK293-hCLDN18.1 cells, HEK293-mCLDN18.2 cells, HEK293-mCLDN18.1 cells, and HEK293 wild-type cells were (20,000 cells/well, 4° C., 45 minutes), and Alexa Fluor®-488-goat anti-mouse IgG (ThermoFisher, Cat. No. A28175) was used as a secondary antibody for analysis by flow cytometry. The flow cytometry analysis results of some clones on the 5 cell lines were shown in FIG. 6, showing that the mean fluorescence intensity (MFI) of positive clones in HEK293-hCLDN18.2 cells and HEK293-mCLDN18.2 cells exceeded 500,000, while the mean fluorescence intensity in HEK293-hCLDN18.1 cells, HEK293-mCLDN18.1 cells and HEK293 wild-type cell lines were all lower than 20,000, and the mean fluorescence intensity (MFI) of most clones (16/20) in HEK293-hCLDN18.2 cells and HEK293-mCLDN18.2 cells was more than 50 times higher than that in HEK293-hCLDN18.1 cells and HEK293-mCLDN18.1 cells.

4) Antibody typing: Because different subtypes of IgG molecules also had different abilities to mediate ADCC effects. Supernatant antibody expression products of 306 (165+120+21) positive hybridomas obtained in the confirmation screening of three batches of hybridomas were subjected to mouse antibody subtyping using a mouse antibody subtype detection kit before the antibody-dependent cell killing assay were. Most of the subtypes of the 306 clones belonged to mouse IgG2a, IgG2b or IgG3 with ADCC function, and only a few (26/306) were IgG1 subtypes without ADCC function (corresponding to human antibody IgG4 subtype). Some clones were mixed subtypes, possibly because the hybridoma clones were not monoclonal. The light chains were all mouse k subtypes.

5) ADCC Effect Assay

Figure 7:
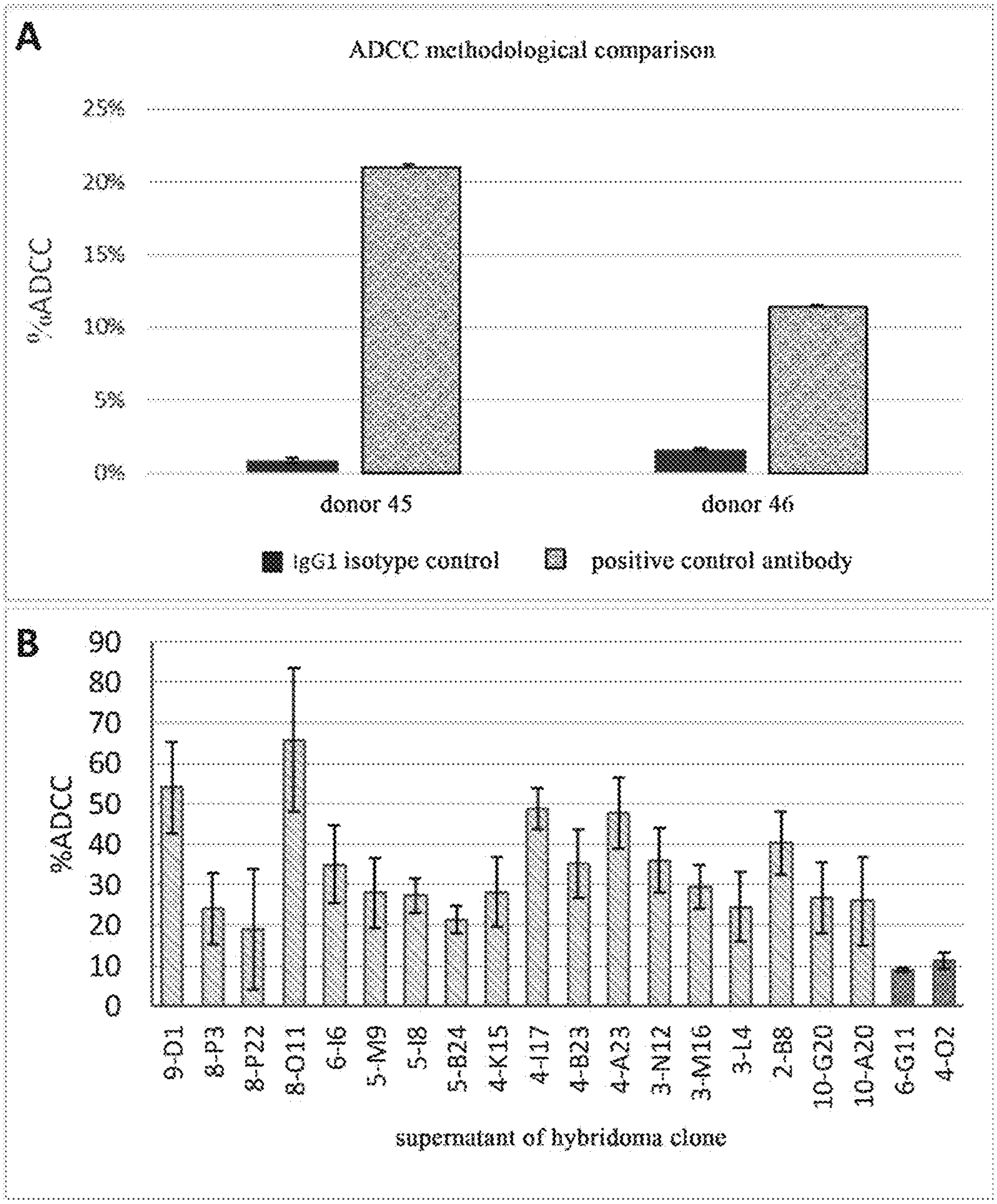
FIG. 7. ADCC effect of supernatant of some positive hybridoma clones.

Taking into account the results of the aforementioned confirmation screening, verification screening and antibody typing, the saturated supernatants of 128 positive clones were selected for antibody-dependent cytotoxicity function detection. The effector cells were human peripheral blood mononuclear cells (PBMCs), which were derived from two donors (NOs. 45 and 46). Blood was drawn from the donors the day before the experiment. The collected blood was stored at room temperature, and the PBMCs were freshly isolated through a Ficoll gradient. The target cells were HEK293 cells expressing CLDN18.2 (HEK293-hCLDN18.2). The hybridoma expression products were uniformly diluted 4-fold. Freshly obtained PBMCs cells and target cells were incubated with each sample for 4 hours at an effect-to-target ratio of 25:1. Antibody ADCC effects were characterized by measuring lactate dehydrogenase (LDH) associated with cytotoxicity. The absorbance value detected when the target cells were lysed spontaneously was defined as 0%, and the absorbance value detected when the target cells were completely lysed was defined as 100%, and the ADCC effect was characterized by the relative percentage activity of each test sample. The ADCC effect results of some clones were shown in FIG. 7. The ADCC killing effect of the clones was higher than 20% on average, and the ADCC effect of some clones (9D-1, 8-011) was higher than 50%. For mouse IgG1 subtypes 6-G11 and 4-02, the ADCC effect was less than 10%.

Figure 8:
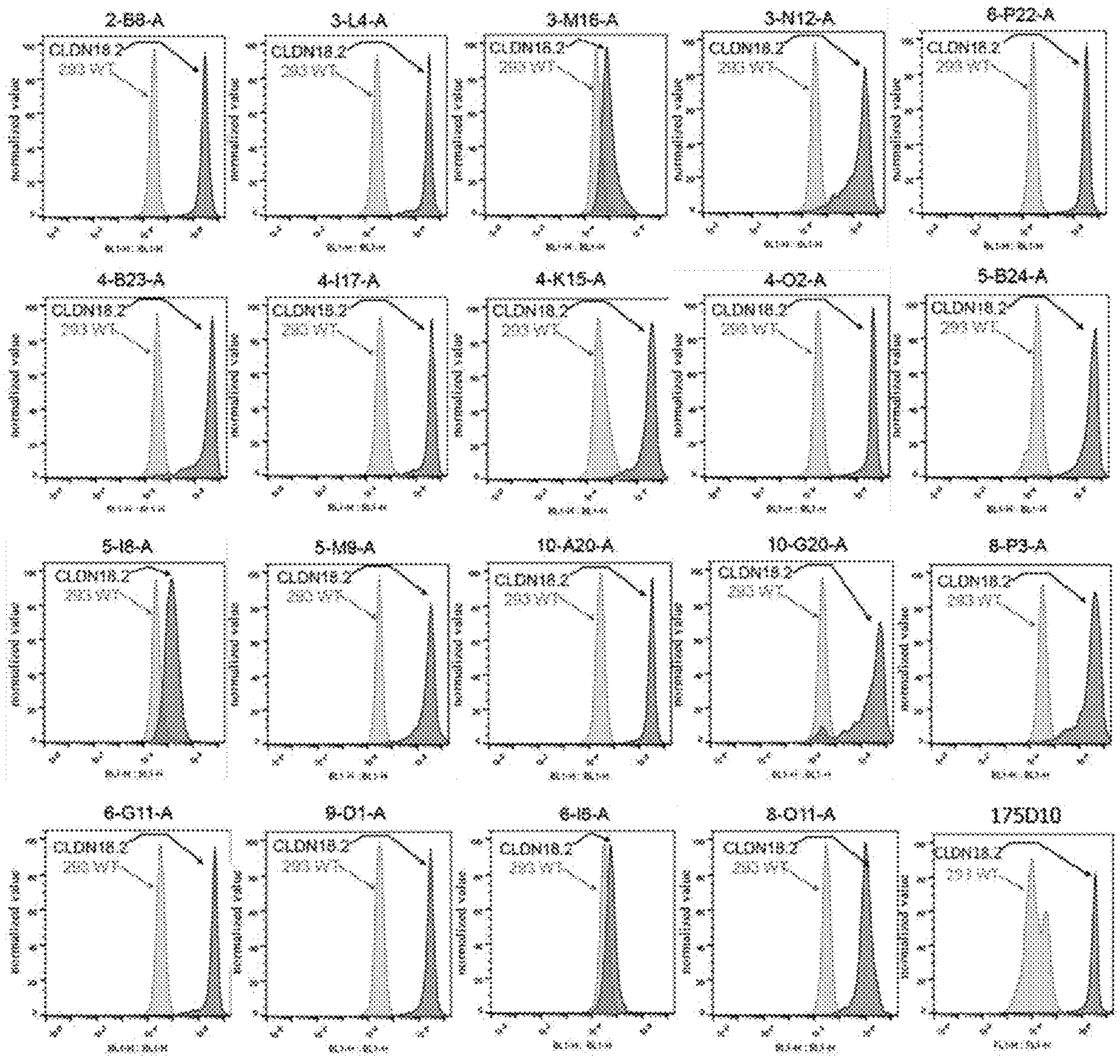
FIG. 8. Flow cytometry analysis of HEK293-hCLDN18.2 cells by hybridoma monoclonal supernatant.

Example 4. Subcloning of Positive Hybridoma Clones and Sequencing of Antibody Molecular Sequences The cryopreserved positive hybridoma clones were recovered and subcloned. Each positive hybridoma clone was subcloned by limiting dilution. Microscopically, single clones were selected for amplification and culture, and then the supernatants were collected and analyzed by flow cytometry to detect the specific binding of subclonal supernatants to HEK293-hCLDN18.2 cells. After co-incubating the supernatant with HEK293-CLDN18.2 cells (20,000 cells/well) at 4° C. for 45 minutes, the plate was washed with Alexa Fluor®-488-goat anti-mouse IgG (ThermoFisher, Cat. No. A28175) as the secondary antibody for flow cytometry detection. To ensure the success rate of subsequent sequencing, 2 single clones (clone A and clone B) were selected for each hybridoma for amplification and cryopreserved. The flow cytometry analysis of HEK293-hCLDN18.2 cells by the subcloned positive monoclonal supernatants was shown in FIG. 8, which shows that the selected monoclonal supernatants maintain the specific binding to HEK293-hCLDN18.2 cells.

Figure 9:
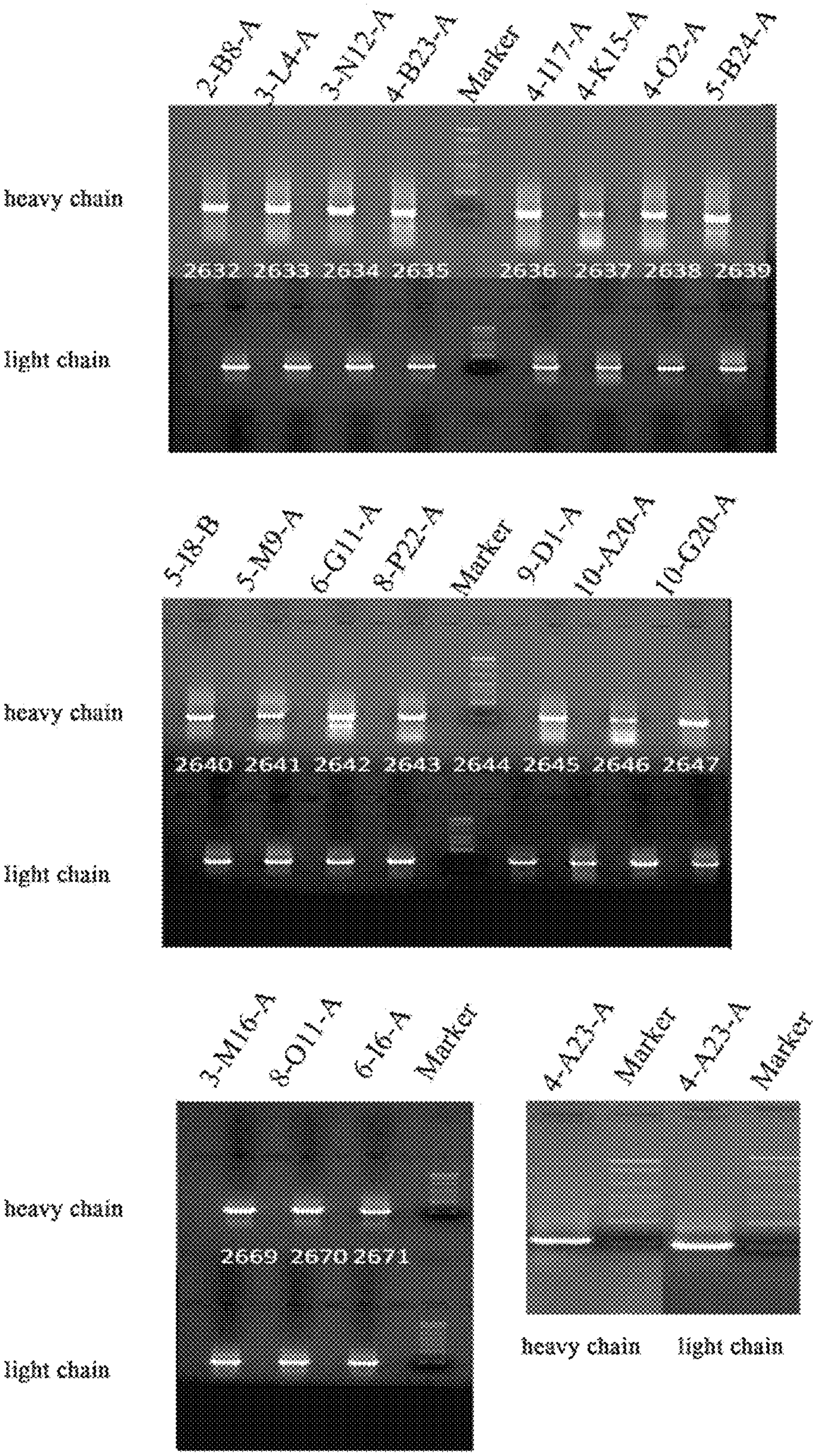
FIG. 9. PCR amplification of positive hybridoma monoclonal heavy and light chain V regions.

The DNA sequences of the VH and VL of the hybridoma monoclonal were amplified using the RACE (rapid amplification of cDNA ends) method. RNA was extracted from amplified hybridoma monoclonal cells, reverse transcribed into cDNA and the heavy chain or light chain V region was subjected to PCR by a 5'-RACE reaction using a combination of 5'-universal primers and 3'-H, L (K) or L (%) FRI region degenerate primer, and the positive amplified band was confirmed by agarose gel electrophoresis. The results were shown by FIG. 9, showing that the PCR target bands were all within a reasonable range. The PCR-positive bands on agarose gel electrophoresis were recovered by cutting the gel, and the PCR-amplified fragments were ligated to the sequencing vector for sequencing by TOPO cloning method. Tables 4 and 5 showed the heavy and light chain nucleotide and amino acid sequences of the 5M9-A and 9D1-A clones, respectively (5-M9-A and 9-D1-A represent clones; 5-M9 and 9-D1 represented the corresponding antibodies of the 5-M9-A and 9-D1-A clones). Wherein, the CDR regions in the light and heavy chains were divided according to the Chothia numbering system.

TABLE 4

| DNA sequences | |
|---|---|
| DNA sequence of heavy chain | |
| Antibody name | DNA sequence of V region |
| 5_M9 | CAGGTACAGCTGAAGGAGTCAGGACCTGTCCTGGTGGCGCCCTCACAGA GCCTGTCCATCACTTGCACTGTCTCTGGGTTTTCATTAACCACCTATGGT GTACAGTGGGTTCGCCAGCCTCCAGGAAAGGGTCTGGAGTGGCTGGGA GCAATATGGGCTGGTGGAAACACAAATTATAATTCAGCTCTCATGTCCA GACTGAGCATCAGCAAAGACAACTCCAAGAGCCAAGTTTTCTTAAAAAT GAACAGTCTGCAAACTGATGACACAGCCATATACTACTGTGCCAAAGGG GGTTACGGGAATGCTATGGACTACTGGGGTCAAGGAACCTCAGTCACCG TCGCCTCA (SEQ ID NO: 14) |
| 9-D1 | GAGATCCAGCTGCAGCAGTCTGGAGCTGAGCTGGTGAAGCCTGGGGCTT CAGTGAAGATATCCTGCAAGGCTTCTGGTTATTCATTCACTGACTACCAC ATGAACTGGGTGAGGCAGAGCCATGGAAAGAGCCTTGAGTGGATTGGA AATATTGATCCTTACTATGGTAGTCCTACCTACAATCATAAATTCAAGGG CAAGGCCACATTGACTGTAGACAAATCTTCCAGCACAGCCTACATGCAG CTCATCAGCCTGACATCTGAGGACTCTGCAGTCTATTACTGTGCAAACTA CGGAAGGGGAAATTCGTTTCCTTACTGGGGCCAAGGGACTCTGGTCACT GTCTCTGCA (SEQ ID NO: 15) |

TABLE 4-continued

| DNA sequences | |
|---|---|
| DNA sequence of light chain | |
| Antibody name | DNA sequence of V region |
| 5_M9 | GACATTGTGATGACACAGTCTCCATCCTCCCTGACTGTGACAGCAGGAGA GAGGGTCACTATGAGCTGCAAGTCCAGTCAGAGTCTGTTAAACAGTGGA AATCAAAAGAACTACTTGACCTGGTACCAACAGAAATCAGGGCAGCCTC CTAAATTGTTGATCTACTGGGCATCCACTAGGGAATCTGGGGTCCCTGATC GCTTCACAGGCAGTGGATCTGGAACAGATTTCACTCTCACCATCAGCAGT GTGCAGGCTGAAGACCTGGCAGTTTATTACTGTCAGAATGATTATTTTTTT CCATTCACGTTCGGCTCGGGGACAAAGTTGGAAATAAAA (SEQ ID NO: 16) |
| 9-D1 | GACATTGTGATGACACAGTCTCCATCCTCCCTGACTGTGACAGCAGGAGA GAAGGTCACTATGAGCTGCAAGTCCAGTCAGAGTCTGTTAAACAGTGGA AATCAAAGGAACTACTTGACCTGGTACCAGCAGAAACCAGGGCAGCCTC CTAAACTGTTACTCTACTGGGCATCCACTAGGGAATCTGGGGTCCCTGAT CGCTTCACAGGCAGTGGATCTGGAACAGATTTCACTCTCACCATCAGCAG TGTGCAGGCTGAAGACCTGGCAGTTTATTACTGTCAGAATGATTATAGTTT TCCATTCACGTTCGGCTCGGGGACAAAGTTGGAAATAAAA (SEQ ID NO: 17) |

TABLE 5

| Amino acid sequences of CDRs | | | | | | | |
|---|---|---|---|---|---|---|---|
| Heavy chain CDR sequences (Chothia numbering) | | | | | | | |
| Antibody name | FR1 | CDR1 | FR2 | CDR2 | FR3 | CDR3 | FR4 |
| 5-M9 (light chain variable region: SEQID NO: 30) | QVQLKESGP VLVAPSQSL SITCTVS (SEQ ID NO: 43) | GFSLTT Y (SEQ ID NO: 18) | GVQWVRQ PPGKGLEW LGAI (SEQ ID NO: 44) | WAGGN (SEQ ID NO: 19) | TNYNSALMSRL SISKDNSKSQVF LKMNSLQTDDT AIYYCAK(SEQ ID NO: 45) | GGYGNAMD Y (SEQ ID NO: 20) | WGQG TSVTV AS (SEQ ID NO: 46) |
| 9-D1 (heavy chain variable region: SEQ ID NO: 31) | EIQLQQSGA ELVKPGASV KISCKAS (SEQ ID NO: 47) | GYSFTD Y (SEQ ID NO: 21) | HMNWVRQ SHGKSLEW IGNI (SEQ ID NO: 48) | DPYYGS (SEQ ID NO: 22) | PTYNHKFKGKA TLTVDKSSSTA YMQLISLTSEDS AVYYCAN (SEQ ID NO: 49) | YGRGNSFPY (SEQ ID NO: 23) | WGQG TLVTV SA (SEQ ID NO: 50) |
| Light chain CDR sequences (Chothia numbering) | | | | | | | |
| Antibody name | FR1 | CDR1 | FR2 | CDR2 | FR3 | CDR3 | FR4 |
| 5-M9 (light chain variable region: SEQ ID NO: 32) | DIVMTQSPS SLTVTAGER VTMSC (SEQ ID NO: 51) | KSSQSL LNSGN QKNYL T (SEQ ID NO: 24) | WYQQKSG QPPKLLIY (SEQ ID NO: 52) | WASTRES (SEQ ID NO: 25) | GVPDRFTGSGS GTDFTLTISSVQ AEDLAVYYC (SEQ ID NO: 53) | QNDYFFP FT (SEQ ID NO: 26) | FGSGTKLEI K (SEQ ID NO: 54) |
| 9-D1 (light chain variable region: SEQ ID NO: 33) | DIVMTQSPS SLTVTAGEK VTMSC (SEQ ID NO: 55) | KSSQSL LNSGN QRNYL T (SEQ ID NO: 27) | WYQQKPG QPPKLLLY (SEQ ID NO: 56) | WASTRES (SEQ ID NO: 28) | GVPDRFTGSGS GTDFTLTISSVQ AEDLAVYYC (SEQ ID NO: 57) | QNDYSFP FT (SEQ ID NO: 29) | FGSGTKLEI K (SEQ ID NO: 58) |

Example 5. Preparation and Characterization of Human-Mouse Chimeric Antibody

The V regions of the heavy chain and light chain of the candidate mouse antibody were fused to the constant region (HC) region of the human IgG1 type heavy chain (Glm17) and the constant region (LC) of the human kappa type light chain, respectively, and human-mouse chimeric heavy chain full-length gene and light chain full-length gene were synthesized and cloned into expression vector, and sequenced for verification. The constructed expression plasmid of each candidate molecule was amplified and extracted, verified by agarose gel electrophoresis, and used as a transfection material. HEK293 cells (Tuna293™) were inoculated into shake flasks for suspension seed culture using serum-free and chemically defined media. One day before transfection, the amplified HEK293 cells were inoculated into new shake flasks and replaced with fresh medium. The heavy chain and light chain expression plasmids of each candidate mouse chimeric antibody molecule were co-transfected into HEK293 cells, and fed-batch culture was performed until the cell viability decreased, and the supernatant was collected for product purification.

Figure 10:
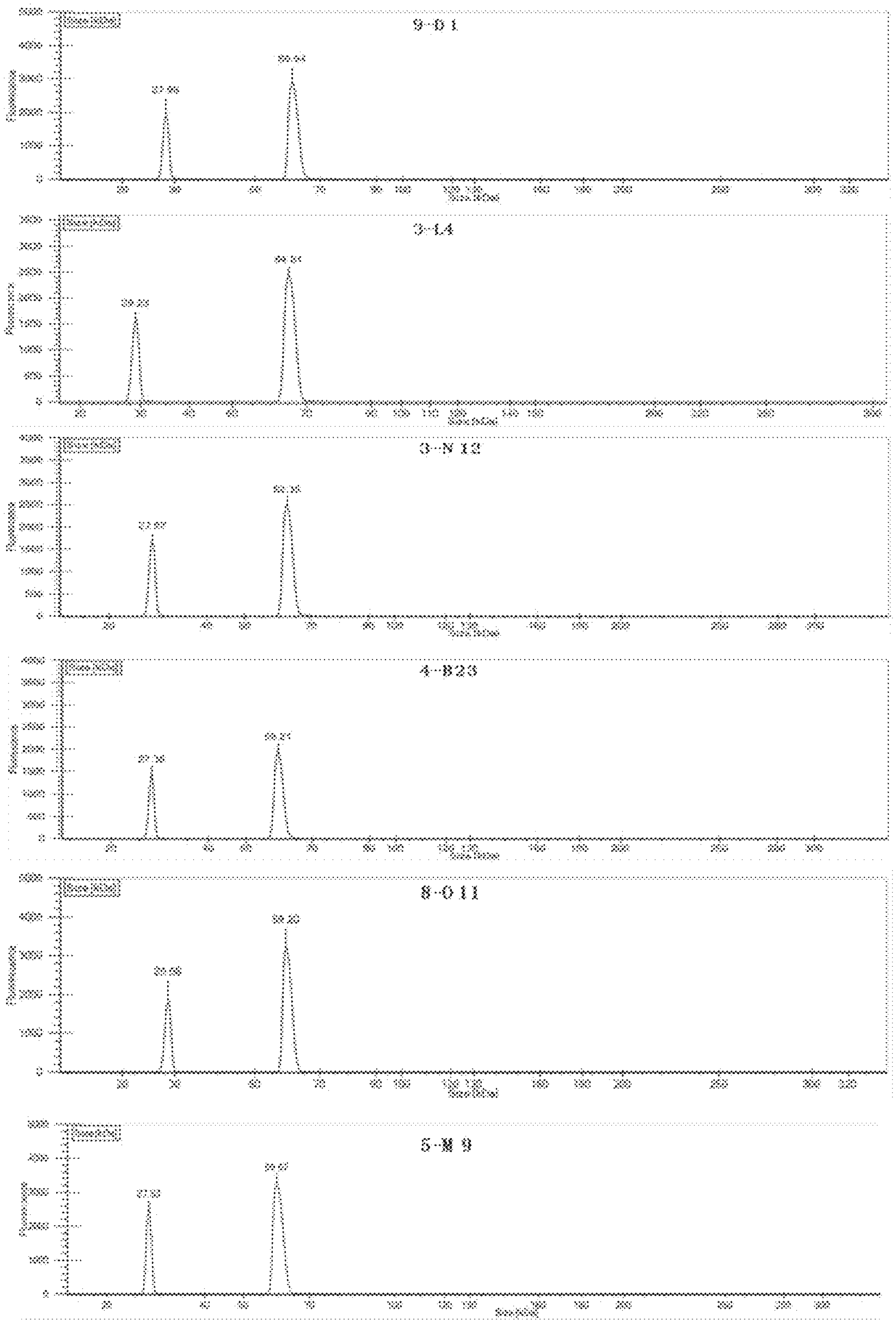
FIG. 10. Reduced CE-SDS purity detection of the purified monoclonal antibody protein.

First, most of the cell debris and insoluble particles were removed by centrifugation and filtration of the supernatant, and then the feed solution was loaded onto the Protein A column, where the antibody molecules bound to Protein A on the filler, and most impurities were removed after an equilibration step. A low pH eluent was used to elute the antibody protein and the fractions were collected. pH was adjusted and exchanged to formulation buffer by ultrafiltration. Finally, the OD280 was determined to calculate the protein concentration. The purified antibody protein was tested for purity by reducing capillary electrophoresis sodium dodecyl sulfate (CE-SDS). The reducing CE-SDS detection showed that the purity of 20 human-mouse chimeric monoclonal antibody molecules was >95% (Table 6). The reducing CE-SDS of some antibody proteins was shown in FIG. 10.

Figure 11:
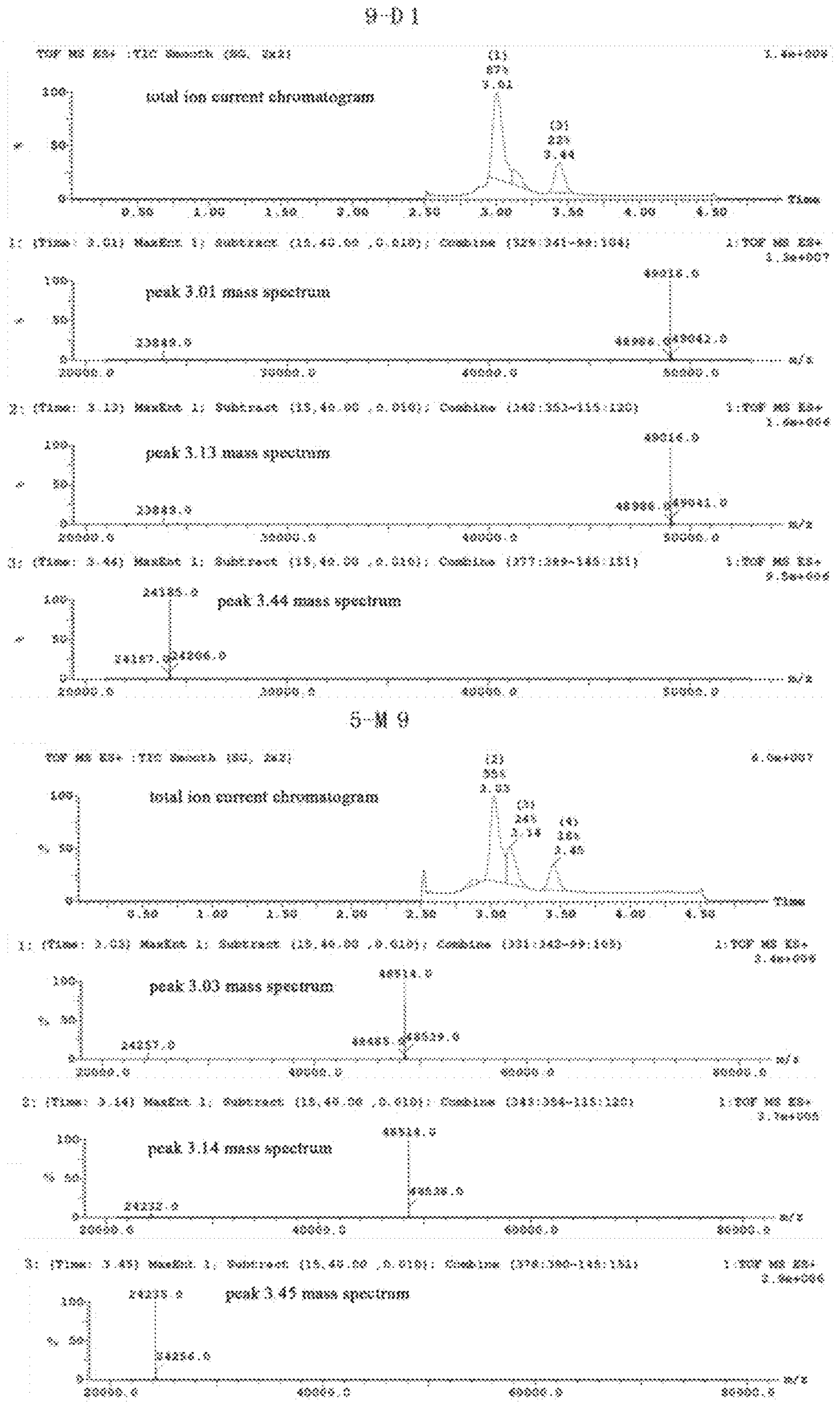
FIG. 11. Deglycosylation reduction LC/MS spectrum of the purified human-mouse chimeric monoclonal antibody protein.

After deglycosylation of purified monoclonal antibodies using deglycosylase (PNGase F) and reduction of light and heavy chains with dithiothreitol (DTT), molecular weight determination was performed by reverse chromatography tandem mass spectrometry (RP-UPLC/MS). The liquid phase part used Waters™ ACQUITY™ UPLC H-Class system, mobile phase A was 0.1% formic acid (FA)/water, mobile phase B was 0.1% FA/acetonitrile (ACN), chromatographic column was Waters™ ACQUITY™ UPLC Protein BEH C4, mass spectrometry was a Waters™ Xevo™ G2-XS Qtof, equipped with an electrospray ionization (ESI) ion source, and the scan mode was Resolution. The collected raw mass spectrometry data of the multiple-charged valence states of the target peak compounds were denoised, smoothed and deconvoluted by MassLynx software, the total ion chromatograms and deconvolution spectra of light and heavy chains of some monoclonal antibodies were shown by FIG. 11. The molecular weight determination results of 20 human-mouse chimeric monoclonal antibody molecules were shown in Table 6. For the error between the mass spectrometry molecular weight and theoretical molecular weight of all monoclonal antibodies, the heavy chain was within 5 Da, and the light chain was within 1 Da, which could be considered to be consistent with the theoretical value. It was worth mentioning that due to the conformational changes of antibody proteins in different degrees during sample processing and liquid phase determination, the retention time of heavy chain peaks on the chromatographic column changed, which was manifested as peak splitting phenomenon, and the molecular weights of the two heavy chain peaks which was split by mass spectrometry were consistent.

Example 6. Determination of the Affinity of Human-Mouse Chimeric Monoclonal Antibody to Cell Surface CLDN18.2

In this example, the affinity of 20 purified human-mouse chimeric monoclonal antibodies to cell surface CLDN18.2 was determined by flow cytometry. The determination

TABLE 6

| Clone number | Concentration (mg/mL) | Purity (R-CE-SDS %) | Heavy chain molecular weight (Da) | Light chain molecular weight (Da) | Theoretical molecular weight of heavy chain (Da) | Theoretical molecular weight of light chain (Da) | Differences in heavy chain molecular weight (Da) | Differences in light chain molecular weight (Da) | Pass/fail |
|---|---|---|---|---|---|---|---|---|---|
| 9-D1-A | 0.5 | >95% | 49016 | 24185 | 49014.3 | 24184.9 | 1.7 | 0.1 | pass |
| 8-P3-A | 0.51 | >95% | 48953 | 23999 | 48951.4 | 23998.7 | 1.6 | 0.3 | pass |
| 8-P22-A | 0.5 | >95% | 48544 | 24085 | 48541.9 | 24084.8 | 2.1 | 0.2 | pass |
| 8-O11-A | 0.5 | >95% | 49046 | 24188 | 49043.6 | 24187.9 | 2.4 | 0.1 | pass |
| 6-I6-A | 0.51 | >95% | 48784 | 24177 | 48782.1 | 24176.9 | 1.9 | 0.1 | pass |
| 6-G11-A | 0.5 | >95% | 48925 | 24154 | 48923.1 | 24153.9 | 1.9 | 0.1 | pass |
| 5-M9-A | 0.5 | >95% | 48514 | 24235 | 48511.9 | 24235 | 2.1 | 0.0 | pass |
| 5-I8-B | 0.5 | >95% | 48879 | 24148 | 48877.2 | 24148 | 1.8 | 0.0 | pass |
| 5-B24-A | 0.5 | >95% | 48704 | 24159 | 48701.1 | 24159 | 2.9 | 0.0 | pass |
| 4-O2-A | 0.5 | >95% | 48925 | 24163 | 48923.1 | 24162 | 1.9 | 1.0 | pass |
| 4-K15-A | 0.5 | >95% | 48940 | 23443 | 48938.2 | 23443.2 | 1.8 | −0.2 | pass |
| 4-I17-A | 0.51 | >95% | 48999 | 23480 | 48997.4 | 23479.3 | 1.6 | 0.7 | pass |
| 4-B23-A | 0.5 | >95% | 48657 | 24305 | 48661.1 | 24305.1 | −4.1 | −0.1 | pass |
| 4-A23-A | 0.5 | >95% | 48920 | 24111 | 48918.4 | 24110.9 | 1.6 | 0.1 | pass |
| 3-N12-A | 0.5 | >95% | 49148 | 24091 | 49146.4 | 24090.9 | 1.6 | 0.1 | pass |
| 3-M16-A | 0.5 | >95% | 48803 | 24191 | 48801.3 | 24191 | 1.7 | 0.0 | pass |
| 3-L4-A | 0.51 | >95% | 48925 | 24153 | 48923.1 | 24152.9 | 1.9 | 0.1 | pass |
| 2-B8-A | 0.5 | >95% | 48620 | 24094 | 48618 | 24093.8 | 2.0 | 0.2 | pass |
| 10-G20-A | 0.5 | >95% | 49048 | 23954 | 49046.5 | 23953.7 | 1.5 | 0.3 | pass |
| 10-A20-A | 0.5 | >95% | 49017 | 23896 | 49015.4 | 23895.6 | 1.6 | 0.4 | pass |

method for cell surface protein affinity refers to the direct FACS binding method described in Hunter S. A. et al, Methods in Enzymology, 2016, 580, 21-44. After resuscitation of HEK293 cells (HEK293-hCLDN18.2) stably expressing CLDN18.2, they were cultured and passaged until a certain number of cells were reached. The cells were distributed to 1 mL centrifuge tubes at a density of $5\times10^4$/mL, and centrifuged for use.

A series of antibody concentrations were prepared for each monoclonal antibody (10 μg/mL, 3.3 μg/mL, 1.1 μg/mL, 0.37 μg/mL, 0.1123 μg/mL, 0.0041 μg/mL, 0.0013 μg/mL). To eliminate ligand depletion effects (Ligand Depletion), antibody concentration series were prepared using PBS binding buffer diluted to the corresponding ligand depletion volume. HEK293-hCLDN18.2 cells were mixed and incubated with serial concentrations of antibodies formulated to the ligand elimination volume, and incubated at 4° C. until equilibrium. The cells were collected by centrifugation at 4° C., washed with pre-cooled PBS, incubated with the anti-human IgG secondary antibody with fluorescent dye for 30 minutes at 4° C., washed once with pre-cooled PBS, and then subjected to FACS binding analysis, and nonlinear curve regression was performed according to the results to calculate binding kinetic constant (KD) values. The results were shown in Table 7, showing that the affinities (KD) of all antibodies were at the subnanomoler level. Some antibodies had lower affinity than positive control antibodies (also known as Benchmark, BM) 163E12 (the amino acid sequence of the heavy chain was SEQ ID NO: 12; the amino acid sequence of the light chain was SEQ ID NO: 13) and 175D10 (the amino acid sequence of the heavy chain was SEQ ID NO: 10; the amino acid sequence of the light chain was SEQ ID NO: 11) by 3 to 5 times, reaching a nearly picomolar affinity.

TABLE 7

| Antibody | FACS $K_D$(nM) |
|---|---|
| 163E12 | 0.137 |
| 175D10 | 0.189 |
| 2-B8-A | 0.061 |
| 3-L4-A | 0.048 |
| 3-N12-A | 0.035 |
| 4-B23-A | 0.041 |
| 4-I17-A | 0.085 |
| 4-K15-A | 0.109 |
| 4-O2-A | 0.046 |
| 5-B24-A | 0.053 |
| 5-I8-A | 0.090 |
| 5-M9-A | 0.048 |
| 6-G11-A | 0.042 |
| 8-P22-A | 0.044 |
| 8-P3-A | 0.041 |
| 9-D1-A | 0.049 |
| 10-A20-A | 0.049 |
| 10-G20-A | 0.038 |
| 3-M16-A | 0.095 |
| 8-O11-A | 0.121 |
| 6-I6-A | 0.112 |
| 4-A23-A | 0.114 |

Example 7. Antibody-Dependent Cellular Cytotoxicity (ADCC) Function of Human-Mouse Chimeric Monoclonal Antibody In this example, the ADCC function of the purified human-mouse chimeric monoclonal antibody was assayed by the effector cell reporter gene method. The effector cells in this method are the Jurkat cell line (Promega, G7018) stably expressing human Fc receptor (FcγRIIIa V158) and NFAT (nuclear factor for activated T cells) in response to inducible expression of luciferase (NFAT-RE-Luc). When the effector cell binds to the Fc region of the relevant test antibody bound to the target cell, it activates the FcγRIIIa receptor on the responding cell, further activates the intracellular NFAT cell signaling pathway, and mediates the expression of NFAT corresponding luciferase. The ADCC effect was determined by quantifying this fluorescent activity.

The antibody concentration was serially diluted 5 times starting from 2 μg/mL to obtain 8 concentrations (respectively 2000 ng/ml, 400 ng/ml, 80 ng/ml, 16 ng/ml, 3.2 ng/ml, 0.64 ng/ml, 0.128 ng/mL, 0.0256 ng/ml) of serially diluted antibody samples. The antibody sample was mixed with target cells stably expressing human CLDN18.2 (HEK293-hCLDN18.2), and then effector cells were added. The effector-target ratio of effector cells to target cells was 5:1 (75000:15000). The reaction system was incubated at 37° C. for 6 hours, fluorescein substrate was added and the fluorescence intensity (RLU) was read. The induction fold of the ordinate was calculated by the following formula:

Induction fold=(induced fluorescence intensity-background fluorescence intensity)/(no antibody control fluorescence intensity-background fluorescence intensity).

Figure 12:
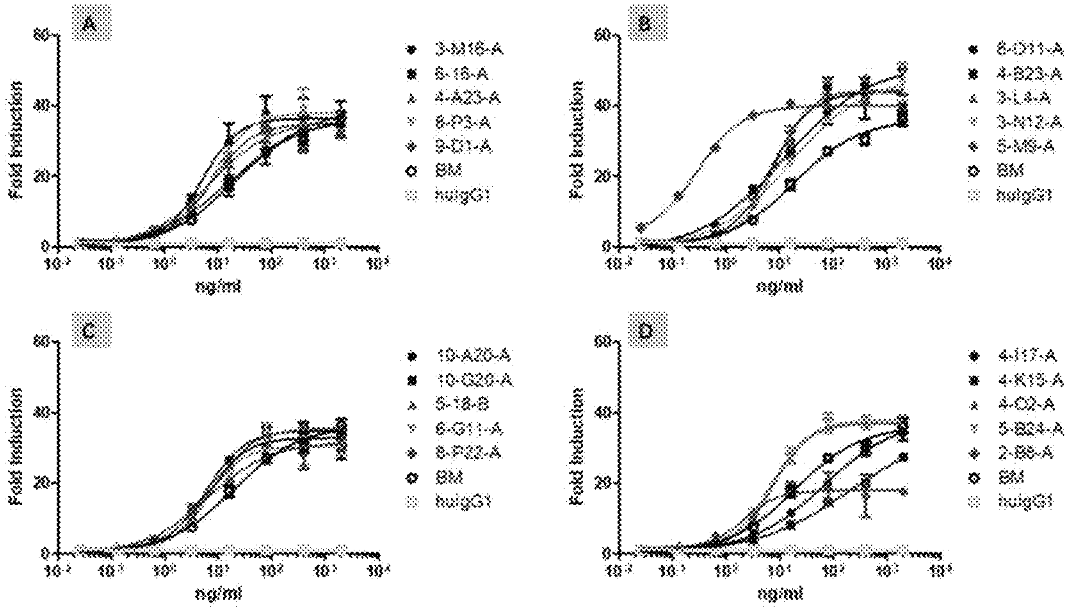
FIG. 12. ADCC effect of the purified human-mouse chimeric monoclonal antibody.

The ADCC effect results of 20 purified human-mouse chimeric monoclonal antibodies were shown in FIG. 12, and the corresponding ADCC maximum killing and half effective dose (EC50) were shown in Table 8, showing most of the antibodies (17/20) had stronger ADCC effect at half effective dose than positive control antibody (163E12). The maximum killing of the 2-B8-A clone was significantly lower than that of the control antibody. Among them, the EC50 (0.287 pg/mL) of 5-M9-A monoclonal antibody was significantly higher than that of the positive control antibody (19.5 pg/mL), and its maximum killing (40 times) was also significantly higher than that of the control antibody (36.3 times).

TABLE 8

| Antibody | Maximum induction fold | EC50 (ng/mL) |
|---|---|---|
| Positive control antibody (163E12) | 36.3 | 1.95E−02 |
| IgG1 isotype control antibody (Abcam Cat. NO. ab206198) | about 1.559 | — |
| 2-B8-A | 17.9 | 2.15E−03 |
| 3-L4-A | 44.4 | 8.32E−03 |
| 3-N12-A | 48.2 | 1.57E−02 |
| 4-B23-A | 44.0 | 7.20E−03 |
| 4-I17-A | 38.3 | 6.65E−02 |
| 4-K15-A | 35.4 | 1.99E−01 |
| 4-O2-A | 37.0 | 7.41E−03 |
| 5-B24-A | 38.0 | 6.91E−03 |
| 5-I8-B | 35.6 | 7.23E−03 |
| 5-M9-A | 40.0 | 2.87E−04 |
| 6-G11-A | 30.4 | 6.35E−03 |
| 8-P22-A | 31.7 | 6.45E−03 |
| 8-P3-A | 38.0 | 7.74E−03 |
| 9-D1-A | 35.0 | 7.40E−03 |
| 10-A20-A | 32.9 | 6.89E−03 |
| 10-G20-A | 34.9 | 6.11E−03 |
| 3-M16-A | 36.5 | 5.13E−03 |
| 8-O11-A | 52.0 | 1.25E−02 |
| 6-I6-A | 39.9 | 2.11E−02 |
| 4-A23-A | 35.7 | 7.32E−03 |

Figure 13:
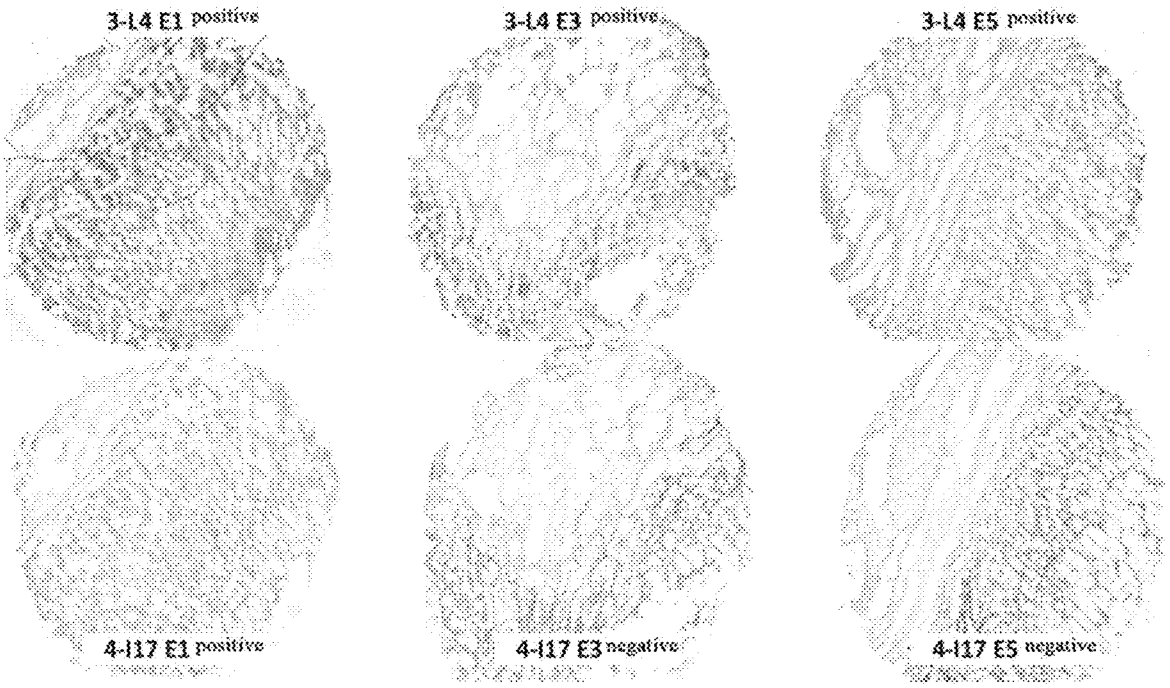
FIG. 13. IHC staining of 3-L4 and 4-117 on some gastric cancer tissue sections.

Example 8. Immunohistochemistry (IHC) Study of Hybridoma Antibodies on Gastric Cancer Tissue Frozen Tissue Chips, Normal Gastric Tissues and Vital Organ Tissues In this example, immunohistochemical methods were used to detect the binding of 20 hybridoma antibodies to normal gastric tissue and gastric cancer tissue on a frozen tissue chip. First, the concentration of mouse IgG antibody in the supernatant of 20 hybridomas was quantified by the Elisa method, and then the supernatant of hybridoma was diluted according to the quantification results of mouse IgG in the supernatant of hybridoma, and the IHC of the hybridoma supernatant on gastric mucosal epithelial glands was verified on the frozen section of normal gastric tissue, and the IHC study of 20 hybridoma supernatants on human normal gastric tissue and gastric cancer tissue frozen chip (Tissue Micro Array, TMA) (BioMax, FST401) was carried out using the verified IHC conditions. The frozen tissue chip was incubated with the supernatant of each hybridoma of the verified concentration at 37° C., then washed with PBS buffer three times, and then incubated with HRP-labeled anti-mouse IgG secondary antibody at 37° C., using the diaminobenzidine (DAB) method to develop color. Table 9 summarizes the IHC results of the supernatants of 20 hybridoma clones on frozen TMA containing 16 gastric cancer tissues and 4 normal gastric tissues. Among them, the positive staining rates of 5-M9, 3-N12, 3-L4, 9-D1 and 4-B23 in gastric cancer tissue were all higher than 67%, but in the staining of normal gastric tissue epithelial cells, the positive staining rate of 9-D1 was only 25%, which was significantly lower than that of the other 4 clones (>50%), which indicated that the 9-D1 antibody had higher positive staining on gastric tumor tissue, and at the same time, it bound weakly to normal gastric mucosal epithelium. This meant that 9-D1 as a therapeutic antibody would have lower toxicity (on target off tumor toxicity) in normal tissues expressed on extra-tumor targets, which suggested that 9-D1 antibody may had a strong advantage in druggability. Screening antibodies that had strong binding to targets in tumor tissues and weak binding to targets in normal tissues was a new trend in screening therapeutic antibodies in recent years. Because of the special physiological environment of tumor tissue, the molecular structure of many targets on tumor cells was different from that of targets that maintain normal functions in normal tissues, and screening of tumor target-specific antibodies could specifically recognize this difference (Garrett T. P. J. et al, PNAS, 2009, 106 (13), 5082-5087). Examples of IHC staining of 3-L4 and 4-117 on some gastric cancer chip tissues were shown in FIG. 13.

TABLE 9

| Position | Diagnosis type | 8-P22 | 9-D1 | 4-A23 | 16-I6 | 3-M16 | 6-G11 | 10-A20 | 2-B8 | 4-O2 | 10-G20 |
|---|---|---|---|---|---|---|---|---|---|---|---|
| A1-2 | gastric adenocarcinoma | (1)*10%# | (3)50% | (2)50% | (2)50% | (2)50% | (2)40% | (2)10% | (2)40% | (2)40% | (1)10% |
| A3-4 | gastric adenocarcinoma | — | — | — | — | — | — | — | — | — | — |
| A5-6 | gastric adenocarcinoma | — | (1)5% | — | — | (1)10% | — | — | — | (1)5% | — |
| A7-8 | gastric adenocarcinoma | (2)10% | (4)20% | (4)10% | (3)10% | (3)10% | (2)10% | (2)10% | (3)10% | (3)20% | (2)10% |
| B1-2 | gastric adenocarcinoma | — | (1)5% | — | — | — | — | — | — | — | — |
| B3-4 | gastric adenocarcinoma | — | — | — | — | — | — | — | — | — | — |
| B5-6 | gastric adenocarcinoma | — | — | — | — | — | — | (1)40% | — | — | — |
| B7-8 | gastric adenocarcinoma | — | (1)5% | — | — | — | — | (1)5% | — | — | — |
| C1-2 | gastric adenocarcinoma | — | (2)10% | (2)10% | (2)10% | (1)10% | (1)5% | (1)50% | (1)40% | (1)20% | (1)10% |
| C3-4 | gastric adenocarcinoma | — | — | — | — | — | — | — | — | — | — |
| C5-6 | gastric adenocarcinoma | — | — | — | — | — | — | — | — | — | — |
| C7-8 | gastric adenocarcinoma | — | — | — | — | — | — | (1)5% | — | — | — |
| D1-2 | gastric adenocarcinoma | — | (1)10% | — | (1)5% | (1)5% | (1)5% | (1)5% | (1)5% | (1)5% | — |
| D3-4 | gastric adenocarcinoma | — | (1)20% | (1)20% | — | (2)50% | — | — | (2)40% | (1)5% | — |
| D5-6 | gastric adenocarcinoma | (2)5% | (2)50% | (2)50% | (2)40% | (1)30% | (2)10% | (1)20% | (1)10% | (1)10% | (1)10% |

TABLE 9-continued

| | | | | | | | | | | | |
|---|---|---|---|---|---|---|---|---|---|---|---|
| D7-8 | gastric adenocar-cinoma | (1)5% | (4)50% | (3)50% | (1)10% | (2)10% | (1)5% | (3)10% | (1)10% | (1)20% | (1)5% |
| E1-2 | normal stomach | (2)40% | (2)40% | (2)40% | (0.5)40% | (2)40% | (3)80% | (3)80% | (3)80% | (2)50% | (2)50% |
| E3-4 | normal stomach | — | — | — | — | — | — | — | — | — | — |
| E5-6 | normal stomach | — | — | — | — | — | — | — | — | — | — |
| E7-8 | normal stomach | — | — | — | — | — | — | — | — | — | — |
| Positive rate | tumor tissue % | 27%$ | 67% | 41% | 41% | 53% | 41% | 60% | 47% | 53% | 33% |
| | normal tissue % | 25% | 25% | 25% | 25% | 25% | 25% | 25% | 25% | 25% | 25% |
| | **Position** | **8-P3** | **5-18** | **5-B24** | **4-K15** | **4-117** | **4-B23** | **8-011** | **5-M9** | **3-N12** | **3-L4** |
| | A1-2 | (1)20% | (2)50% | (1)20% | (2)20% | (1)20% | (1)10% | (1)10% | (1)20% | (1)5% | (1)5% |
| | A3-4 | — | — | — | — | — | — | — | — | — | — |
| | A5-6 | — | — | — | — | — | — | — | — | — | — |
| | A7-8 | (4)10% | (4)20% | (3)10% | (3)10% | (3)10% | (1)10% | — | (1)20% | (1)5% | (1)5% |
| | B1-2 | — | (1)10% | — | — | — | (2)10% | (1)5% | (1)20% | (1)5% | — |
| | B3-4 | — | — | — | — | — | — | — | — | — | — |
| | B5-6 | — | — | — | — | — | (3)40% | — | — | (0.5)10% | — |
| | B7-8 | — | — | — | — | — | — | — | (1)10% | (1)5% | (1)5% |
| | C1-2 | (1)5% | (1)5% | (1)10% | (1)10% | (1)10% | (2)90% | — | (2)90% | (1)80% | (1)80% |
| | C3-4 | — | — | — | — | — | (1)40% | — | — | (1)40% | (1)40% |
| | C5-6 | — | — | — | — | — | — | — | — | — | — |
| | C7-8 | — | — | — | — | — | — | (2)40% | (3)20% | (2)20% | (4)40% |
| | D1-2 | — | — | — | — | — | (1)5% | — | (1)5% | — | (1)5% |
| | D3-4 | — | — | — | — | — | (4)40% | (1)80% | (1)80% | (1)60% | (1)80% |
| | D5-6 | (1)30% | (2)20% | (2)10% | (2)10% | (3)10% | (1)20% | (1)30% | (1)20% | (1)20% | (1)20% |
| | D7-8 | (1)5% | (2)5% | (2)10% | (2)10% | (2)10% | (1)10% | (0.5)20% | (2)10% | (1)10% | (1)20% |
| | E1-2 | (2)50% | (2)40% | (2)50% | (2)40% | (2)40% | (1)90% | (0.5)60% | (2)80% | (2)80% | (2)80% |
| | E3-4 | — | — | — | — | — | (1)10% | (1)20% | (2)80% | (2)80% | (2)80% |
| | E5-6 | — | — | — | — | — | — | (1)40% | (2)80% | (1)40% | (1)40% |
| | E7-8 | — | — | — | — | — | — | — | — | — | — |
| | Positive | 33% | 41% | 33% | 33% | 33% | 67% | 41% | 67% | 74% | 67% |
| | rate | 25% | 25% | 25% | 25% | 25% | 50% | 75% | 75% | 75% | 75% |

Note:
In the chip section, * the numbers in brackets are staining intensity, and # percentage is the percentage of positive cells. In the positive statistics (Pos. Rate) section, $ percentage is the positive rate of the antibody in all gastric cancer chips and normal gastric tissue chips. There are no gastric cancer cells on the C5-6 tissue points by microscopy, and they are not included in the statistics.

Figure 14:
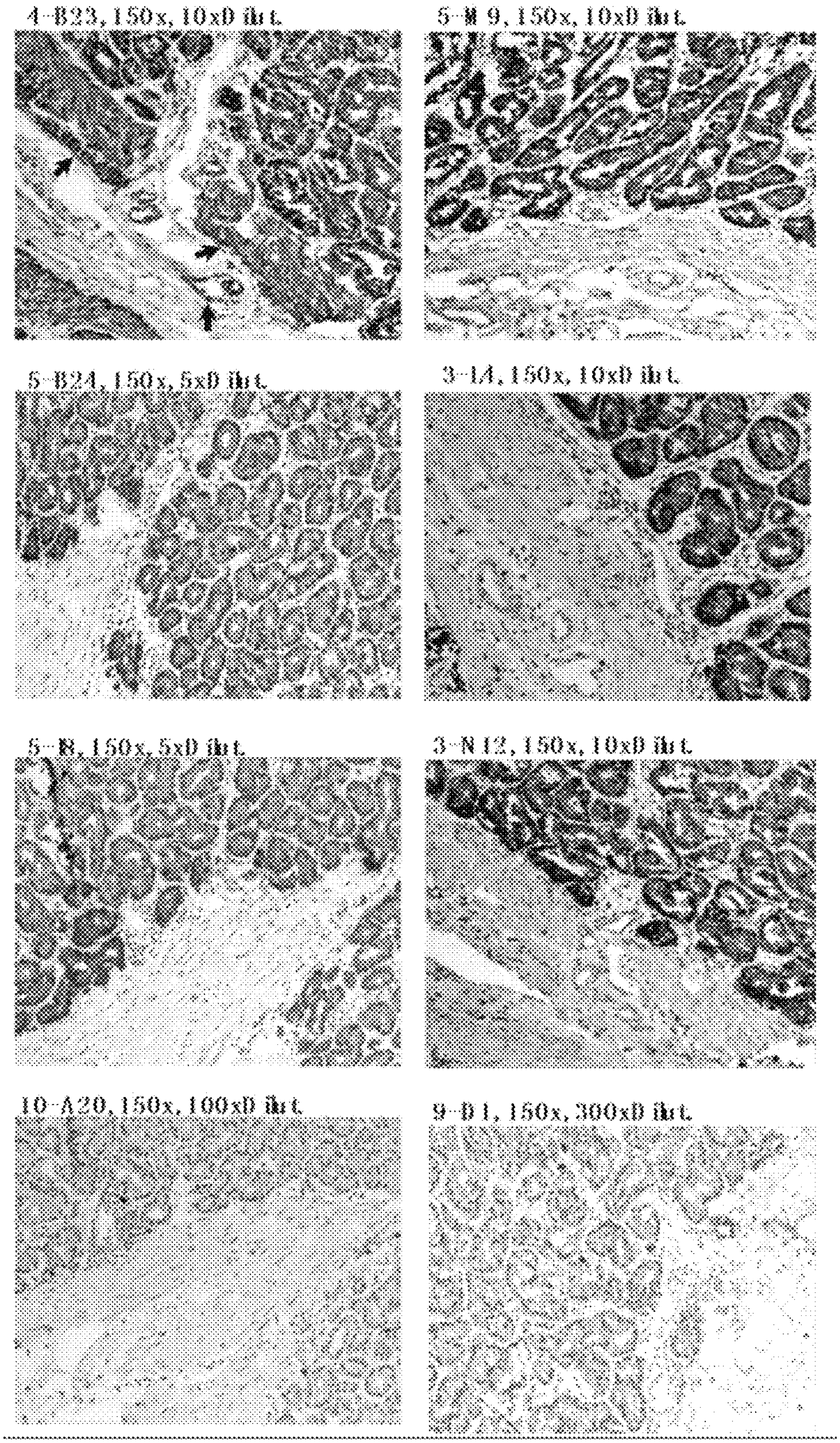
FIG. 14. IHC staining of hybridoma clone supernatants on frozen sections of normal gastric tissues.

It was worth noting that when 4-B23 was subjected to IHC condition exploration on normal gastric frozen tissue sections, a very obvious non-specific strong IHC staining was found, and the non-specific staining mainly concentrated on smooth muscle on gastric tissue. FIG. 14 showed the IHC staining of B23 and some other clones on frozen sections of normal gastric tissue. The arrows showed the strong non-specific coloration of 4-B23 in the smooth muscle of the lower layer of the gastric gland and the smooth muscle of the blood vessels. The positive staining of other clones was specific for epithelial cells located in gastric glands.

Figure 15:
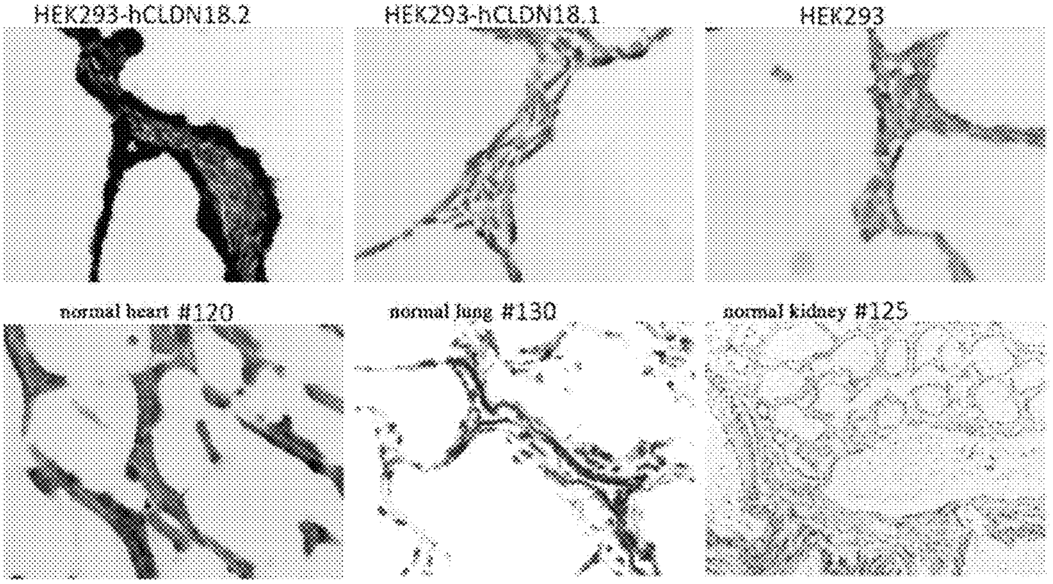
FIG. 15. Non-specific IHC staining of 4-B23 hybridoma clone supernatants on human normal tissues.

The IHC staining results of the monoclonal supernatants of 5 hybridomas (4-B23, 3-N12, 5-M9, 8-O11 and 3-L4) on normal human heart, liver, spleen, lung and kidney frozen tissues were summarized as follows shown in Table 10. Among them, the positive control antibodies (163E12), 3-N12, 5-M9, 8-O11 and 3-L4 were negative for IHC staining on the frozen tissues of normal human heart, liver, spleen, lung and kidney, and for 4-B23, strong positive staining appeared on the above-mentioned tissues of all vital organs. FIG. 15 showed positive staining for 4-B23 on frozen sections of HEK293-hCLDN18.2 cell block and negative staining on HEK293-hCLDN18.1 and HEK293, but positive staining on heart, lung and kidney with strong staining sites were all located in smooth muscle, consistent with the non-specific staining in submucosa smooth muscle on normal gastric tissue. This suggested that 4-B23 might have unexpected clinical toxicity caused by non-specific binding and was not druggable.

TABLE 10

| Antibody | Heart (3 cases) | Liver (3 cases) | Spleen (3 cases) | Lung (3 cases) | Kidney (3 cases) |
|---|---|---|---|---|---|
| 163E12 | – | – | – | – | – |
| IgGisotype control (ThermoFisher, Cat. NO. 12000C) | – | – | – | – | – |
| 4-B23 | + | + | + | + | + |
| 3-N12 | – | – | – | – | – |
| 5-M9 | – | – | – | – | – |
| 8-O11 | – | – | – | – | – |
| 3-L4 | – | – | – | – | – |

Example 9. Sequence Humanization of Monoclonal Antibodies 5-M9 and 9-D1

Sequence humanization of antibodies 5-M9 and 9-D1 was performed in a manner based on antibody 3D modeling (Kurella et al, Methods Mol. Biol., 2018, 1827, 3-14), and the design process was performed using commercial Schrodinger's Bioluminate software. Firstly, the homology modeling of the heavy chain V region and the light chain V region of the antibody was performed, and the VH and VL structures with the highest sequence homology were selected as templates by sequence alignment with the existing antibody sequences in the PDB (Protein Data Bank) database. The VH and VL of the antibody to be modeled were separately modeled in 3D. The 3D modeled VH and VL framework regions were then analyzed and assigned important amino acid residues of CDR regions, Canonical folds, Vernier regions and VH/VL binding region (interface). By aligning the VH and VL of the antibody to be humanized with the germline genes of the human antibody, the human germline gene with the highest degree of homology was found as the template for humanization, and then the CDR of the antibody to be humanized was transplanted into the corresponding human germline gene framework region. Three basic principles were used to determine whether to restore the important amino acids in the CDR-transplanted human framework region: 1) if the amino acid residues in the human framework region on the 3D structure produced new contact sites (ionic bonds, hydrogen bonds and hydrophobic interactions) to the CDR region, canonical fold, Vernier region and VH/VL binding region (interface), and the corresponding human amino acid residues in the framework region were mutated to the corresponding residues in the mouse framework region; 2) if the original mouse-derived framework region and CDR region, canonical fold, Vernier region and VH/VL binding region (interface) on the 3D structure had the amino acid residues of the original contact site (ionic bond, hydrogen bond and hydrophobic interaction), after replacing with the amino acid residues of the corresponding human framework region, the contact site was weakened or disappeared, and the corresponding human-derived amino acids residues in the framework region were re-mutated to those corresponding to mouse-derived framework regions; 3) replacing the amino acid residues of the typical mouse-derived Canonical fold, Vernier region and VH/VL binding region (interface) with human-derived amino acid residues require careful study and careful substitution. For the humanized antibody predicted by the above principles, based on the 3D structure, Schrodinger software further conducted 1) protein surface analysis, and annotated the amino acids that formed a larger hydrophobic exposed area relative to the surface of the mouse-derived antibody after humanization. If humanized antibodies formed more aggregates in subsequent preparation and characterization, the amino acid residues with larger hydrophobic exposed regions were modified to destroy the corresponding surface hydrophobic regions; 2) analysis of amino acid post-translational modifications, for the amino acid side chains that were prone to post-translational modifications after humanization, the amino acid residues with >50% exposure on the surface of the 3D structure were annotated. If the humanized antibody had post-translational modifications in the subsequent preparation and characterization, the high-risk post-translational modification amino acid residues with surface exposure were modified; 3) the immunogenicity analysis of the antibody sequence comprised T cell epitope analysis, B cell epitope analysis, and MHC II epitope analysis, and the positions of peptides with high immunogenicity for producing Anti-Drug-Antibody (ADA) were annotated.

Figure 16:
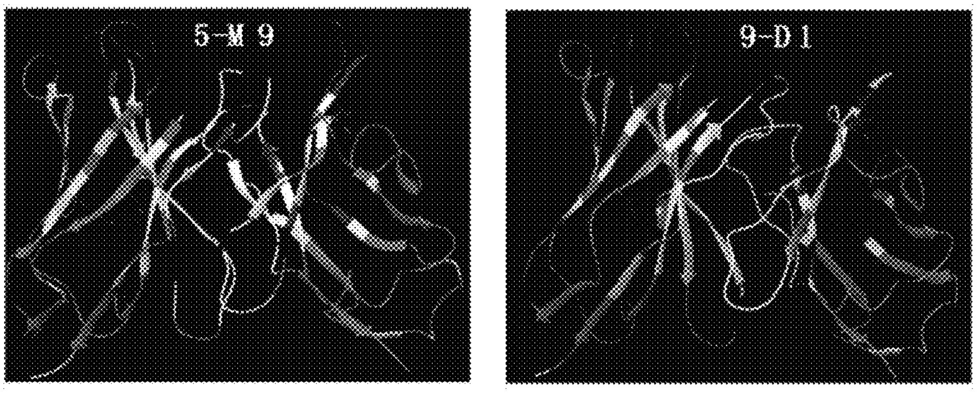
FIG. 16. Homologous 3D modeling of the 5-M9 and 9-D1 Fv regions.
Figure 17:
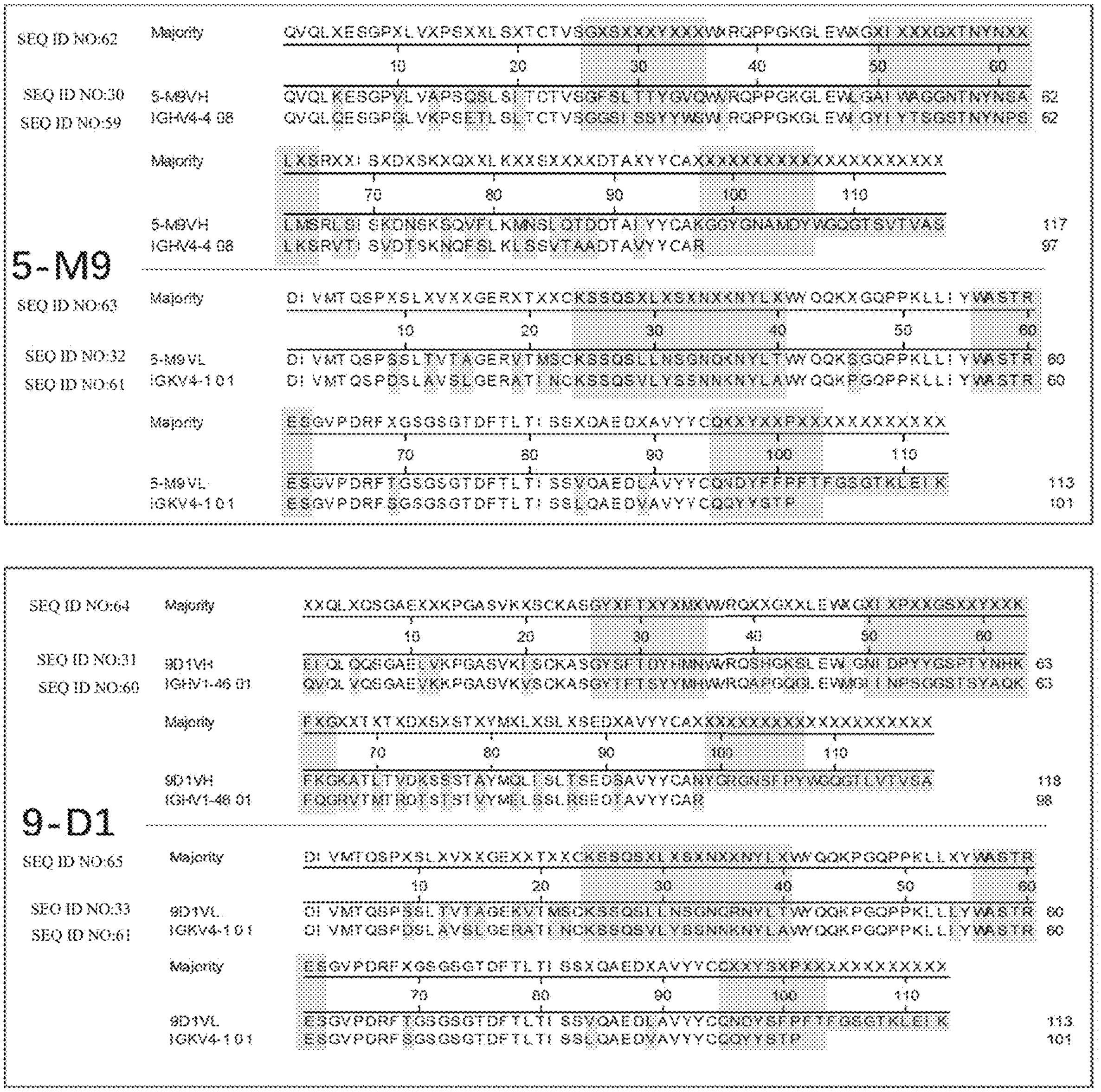
FIG. 17. Sequence alignment of VH and VL of 5-M9 and 9-D1 with human germline genes as transplant receptor frameworks for CDRs.

FIG. 16 showed the homologous 3D models of the 5-M9 and 9-D1 Fv regions using 3KJ4 and 4M61 in the PBD database as templates, respectively, the dark red regions were CDRs regions, and the white and gray regions were VH/VL interface-bound amino acid residues, the yellow region was the canonical fold amino acid residues, and the green region was the Vernier region amino acid residues. FIG. 17 showed the human antibody germline genes IGHV4-4*8, IGKV4-1*01, IGHV1-46*01 and IGKV4-1*01 with the highest VH and VL homology to 5-M9 and 9-D1, respectively, and the framework regions corresponding to human germline genes would be the recipient frameworks for transplantation of 5-M9 and 9-D1 VH and VL CDRs, respectively. The dark regions were sensitive amino acids in the CDRs region, Canonical fold and Vernier regions, and yellow regions except dark regions indicated amino acid residues were the differential amino acids between human germline genes and mouse-derived antibody sequences.

Figure 18:
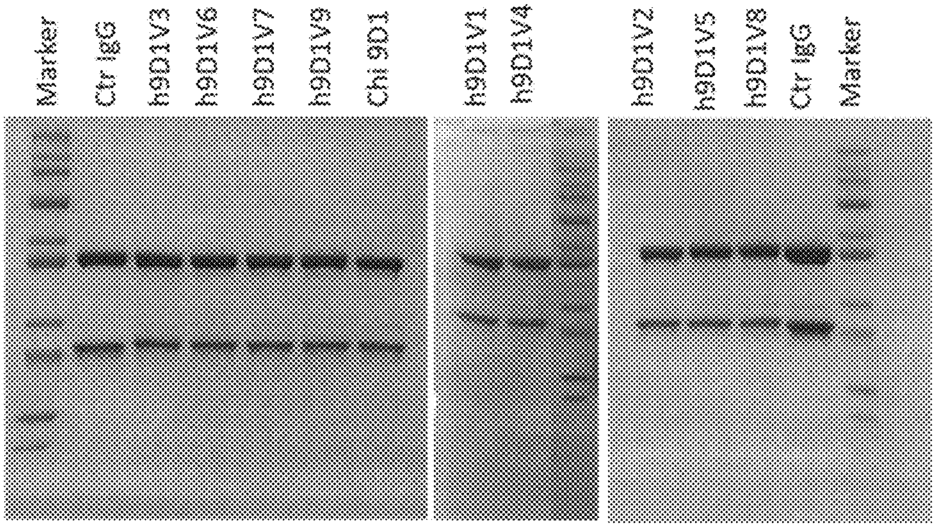
FIG. 18. Reduced SDS-PAGE detection after purification of 9-D1 humanized antibody molecule protein.

3-4 humanized sequences were provided for VH and VL of each antibody sequence, respectively. Table 11 lists the degree of humanization of the mouse-derived sequences of VH and VL and the corresponding humanized sequences, and the degree of humanization of VH was increased from about 60% of the mouse-derived sequences to a maximum of about 80%, and the degree of humanization of VL was increased from about 80% of the mouse-derived sequences to a maximum of about 90%. Full-length gene synthesis was performed for the humanized heavy chain and light chain, and the heavy chain and light chain constant regions were human IgG1 (Glm17) heavy chain and human k type light chain, respectively. The full-length gene was cloned into an expression plasmid, and the heavy chain and light chain expression plasmids were permutated, combined and co-transfected with HEK293 for antibody expression. Table 12 showed the expression of humanized molecules according to the permutation and combination of VH/VL humanized sequences, showing that 5-M9 expresses a total of 12 humanized molecules, and 9-D1 expresses a total of 9 humanized molecules. FIG. 18 showed the reducing SDS-PAGE electropherogram of the purified 9-D1 humanized antibody molecule protein, showing that the electrophoretic purity of the 9 humanized versions was >95%, and the molecular weights of the bands of the heavy and light chains were in line with expectations, which were consistent with the position of the control human-derived IgG1 antibody.

TABLE 11

| Heavy chain | Degree of of humanization | Light chain | Degree of humanization |
|---|---|---|---|
| 5-M9VH | 60.8% | 5-M9VL | 80.2% |
| h5M9VHv1 | 78.4% | h5M9VLv1 | 87.1% |
| h5M9VHv2 | 77.3% | h5m9VHv2 | 86.1% |
| h5M9VHv3 | 72.2% | h5M9VHv3 | 85.1% |
| h5M9VHv4 | 71.2% | | |
| 9-D1VH | 63.9% | 9-D1VL | 79.2% |
| h9D5VHv1 | 79.4% | h9D1VLv1 | 90.1% |
| h9D5VHv2 | 78.4% | h9D1VHv2 | 88.1% |
| h9D5VHv3 | 77.4% | h9D1VHv3 | 87.1% |

TABLE 12

| IgG number | HC number | LC number |
|---|---|---|
| h5M9v1 | h5M9 VHv1 | h5M9 VLv1 |
| h5M9v2 | h5M9 VHv1 | h5M9 VLv2 |
| h5M9v3 | h5M9 VHv1 | h5M9 VLv3 |
| h5M9v4 | h5M9 VHv2 | h5M9 VLv1 |
| h5M9v5 | h5M9 VHv2 | h5M9 VLv2 |
| h5M9v6 | h5M9 VHv2 | h5M9 VLv3 |
| h5M9v7 | h5M9 VHv3 | h5M9 VLv1 |
| h5M9v8 | h5M9 VHv3 | h5M9 VLv2 |
| h5M9v9 | h5M9 VHv3 | h5M9 VLv3 |
| h5M9v10 | h5M9 VHv4 | h5M9 VLv1 |
| h5M9v11 | h5M9 VHv4 | h5M9 VLv2 |
| h5M9v12 | h5M9 VHv4 | h5M9 VLv3 |

TABLE 12-continued

| IgG number | HC number | LC number |
|---|---|---|
| h9D1v1 | h9D1 VHv1 | h9D1 VLv1 |
| h9D1v2 | h9D1 VHv1 | h9D1 VLv2 |
| h9D1v3 | h9D1 VHv1 | h9D1 VLv3 |
| h9D1v4 | h9D1 VHv2 | h9D1 VLv1 |
| h9D1v5 | h9D1 VHv2 | h9D1 VLv2 |
| h9D1v6 | h9D1 VHv2 | h9D1 VLv3 |
| h9D1v7 | h9D1 VHv3 | h9D1 VLv1 |
| h9D1v8 | h9D1 VHv3 | h9D1 VLv2 |
| h9D1v9 | h9D1 VHv3 | h9D1 VLv3 |

Example 10. Analysis of the Binding Activity of Humanized Antibody to Cell Surface hCLDN18.2

In this example, flow cytometry was used to determine the binding activity of 5-M9 and 9-D1 humanized antibodies to hCLDN18.2 on the cell surface. The well-grown HEK293-hCLDN18.2 stably transfected cell line and the hCLDN18.2 low-expressing KATOIII human gastric cancer cell line sorted and enriched by flow cytometry were digested with trypsin, and resuspended to adjust the cell concentration to $1.5\times10^{6}$~$2\times10^{6}$/mL, added to a 96-well U-plate at 100 μL/well (150,000 to 200,000 cells/well). Washing once with PBS buffer containing 1% fetal bovine serum (FBS). The antibody solution (100 μL/well) with the test concentration prepared in PBS (+1% FBS) was added, mixed with the cells, and incubated at 4° C. for 1 hour. Cells were centrifuged at 200 g and washed once with PBS (+1% FBS). Cy 3-Conjugated AffiniPure® goat anti-human IgG secondary antibody (Jackson labs, Cat. No. 109-165-003) diluted 1000 times in PBS (+1% FBS) or Alexa Fluor® 488-conjugated goat anti-human IgG (H+L) secondary antibody (Thermofisher, Cat. No. A-11013) was added at 100 L/well, mixed with cells and incubated at 4° C. for 45 minutes. Cells were centrifuged at 200 g and washed twice with PBS (+1% FBS), then resuspended in 100 μL of PBS (+1% FBS) for flow cytometric analysis. In the preliminary FACS binding analysis of 12 humanized molecules of 5-M9, the antibody expression supernatant of HEK293 cells was used, and the antibody concentration in the supernatant was quantified by Problife and corrected by ELISA. In the study of the effect of heat treatment on the binding properties of antibodies, the antibody to be tested was heat-treated at 70° C. for 5 minutes on a PCR machine, and then incubated with cells for binding. In a study to evaluate the non-specificity of humanized antibodies to polysaccharides, lipids and proteins, the ELISA method was used to detect the effect of antibodies on the binding ability of insect baculovirus (BV) (Hotzel et al, mAbs, 2012, 4 (6), 753-760). Insect virus envelopes contained many lipids, polysaccharides and proteins, and had biochemical mixture characteristics similar to those of human cells and tissues. The binding ability of antibodies to insect baculoviruses could evaluate the risk of non-specific binding of antibodies in vivo to a certain extent. Insect baculovirus was obtained by infecting insect cells with baculovirus plasmid. Insect baculovirus was diluted 1:500 with PBS, and was coated on a 96-well plate overnight at 4° C. at 50 μL/well. The plate was washed three times with PBS (300 μL/well), blocked with 1% BSA (200 μL/well) for 1 hour at room temperature, and the plate was washed three times with PBS. Antibodies at different concentrations (100 μL/well) were added and incubated at room temperature for 1 hour. The plate was washed 6 times with PBS (300 μL/well). 1:5000 diluted HRP-conjugated goat anti-human secondary antibody (100 μL/well) was added. After incubation at room temperature for 1 hour, the plate was washed 6 times with PBS (300 μL/well). H2O2-Amplx (100 μL/well) was added and the value was read at room temperature in the dark.

Table 13 showed the binding characteristics of 5-M9 humanized antibody expression supernatant to HEK293-hCLDN18.2 after non-heat treatment/heat treatment, in which h5M9V7, h5M9V10 and h5M9V12 had high binding activities in all 12 humanized molecules, and the stable binding characteristics were still maintained after the antibody was heat-treated at 70° C. for 5 minutes.

| | Heavy chain variable region | Light chain variable region |
|---|---|---|
| h5M9V7 | QVQLKESGPGLVAPSETLSITCTVSGF<br>SLTTYGVQWVRQPPGKGLEWLGAIW<br>AGGNTNYNSALMSRLTISKDNSKSQV<br>SLKMSSVTAADTAIYYCAKGGYGNA<br>MDYWGQGTLVTVSS<br>(SEQ ID NO: 34) | DIVMTQSPSSLAVSLGERATMNC<br>KSSQSLLNSGNQKNYLTWYQQK<br>PGQPPKLLIYWASTRESGVPDRF<br>SGSGSGTDFTLTISSVQAEDLAV<br>YYCQNDYFFPFTFGQGTKLEIK<br>(SEQ ID NO: 35) |
| h5M9V10 | QVQLKESGPGLVAPSETLSITCTVSGF<br>SLTTYGVQWVRQPPGKGLEWLGAIW<br>AGGNTNYNSALMSRLTISKDNSKSQV<br>SLKMSSLTAADTAIYYCAKGGYGNA<br>MDYWGQGTLVTVSS<br>(SEQ ID NO: 36) | DIVMTQSPSSLAVSLGERATMNC<br>KSSQSLLNSGNQKNYLTWYQQK<br>PGQPPKLLIYWASTRESGVPDRF<br>SGSGSGTDFTLTISSVQAEDLAV<br>YYCQNDYFFPFTFGQGTKLEIK<br>(SEQ ID NO: 35) |
| h5M9V12 | QVQLKESGPGLVAPSETLSITCTVSGF<br>SLTTYGVQWVRQPPGKGLEWLGAIW<br>AGGNTNYNSALMSRLTISKDNSKSQV<br>SLKMSSLTAADTAIYYCAKGGYGNA<br>MDYWGQGTLVTVSS<br>(SEQ ID NO: 36) | DIVMTQSPSSLAVSLGERVTMNC<br>KSSQSLLNSGNQKNYLTWYQQK<br>PGQPPKLLIYWASTRESGVPDRF<br>TGSGSGTDFTLTISSVQAEDLAV<br>YYCQNDYFFPFTFGSGTKLEIK<br>(SEQ ID NO: 37) |

The amino acid sequences of the heavy chain constant region and light chain constant region of h5M9V7, h5M9V10 and h5M9V12 were shown below:

| | |
|---|---|
| Heavy chain constant region | ASTKGPSVFPLAPSSKSTSGGTAALGCLVKDYFPEPVTVSWN SGALTSGVHTFPAVLQSSGLYSLSSVVTVPSSSLGTQTYICNVN HKPSNTKVDKKVEPKSCDKTHTCPPCPAPELLGGPSVFLFPPKP KDTLMISRTPEVTCVVVDVSHEDPEVKFNWYVDGVEVHNAK TKPREEQYNSTYRVVSVLTVLHQDWLNGKEYKCKVSNKALP APIEKTISKAKGQPREPQVYTLPPSRDELTKNQVSLTCLVKGFY PSDIAVEWESNGQPENNYKTTPPVLDSDGSFFLYSKLTVDKSR WQQGNVFSCSVMHEALHNHYTQKSLSLSPG (SEQ ID NO: 38) |
| Light chain constant region | RTVAAPSVFIFPPSDEQLKSGTASVVCLLNNFYPREAKVQW KVDNALQSGNSQESVTEQDSKDSTYSLSSTLTLSKADYEKHK VYACEVTHQGLSSPVTKSFNRGEC (SEQ ID NO: 39) |

Figure 19:
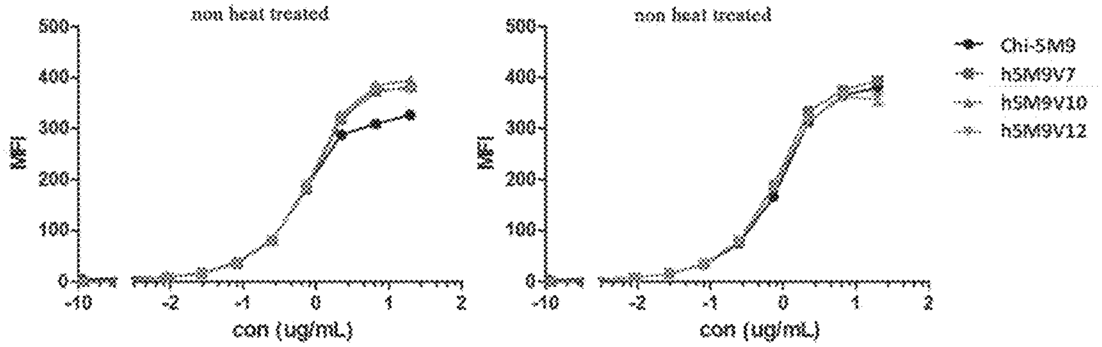
FIG. 19. Binding of 5-M9 chimeric antibody and humanized antibody to HEK293-hCLDN18.2 after non-heat treatment/heat treatment.
Figure 20:
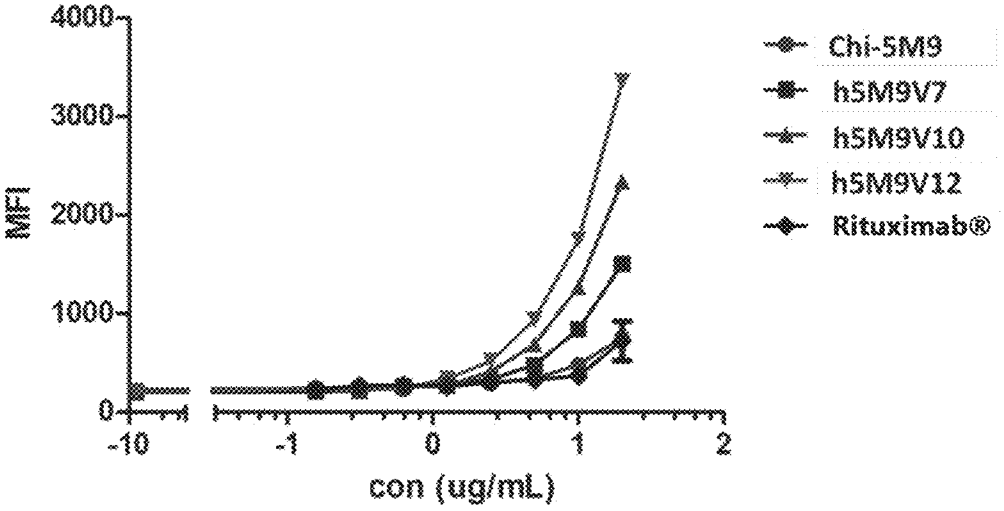
FIG. 20. Non-specific binding of 5-M9 chimeric antibody and humanized antibody to insect baculovirus.

The binding characteristics of purified antibodies of 5-M9 chimeric antibody (Chi 5-M9), h5M9V7, h5M9V10 and h5M9V12 (also known as: h5M9-V7, h5M9-V10 and h5M9-V12, respectively) to HEK293-hCLDN18.2 after non-heat/heat treatment were shown in FIG. 19, and the purified humanized antibodies h5M9V7, h5M9V10 and h5M9V12 had similar binding characteristics to the Chi 5-M9 antibody. The binding characteristics of the three humanized molecules after heat treatment at 70° C. were consistent with Chi 5-M9 and did not exhibit thermal instability. In a study to assess the risk of non-specific binding of 5-M9 and its humanized antibodies, as shown in FIG. 20, compared to the reference control (Rituxan®) and Chi 5-M9 antibody, the humanized antibody exhibited relatively enhanced non-specific binding at high concentrations, in which h5M9V7 showed the weakest non-specific binding.

Figure 21:
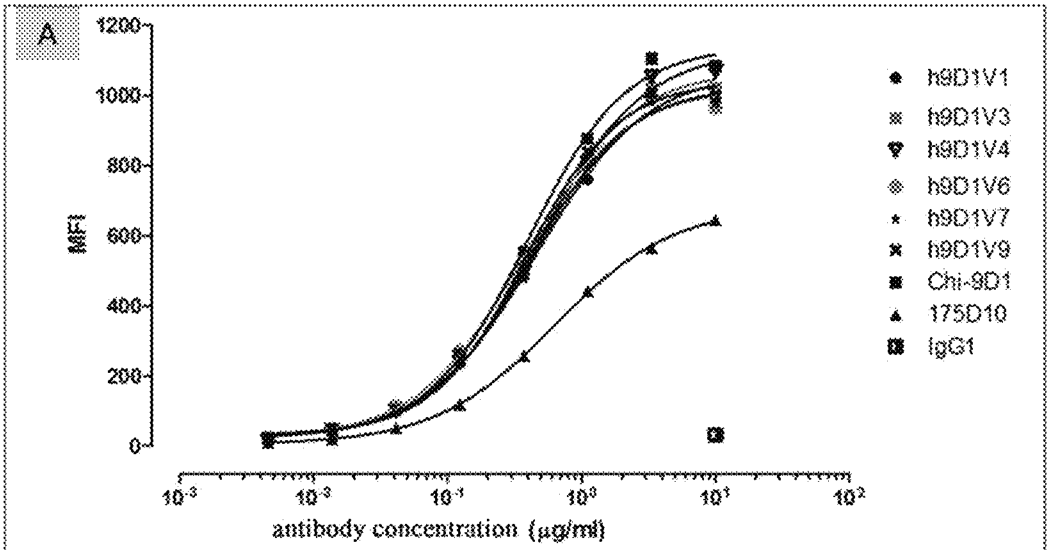
FIG. 21. Binding of 9-D1 and its humanized antibody to hCLDN18.2 low-expressing gastric tumor cell line KATO III.
Figure 21:
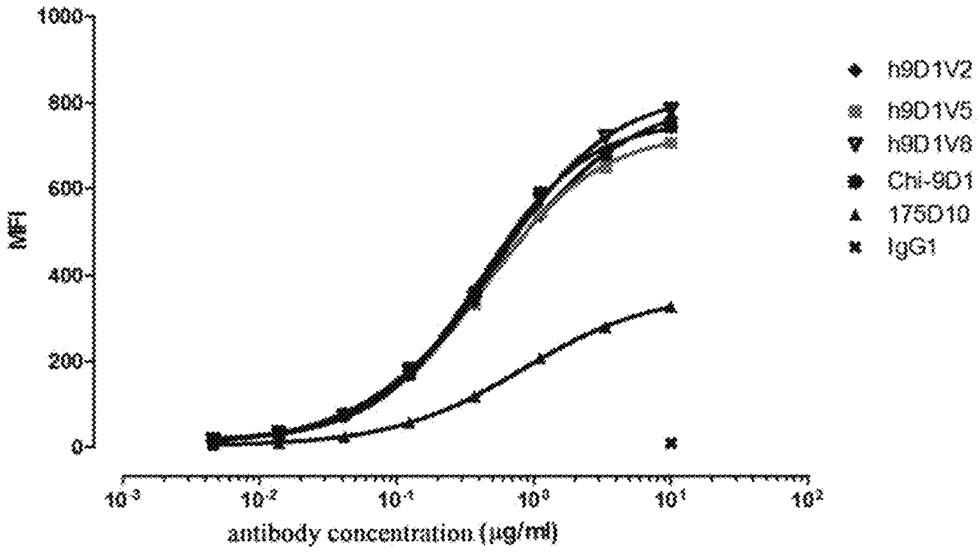
Figure 21:
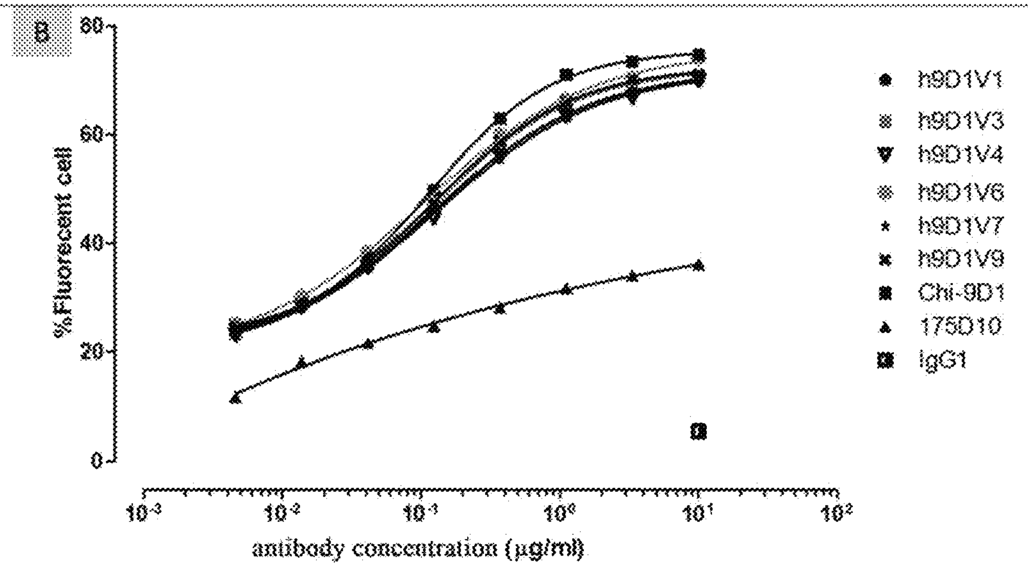
Figure 21:
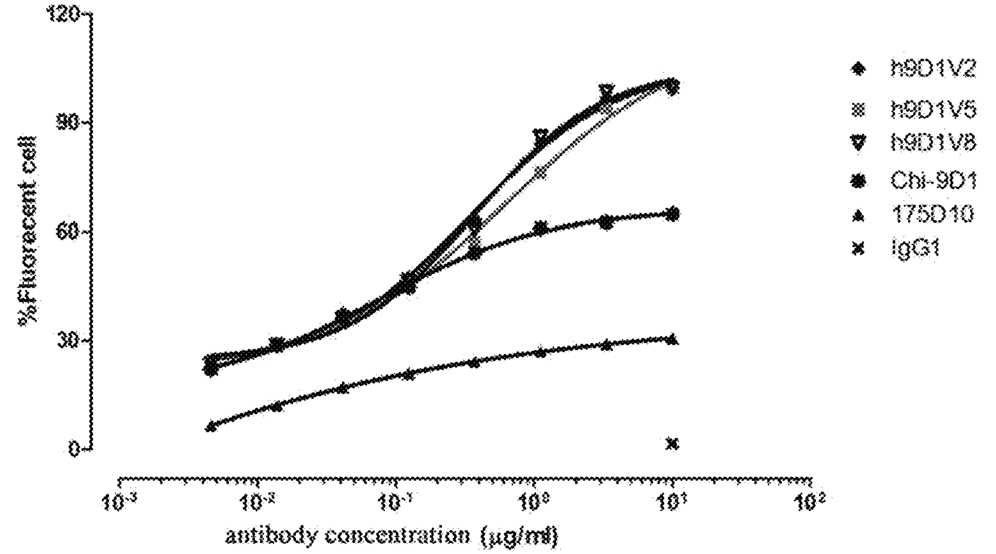

The binding properties of the tested antibody on the hCLDN18.2 low-expressing cell line were valuable for evaluating the clinical application of the antibody, because the expression level of CLDN18.2 in gastric tumors of patients was not uniform in clinical practice, and nearly ⅓ was low-level expression, and a single tumor expression was heterogeneous (Zhu G. et al, Sci Rep, 2019, 9, 8420-8431). FIG. 21 showed the binding of 9-D1 and its humanized antibodies to hCLDN18.2 low-expressing gastric tumor cell line KATO III. The binding of 9-D1 and its humanized molecules to KATO III was similar, and both showed strong binding capacity (FIG. 21, A), EC50 (0.4~ 0.5 μg/mL) was only half that of the positive control (Benchmark) 175D10 (about 0.8 μg/mL), and the maximum binding strength (800~1000 MFI) was twice that of 175D10 (300~600 MFI). The maximum positive cell rate (80%-95%) of 9-D1 and its humanized molecules bound to KATO III was twice that of the positive control 175D10 (30%-40%) (Figure. 21, B).

Example 11. Analysis of Physicochemical Properties of Humanized Antibodies

In this example, various methods were used to analyze the physicochemical properties of 5-M9 and 9-D1 and their humanized antibody molecules for their thermal stability, aggregate formation and purity.

Antibody thermal stability analysis: Differential scanning fluorescence (DSF) and static light scanning (SLS) were analyzed on Uncle™ system (UNCCHAINED LABS®), the temperature detection range of DSF and SLS was from 20° C. to 95° C., the heating rate was 1° C./minutes, the static light scattering at wavelengths 266 nm and 473 nm was detected, and the melting temperature (Tm) and thermal aggregation (Tagg) were analyzed by Uncle system software. Differential scanning calorimetry (DLC) detection instrument was Malvern® MicroCal® VP-Capillary DSC. The variable temperature range was from 25° C. to 100° C., and the scanning speed was 1° C./minutes. Scanning with test sample buffer as a blank solution. Raw data were processed by MicroCal VP-Capillary DSC Automated Analysis software.

Antibody aggregate analysis: dynamic light scattering (DLS) was performed on Uncle system, the test temperature was 25° C., and analysis was performed by Uncle system software. Size-Exclusion Chromatography (SEC) detection instrument was Waters™ Alliance™ e2695 system equipped with PDA detector. The column was TOSOH TSKgel® G3000SWXL, Cat. No. 0008541. The mobile phase was 0.1M phosphate buffer, 0.1M sodium chloride, pH 6.8. Flow rate was 1.0 mL/minutes, isocratic elution. The column temperature was 25° C., the detection wavelength was 280 nm, and the injection volume was 100 μg.

TABLE 13

| Antibody concentration (μg/mL) | Chi 5-M9 | h5M9 V1 | h5M9 V2 | h5M9 V3 | h5M9 V4 | h5M9 V5 | h5M9 V6 | h5M9 V7 | h5M9 V8 | h5M9 V9 | h5M9 V10 | h5M9 V11 | h5M9 V12 | 175D 10 PC |
|---|---|---|---|---|---|---|---|---|---|---|---|---|---|---|
| Not heat treated | | | | | | | | | | | | | | |
| 5 | 638 | 578 | 120 | 460 | 574 | 617 | 622 | 631 | 650 | 589 | 599 | 329 | 589 | 567 |
| 1 | 341 | 235 | 0 | 184 | 243 | 222 | 254 | 296 | 257 | 291 | 316 | 169 | 419 | 318 |
| 0.2 | 83 | 66.2 | 65.1 | 51.2 | 67.6 | 61 | 67.7 | 84.3 | 58 | 66.8 | 73.7 | 41 | 103 | 81.3 |
| 0 | 18.1 | 12.2 | 12.9 | / | / | / | / | / | / | / | | / | | / |
| heat treatment at 70° C. | | | | | | | | | | | | | | |
| 5 | 746 | 603 | 629 | 273 | 600 | 629 | 649 | 732 | 667 | 636 | 607 | 282 | 673 | 600 |
| 1 | 289 | 237 | 226 | 127 | 237 | 213 | 242 | 294 | 243 | 242 | 292 | 143 | 411 | 296 |
| 0.2 | 75.6 | 62.2 | 60 | 39.7 | 62.1 | 55.7 | 62.3 | 73.3 | 57.8 | 59.2 | 70.8 | 43.3 | 90 | 73 |
| 0 | 18.1 | 12.2 | 12.9 | / | / | / | / | / | / | / | | / | | / |

Figure 22:
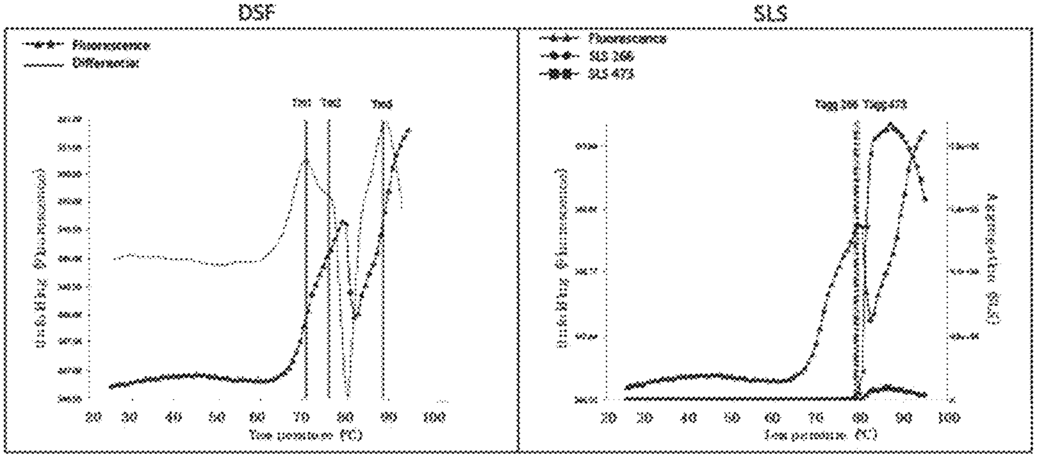
FIG. 22. DSF and SLS patterns of humanized antibody h5M9V7.

IgG antibodies had multiple protein domains, each of which had a unique melting temperature (Tm). The heavy chain constant region 2 (CH2) generally had a Tm of about 70° C. in PBS solution, and the heavy chain constant region 3 (CH3) was relatively stable with a Tm of about 80° C. Antibody Fabs region had a wide range of Tm about 50° C. to 85° C. due to the large sequence differences. However, the Tm of each domain was transitional, and sometimes the domains might not be separated because the Tm values of the domains were close. Table 14 showed the thermal stability analysis results of 5-M9 and its humanized antibodies. Each antibody has 2 or 3 Tm, wherein Tm1 was about 70° C., which should be the Tm of the CH2 domain; Tm2 or Tm3 was the Tm of CH3 or Fab domain; generally h5M9V7 had a higher Tm value (FIG. 22) and higher thermal stability. Tagg was the temperature starting point at which static light scattering could begin to detect the appearance of aggregates, wherein Tagg 266 nm measured the SLS at 266 nm, which was sensitive to the detection of small aggregate particles; Tagg 473 nm measured the SLS at 473 nm, which was sensitive to the detection of large aggregates. Tagg 266 nm and Tagg 473 nm of h5M9V7 were significantly higher than that of other humanized antibodies and 5-M9 chimeric antibody (FIG. 22).

TABLE 14

| | DSF (° C.) | | | SLS (° C.) | |
|---|---|---|---|---|---|
| Sample | $T_m1$ | $T_m2$ | $T_m3$ | $T_{agg}266$ nm | $T_{agg}473$ nm |
| Chi 5-M9 | 70.7 | 84.3 | N/A | 73.4 | 74.3 |
| h5M9V7 | 70.8 | 76.1 | 88.8 | 78.6 | 79.2 |
| h5M9V10 | 70.5 | 75.3 | 87.0 | 76.6 | 77.1 |
| h5M9V12 | 71.1 | 85.0 | N/A | 75.0 | 75.9 |

Figure 23:
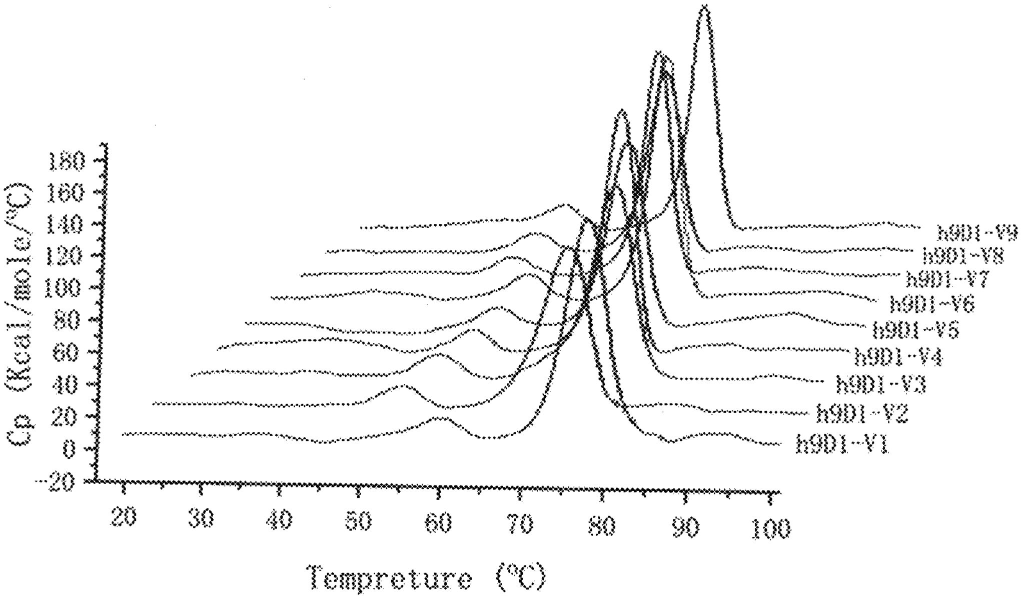
FIG. 23. DSC scan pattern of 9-D1 humanized antibody.

The differential scanning calorimetry (DSC) detection patterns of the 9-D1 antibody and its humanized antibody were shown in FIG. 23, and the corresponding melting temperatures (Tm values) were shown in Table 15. The results showed that each candidate antibody exhibited good thermal stability. As for the Tm1 value that could indicate the thermal stability of the CH2 region of the antibody, all the candidate antibodies were >50° C. As for the Tm2 value that could indicate the thermal stability of the Fab region of the antibody, all the candidate antibodies were >65° C. h9D1V1 had a significantly higher Tm value than other humanized antibodies, Tm1 was at least 5° C. higher than that of other humanized antibodies, and Tm2 was at least 3° C. higher than that of other humanized antibodies, indicating that compared with other 9-D1, the humanized antibody h9D1V1 had obvious thermal stability advantages.

TABLE 15

| Antibody name | Tm1 (° C.) | Tm2 (° C.) |
|---|---|---|
| h9D1_V1 | 61.1 | 77.6 |
| h9D1_V2 | 53.5 | 72.8 |
| h9D1_V3 | 54.5 | 75.2 |
| h9D1_V4 | 55.7 | 73.2 |
| h9D1_V5 | 55.3 | 71.2 |
| h9D1_V6 | 56.2 | 73.3 |
| h9D1_V7 | 51.4 | 69.7 |
| h9D1_V8 | 51.4 | 68.1 |
| h9D1_V9 | 52.1 | 70.2 |

The aggregate analysis of the 5-M9 humanized antibody adopted the dynamic light scattering (DLS) method, and the DLS data was summarized in Table 16. The particle radius of each antibody molecule at 25° C. was about 9.5 nm (peak 1), which conformed to the radius range of antibody monomer, was IgG monomer molecule, and the content % was about 100%. The polydispersity index (PDI) reflects the dispersity of the particles, and PDI<0.25 can be considered as a single homogeneous particle. PDI for both h5M9V7 and h5M9V12 were less than 0.25 and significantly smaller than Chi 5-M9 and h5M9V10, indicating that they had good monomer dispersion and were not easy to form aggregate.

Figure 24:
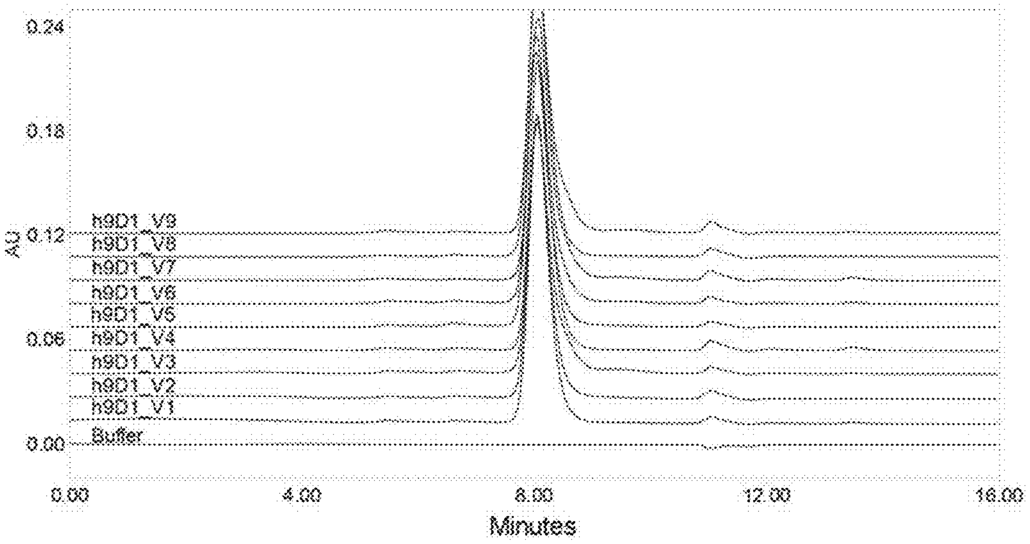
FIG. 24. SEC pattern of the 9-D1 humanized antibody molecule.

The aggregate of 9-D1 humanized antibody were analyzed by size exclusion chromatography (SEC). The SEC detection pattern was shown in FIG. 24. It could be seen that each humanized antibody of 9-D1 had good monomer purity, and no apparent aggregates and fragmented fragments appeared. Wherein, the main peaks of h9D1V3, h9D1V6, h9D1V7 and h9D1V9 antibodies were slightly tailed. The main peak shape of h9D1V1 was the best without any tailing phenomenon.

TABLE 16

| | Peak 1 | | | Peak 2 | |
|---|---|---|---|---|---|
| Sample | hydraulic radius (nm) | content (%) | PDI | hydraulic radius (nm) | quality content (%) |
| Chi 5-M9 | 9.62 | 100 | 1.052 | 354.96 | 0 |
| h5M9V7 | 9.68 | 100 | 0.227 | N/A | 0 |
| h5M9V10 | 9.68 | 99.98 | 1.406 | 157.90 | 0 |
| h5M9V12 | 9.62 | 100 | 0.142 | N/A | 0 |

Figure 25:
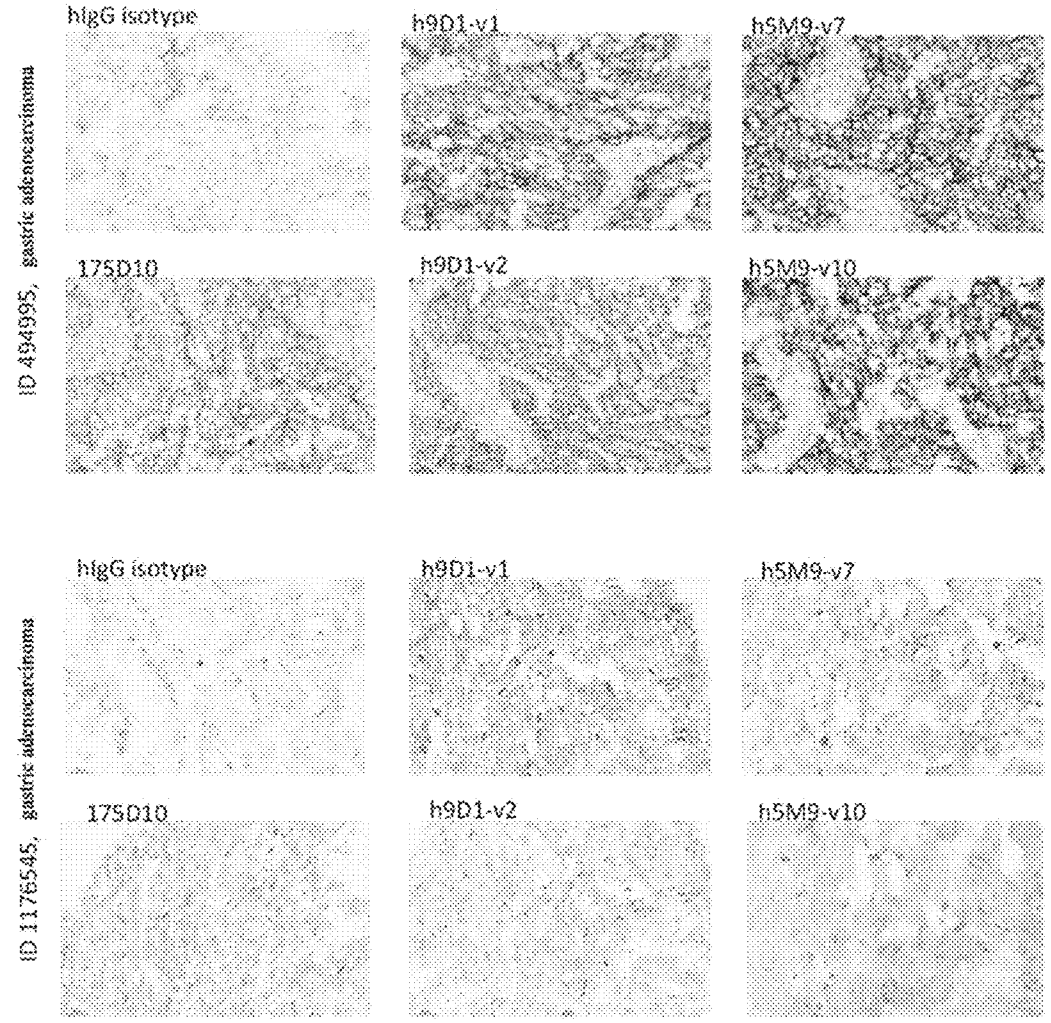
FIG. 25. IHC staining of 9-D1 and 5M9 humanized antibodies on frozen sections of gastric cancer.
Figure 25:
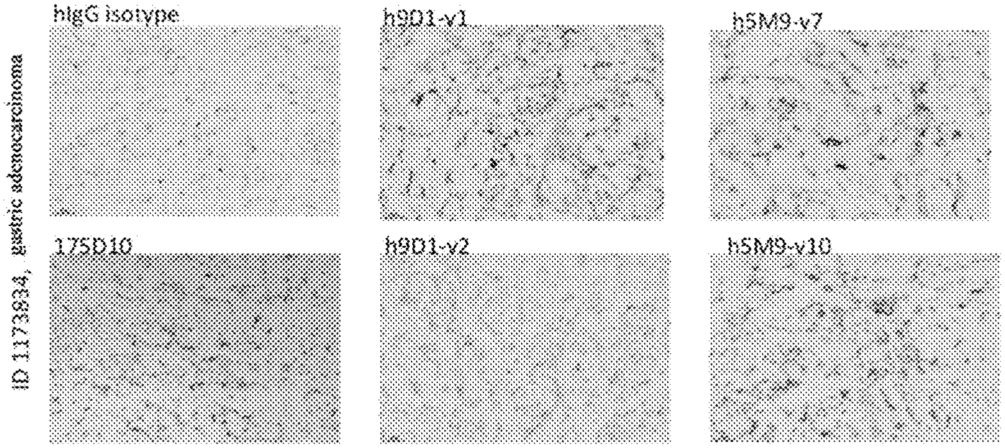
Figure 25:
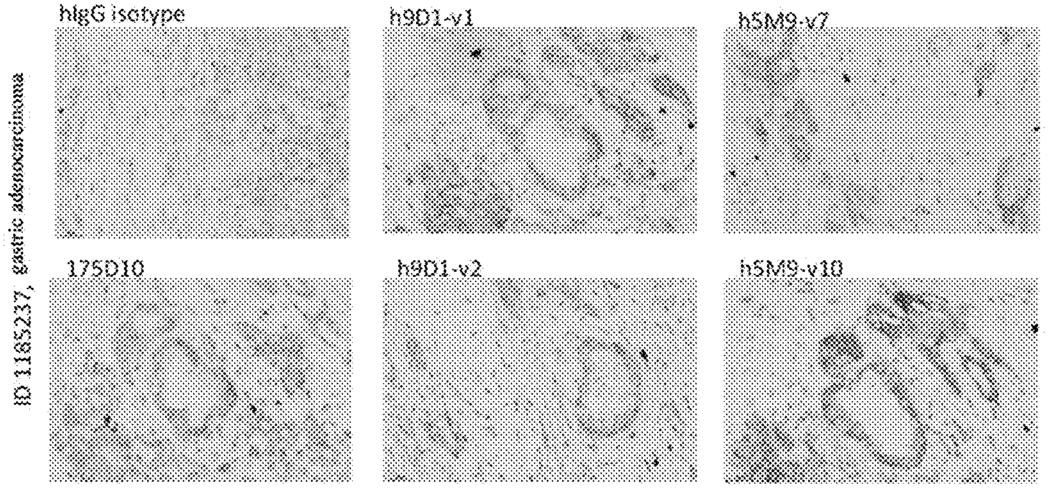

Example 12. IHC Staining of Humanized Antibody on Gastric Cancer Tissues and Normal Human Major Organ Tissues In this example, purified 9D1 and 5M9 humanized antibodies were used, and the antibodies were directly conjugated with poly-HRP-polymer (WO2015171938), and then immunohistochemistry was used to detect humanized antibodies staining on frozen sections of 16 gastric cancer tissues and 5 normal human major organ (heart, liver, spleen, lung, and kidney, 3 for each tissue) tissues. Poly-HRP-polymer-conjugated hIgG isotype Antibody (ThermoFisher, Cat. No. 12000C) was used as the negative control, and Poly-HRP-polymer-conjugated 175D10 antibody was used as the reference antibody (Benchmark). The immunohistochemical method was as follows, frozen tissue sections were fixed with frozen acetone for 5 minutes, then inactivated with 3% $H_2O_2$ PBS buffer for 5 minutes, washed with PBS, and incubated with 5 μg/mL Poly-HRP-polymer antibody conjugate for 5 minutes. The sections were washed with PBS, and the reaction was terminated after 3 minutes of DAB substrate color development, and photographed with a microscope. Table 17 summarized the IHC staining results of 9D1 and 5M9 humanized antibodies on frozen sections of 16 cases of gastric cancer, showing that the staining results of the negative control (hIgG isotype antibody) were negative on all tissues, and the positive staining rate of the reference antibody (Benchmark) 175D10 was 31.3% (~5/16), while the positive staining rates of h9D1-V1, h9D1-V2, h5M9-V7 and h5M9-V10 were significantly higher than those of the reference antibody 175D10, reaching 75% (12⁄16), 62.5% (10⁄16), 75% (12⁄16) and 81.25% (13⁄16), and the staining intensity of humanized 9D1 and 5M9 antibodies was significantly stronger than that of 175D10 in positively stained tissues (as shown in FIG. 25).

The following were the amino acid sequences of the heavy chain variable region and light chain variable region of h9D1-V1 and h9D1-V2 (also known as h9D1V1 and h9D1V2). Their heavy chain constant region sequences and light chain constant region sequences were SEQ ID NO: 38 and SEQ ID NO: 39, respectively.

| | Heavy chain variable region | Light chain variable region |
|---|---|---|
| h9D1-V1 | QIQLVQSGAEVKKPGASV<br>KISCKASGYSFTDYHMN<br>WVRQAPGKGLEWIGNIDP<br>YYGSPTYNHKFKGRVTLT<br>VDTSTSTAYMELSSLRSED<br>TAVYYCANYGRGNSFPY<br>WGQGTLVTVSS<br>(SEQ ID NO: 40) | DIVMTQSPSSLAVSLGERA<br>TINCKSSQSLLNSGNQRN<br>YLTWYQQKPGQPPKLLIY<br>WASTRESGVPDRFSGSGS<br>GTDFTLTISSLQAEDVAVY<br>YCQNDYSFPFTFGQGTKL<br>EIK<br>(SEQ ID NO: 41) |
| h9D1-V2 | QIQLVQSGAEVKKPGASV<br>KISCKASGYSFTDYHMN<br>WVRQAPGKGLEWIGNIDP<br>YYGSPTYNHKFKGRVTLT<br>VDTSTSTAYMELSSLRSED<br>TAVYYCANYGRGNSFPY<br>WGQGTLVTVSS<br>(SEQ ID NO: 40) | DIVMTQSPSSLAVSLGERA<br>TINCKSSQSLLNSGNQRN<br>YLTWYQQKPGQPPKLLLY<br>WASTRESGVPDRFSGSGS<br>GTDFTLTISSLQAEDLAVY<br>YCQNDYSFPFTFGQGTKL<br>EIK<br>(SEQ ID NO: 42) |

TABLE 18

| | Organs diagnosis | | | | |
|---|---|---|---|---|---|
| | Heart (3 cases) normal | Lung (3 cases) normal | spleen (3 cases) normal | kidney (3 cases) normal | liver (3 cases) normal |
| hIgG1 isotype antibody | – | – | – | – | – |
| 175D10 | – | – | – | – | – |
| h9D1-V2 | – | – | – | – | – |
| h9D1-V1 | – | – | – | – | – |
| h5M9-V7 | – | – | – | – | – |
| h5M9-V10 | – | – | – | – | – |

The above results showed that, compared to the reference antibody (Benchmark) 175D10 antibody, the humanized 9D1 and 5M9 antibodies had significantly improved specific positive staining rate and staining intensity on gastric cancer tissues, and did not have nonspecific tissue cross-reactivity on non-targeted major organ tissues. This suggested the high druggability properties of 9D1 and 5M9 antibodies, which maximized tumor targeting without off-target toxicity.

Example 13. Anti-Tumor Effect of Antibody on Tumor-Bearing Mice

This example studies the anti-tumor effects of h9DIVI antibody and positive control antibody 175D10 on tumor-bearing mice. CB17-SCAD mice (Vitamin Lihua, strain code 404) were entered into the experimental animal breeding room, quarantined for 7 days, cell quarantined, and entered into the experiment after passing the test. The mice

TABLE 17

| Tissue number & diagnosis type | N00009 gastric adenocar-cinoma | N00010 gastric adenocar-cinoma | N00011 gastric adenocar-cinoma | N00012 gastric adenocar-cinoma | N00117 gastric adenocar-cinoma | N00118 gastric adenocar-cinoma | N00119 gastric adenocar-cinoma | 1181518 Gastric adenocar-cinoma well differentiated | 494995 Gastric adenocar-cinoma well differentiated |
|---|---|---|---|---|---|---|---|---|---|
| hIgG1 Isotype | – | – | – | – | – | – | – | – | – |
| 175D10 | – | – | – | – | + | – | + | – | + |
| h9D1-V1 | – | + | + | + | + | – | + | – | + |
| h9D1-V2 | – | + | + | + | + | – | + | – | + |
| h5M9-V7 | – | + | + | + | + | – | + | – | + |
| h5M9-V10 | – | + | + | + | + | – | + | + | + |

| Tissue number & diagnosis type | 1176545 gastric adenocar-cincoma moderately differentiated | 1185237 gastric adenocar-cincoma moderately differentiated | 1181742 gastric adenocar-cincoma moderately differentiated | 1171812 gastric adenocar-cincoma poorly differentiated | 1173834 gastric adenocar-cincoma poorly differentiated | 1181460 gastric adenocar-cincoma poorly differentiated | 1184192 gastric mucinous cell carcinoma |
|---|---|---|---|---|---|---|---|
| hIgG1 Isotype | – | – | – | – | – | – | – |
| 175D10 | + | – | – | – | – | – | – |
| h9D1-V1 | + | + | – | – | + | + | – |
| h9D1-V2 | – | + | – | – | – | + | – |
| h5M9-V7 | + | + | – | – | + | + | – |
| h5M9-V10 | + | + | – | – | + | + | – |

Figure 26:
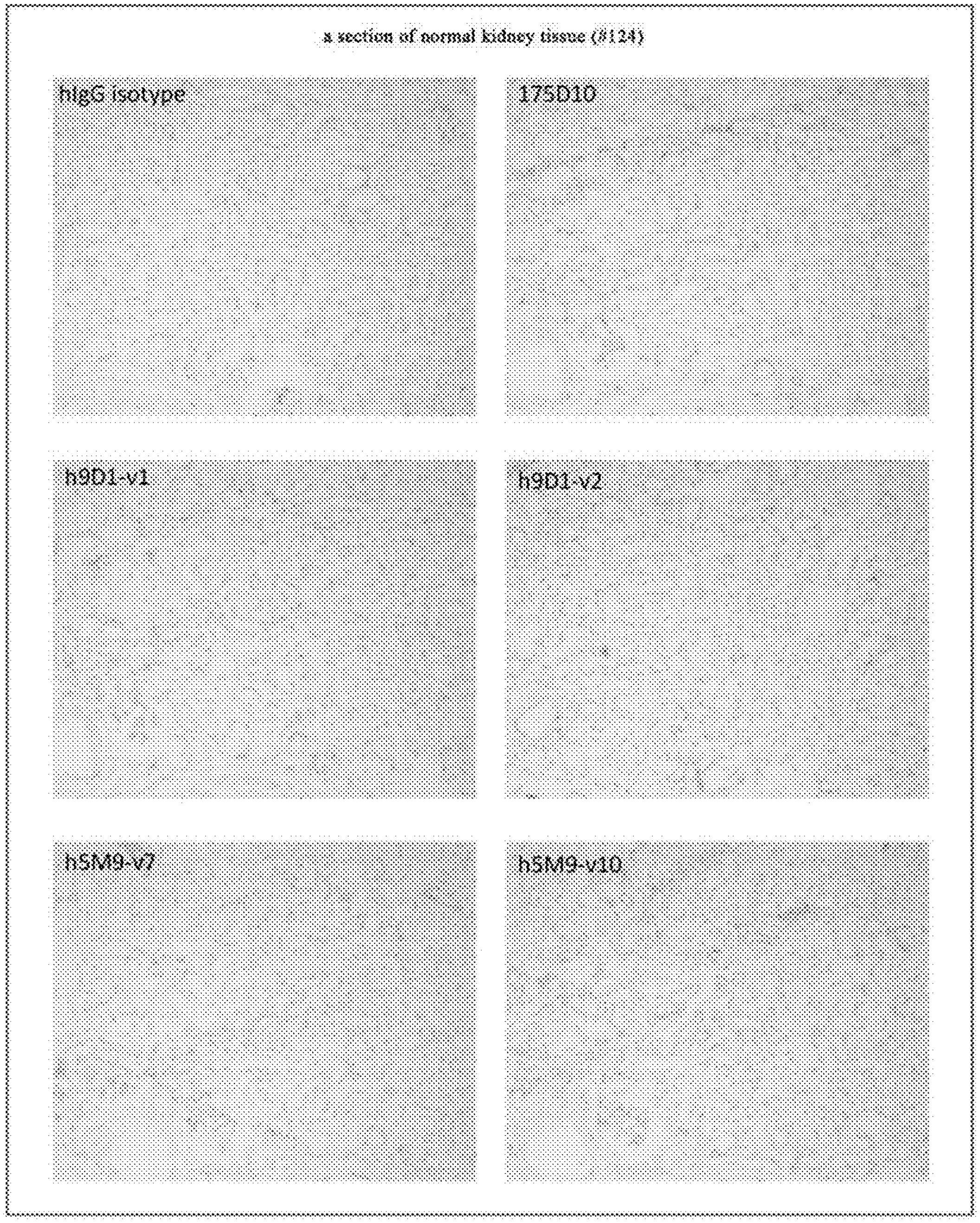
FIG. 26. IHC staining of 9-D1 and 5M9 humanized antibodies on normal human major organ tissues.
Figure 26:
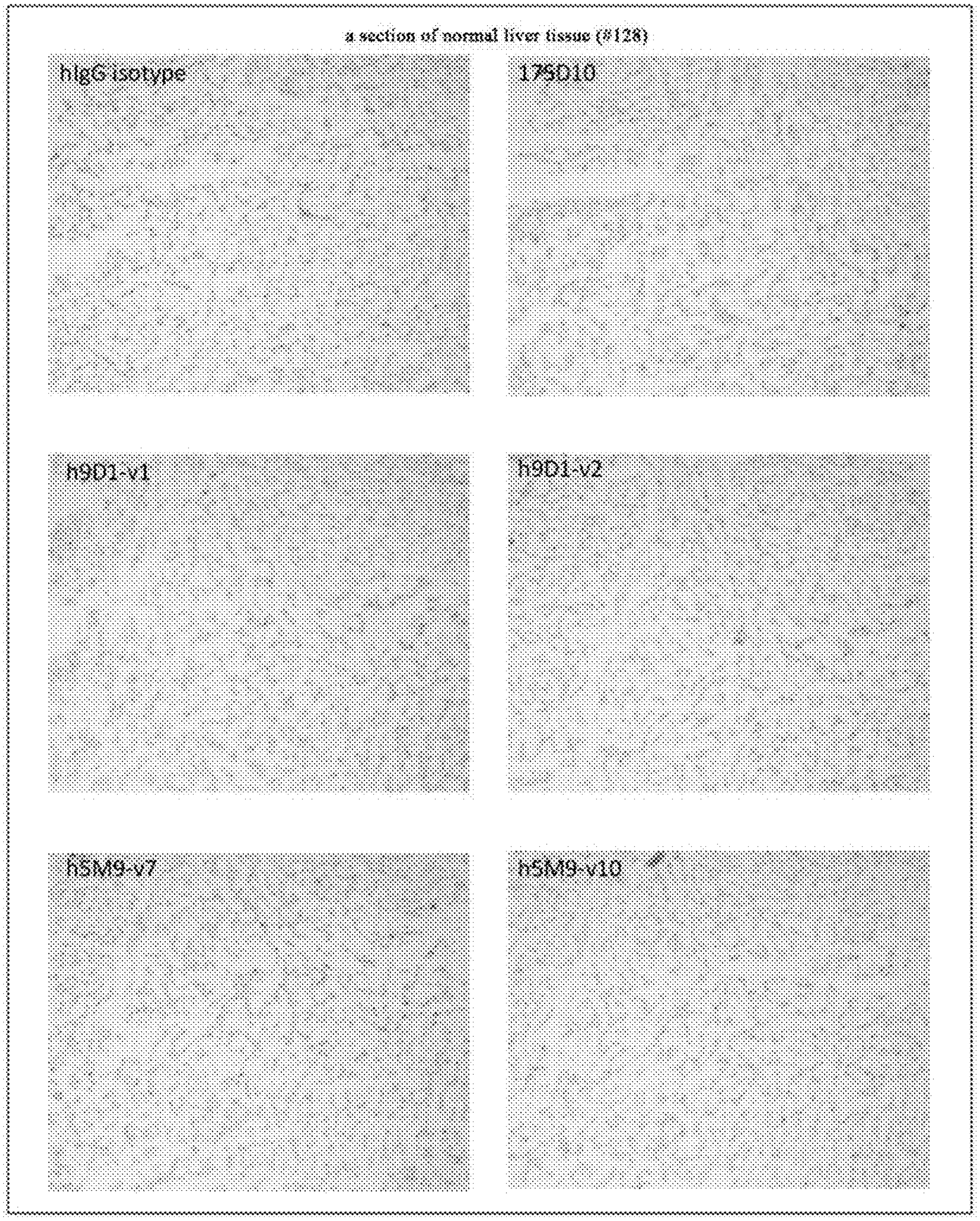
Figure 27:
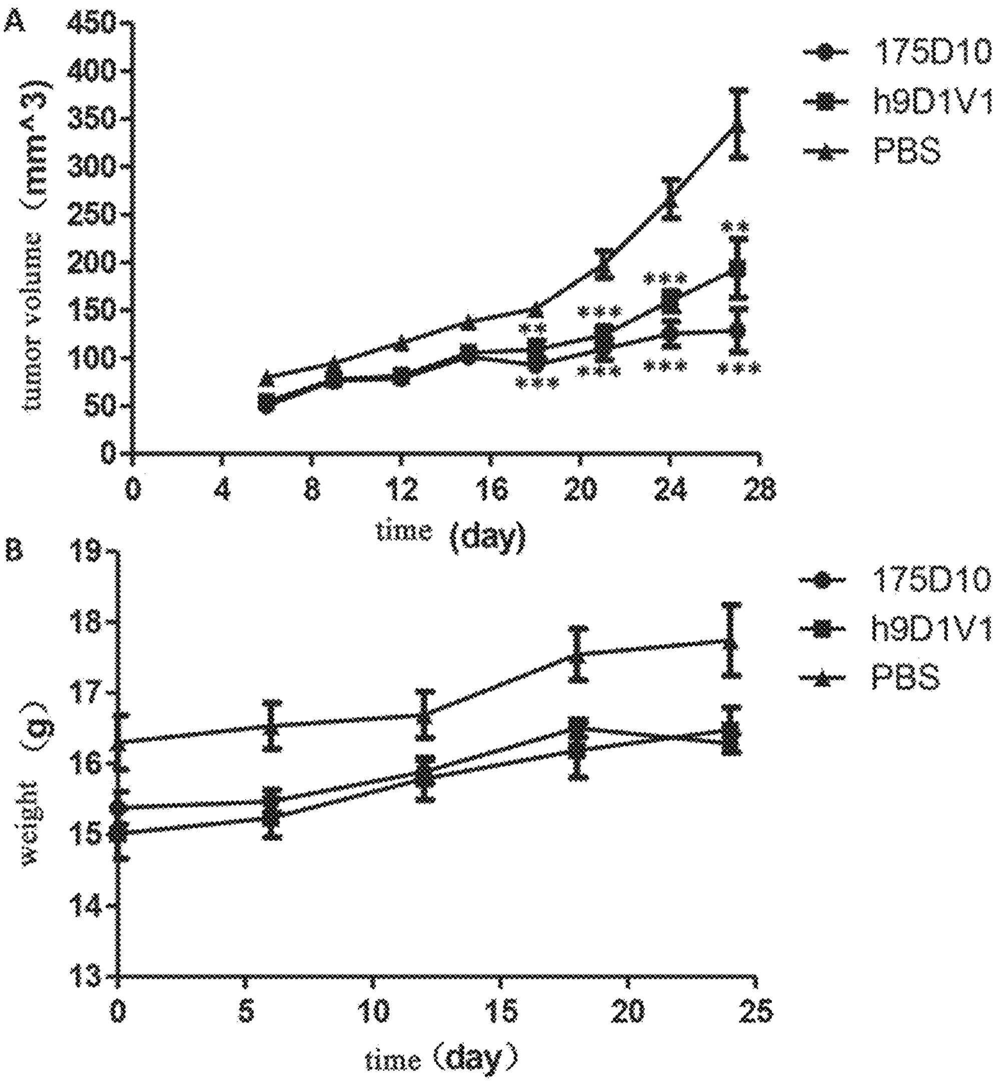
FIG. 27. Antitumor effect of 9-D1 humanized antibody on tumor-bearing mice.

The IHC staining results of 9D1 and 5M9 humanized antibodies and control antibodies on frozen sections of normal human heart (3 cases), liver (3 cases), spleen (3 cases), lung (3 cases) and kidney (3 cases) were summarized as follows as shown in Table 18, and all staining results were negative. FIG. 26 showed the negative staining results of antibodies on a normal kidney tissue (#125) and normal liver tissue (#128), respectively.

were inoculated with $5\times10^6$ HEK293-hCLDN18.2 cells with a volume of 100 μl (Matrigel® (Biocoat, Cat. No. 356234): PBS=1:1) in the middle of the flank, observed for 1 day, and on the second day after inoculation, randomly divided into three groups (PBS group, 175D10, h9D1V1), 9 animals in each group, and intraperitoneal administration (200 μg/mouse, administration concentration of 1 mg/mL, administration volume of 200 μL, twice a week for 4 weeks) was started. Tumor volume was measured one week after inoculation, and then every 3 days, and body weight was measured every 6 days once. One-way-ANOVA, Tukey post-hoc test was used for statistics, p<0.01, *p<0.001. The results were shown in FIG. 27. Compared with the PBS group, the 175D10 administration group could significantly inhibit tumor growth, and h9D1V1 could also significantly inhibit tumor growth. There was no significant difference between 175D10 and h9D1V1. During the administration period, the body weight of the mice showed the same trend, and there was no significant administration-related change.

Sequence Listing

SEQ ID NO: 1

```
Atggccgtgactgcctgtcagggcttggggttcgtggtttcactgattgggattgcgggcatcattgctgccacctgcatggaccagtgga
gcacccaagacttgtacaacaaccccgtaacagctgttttcaactaccaggggctgtggcgctcctgtgtccgagagagctctggcttcac
cgagtgccggggctacttcaccctgctggggctgccagccatgctgcaggcagtgcgagccctgatgatcgtaggcatcgtcctgggtg
ccattggcctcctggtatccatctttgccctgaaatgcatccgcattggcagcatggaggactctgccaaagccaacatgacactgacctcc
gggatcatgttcattgtctcaggtctttgtgcaattgctggagtgtctgtgtttgccaacatgctggtgactaacttctggatgtccacagctaa
catgtacaccggcatgggtgggatggtgcagactgttcagaccaggtacacatttggtgcggctctgttcgtgggctgggtcgctggagg
cctcacactaattggggtgtgatgatgtgcatcgcctgccggggcctggcaccagaagaaaccaactacaaagccgtttcttatcatgcc
tcaggccacagtgttgcctacaagcctggaggcttcaaggccagcactggctttgggtccaacaccaaaaacaagaagatatacgatgg
aggtgcccgcacagaggacgaggtacaatcttatccttccaagcacgactatgtgtaa
```

SEQ ID NO: 2

```
TQDLYNNPVTAVFNYQGLWRSCVRESSGFTECRGYFTLLGLPA
```

SEQ ID NO: 3

```
MDIDPYKEFGASVELLSFLPSDFFPSIRDLLDTASALYREALESPEHCSPHHTALRQAVLC
WGELMNLATWVGSNLEDGGGGSGGGGTQDLYNNPVTAVFNYQGLWRSCVRESSGFT
ECRGYFTLLGLPAGGGGSGGGGSRELVVSYVNINMGLKIRQLLWFHISCLTFGRETVLE
YLVSFGVWIRTPPAYRPPNAPILSTLPETTVVRGGSHHHHHH
```

SEQ ID NO: 4

```
Atggccgtgactgcctgtcagggcttggggttcgtggtttcactgattgggattgcgggcatcattgctgccacctgcatggaccagtgga
gcacccaagacttgtacaacaaccccgtaacagctgttttcaactaccaggggctgtggcgctcctgtgtccgagagagctctggcttcac
cgagtgccggggctacttcaccctgctggggctgccagccatgctgcaggcagtgcgagccctgatgatcgtaggcatcgtcctgggtg
ccattggcctcctggtatccatctttgccctgaaatgcatccgcattggcagcatggaggactctgccaaagccaacatgacactgacctcc
gggatcatgttcattgtctcaggtctttgtgcaattgctggagtgtctgtgtttgccaacatgctggtgactaacttctggatgtccacagctaa
catgtacaccggcatgggtgggatggtgcagactgttcagaccaggtacacatttggtgcggctctgttcgtgggctgggtcgctggagg
cctcacactaattggggtgtgatgatgtgcatcgcctgccggggcctggcaccagaagaaaccaactacaaagccgtttcttatcatgcc
tcgggccacagtgttgcctacaagcctggaggcttcaaggccagcactggctttgggtccaacaccaaaaacaagaagatatacgatgg
aggtgcccgcacagaggacgaggtacaatcttatccttccaagcacgactatgtgtaa
```

SEQ ID NO: 5

```
Atgtccaccaccacatgccaagtggtggcgttcctcctgtccatcctggggctggccggctgcatcgcggccaccgggatggacatgtg
gagcacccaggacctgtacgacaaccccgtcacctccgtgttccagtacgaagggctctggaggagctgcgtgaggcagagttcaggc
ttcaccgaatgcaggccctatttcaccatcctgggacttccagccatgctgcaggcagtgcgagccctgatgatcgtaggcatcgtcctgg
gtgccattggcctcctggtatccatctttgccctgaaatgcatccgcattggcagcatggaggactctgccaaagccaacatgacactgac
ctccgggatcatgttcattgtctcaggtctttgtgcaattgctggagtgtctgtgtttgccaacatgctggtgactaacttctggatgtccacag
ctaacatgtacaccggcatgggtgggatggtgcagactgttcagaccaggtacacatttggtgcggctctgttcgtgggctgggtcgctgg
aggcctcacactaattggggtgtgatgatgtgcatcgcctgccggggcctggcaccagaagaaaccaactacaaagccgtttcttatcat
gcctcaggccacagtgttgcctacaagcctggaggcttcaaggccagcactggctttgggtccaacaccaaaaacaagaagatatacga
tggaggtgcccgcacagaggacgaggtacaatcttatccttccaagcacgactatgtgtaa
```

SEQ ID NO: 6

```
Atgtcggtgaccgcctgccagggcttggggtttgtggtgtcactgatcgggtttgcgggcatcattgcagccacttgtatggaccagtgga
gcacccaggatttatacaacaacccggtgaccgctgtattcaactaccaagggctatggcgttcatgcgtccgagagagctctggcttcac
cgagtgccgaggctacttcaccctgttggggttgccagccatgctgcaagctgtacgagccctgatgatcgtgggcattgttctgggggtc
atcggtatcctcgtgtccatcttcgccctgaagtgcattcgcattggtagcatggatgactctgccaaggccaagatgactctgacttctggg
atcttgttcatcatctccggcatctgtgcaatcattggtgtgtctgtgtttgccaacatgctggtgaccaacttctggatgtccacagctaacatg
tacagcggcatgggcggcatgggtggcatggtgcagaccgttcagaccaggtacacctttggtgcagctctgttcgtgggctgggttgct
ggaggcctcaccctgattggggagtgatgatgtgcatcgcctgccgtggcctgacaccagatgacagcaacttcaaagctgtgtcttac
catgcctctggccaaaatgttgcctacaggcctggaggctttaaggccagcactggctttgggtccaacaccagaaacaagaagatctac
gatgggggtgcccgcacagaagacgatgaacagtctcatcctaccaagtatgactatgtgtag
```

SEQ ID NO: 7

```
Atggccaccaccacgtgccaggtggtagggcttctcctgtccctcctgggtctggccggctgcatagccgccactgggatggacatgtg
gagcactcaagacctgtatgacaacccagtcaccgccgtgttccagtatgaagggctctggaggagttgcgtgcaacagagctcggggt
tcaccgagtgccggccatacttcaccatcctgggccttccagccatgctgcaagctgtacgagccctgatgatcgtgggcattgttctggg
ggtcatcggtatcctcgtgtccatcttcgccctgaagtgcattcgcattggtagcatggatgactctgccaaggccaagatgactctgacttc
tgggatcttgttcatcatctccggcatctgtgcaatcattggtgtgtctgtgtttgccaacatgctggtgaccaacttctggatgtccacagcta
acatgtacagcggcatgggcggcatgggtggcatggtgcagaccgttcagaccaggtacacctttggtgcagctctgttcgtgggctgg
gttgctggaggcctcaccctgattggggagtgatgatgtgcatcgcctgccgtggcctgacaccagatgacagcaacttcaaagctgtg
tcttaccatgcctctggccaaaatgttgcctacaggcctggaggctttaaggccagcactggctttgggtccaacaccagaaacaagaaga
tctacgatgggggtgcccgcacagaagacgatgaacagtctcatcctaccaagtatgactatgtgtag
```

SEQ ID NO: 8

```
Atggaatggacctgggtctttctcttcctcctgtcagtaactgcaggtgtccactcccaggttcagctgcagcagtctggagctgagctgat
gaagcctggggcctcagtgaagatatcctgcaaggctactggctacacattcagtagctactggatagagtgggtaaagcagaggcctg
gacatggccttgagtggattggagagatttacctggaagtggtagtactaactacaatgagaagttcaagggcaaggccacattcactgc
agatacatcctccaacacagcctacatgcaactcagcagcctgacatctgaggactctgccgtctattactgtgcaagatatgattacccct
ggtttgcttactggggccaagggactctggtcactgtctctgcagcctctacaaagggcccagcgtgtttccactggctccctcctctaag
agcacaagcggcggcaccgctgccctgggctgtctggtgaaggactactttccagagcctgtgacagtgagctggaattccggcgctct
```

-continued

Sequence Listing gacctctggcgtgcacacctttccagccgtgctgcagtcttccggcctgtactccctgtctagcgtggtgaccgtgcccagctcctctctgg
gcacccagacatatatctgcaacgtgaatcacaagccttccaatacaaaggtggacaagaaggtggagccaaagtcctgtgacaagacc
catacatgcccccccatgtcctgctcccgagctgctgggcggcccttccgtgttcctgtttcccccaaagcccaaggataccctgatgatcag
cagaaccccagaggtgacatgcgtggtggtggacgtgtcccatgaggatcccgaggtgaagttcaactggtacgtggacggcgtggag
gtgcataacgccaagacaaagcctagagaggagcagtacaactccacctaccgggtggtgtccgtgctgaccgtgctgcaccaggact
ggctgaatggcaaggagtacaagtgcaaggtgtctaataaggccctgcctgctccaatcgagaagacaatctctaaggctaagggccag
cctcgggagccccaggtgtataccctgcctccatccagagacgagctgaccaagaatcaggtgtctctgacatgcctggtgaagggcttc
tatccatccgatatcgctgtggagtgggagagcaatggccagcctgagaacaattataagacaaccccacctgtgctggattctgacggc
agctttttcctgtattccaagctgaccgtggataagtctagatggcagcagggcaacgtgttctcctgtagcgtgatgcacgaggcactgca
taatcactacacccagaagtcactgtcactgagtccaggcaaataa

SEQ ID NO: 9

Atgcattttcaagtgcagattttcagcttcctgctaatcagtgcctcagtcataatgtccagaggacaaattgttctcacccagtctccagcaa
tcatgtctgcatctccaggggagaaggtcaccataacctgcagtgccagctcaagtgtaagttacatgcactggttccagcagaagccag
gcacttctcccaaactctggatttatagcacatccaacctggcttctggagtccctgctcgcttcagtggcagtggatctgggacctcttactc
tctcacaatcagccgaatggaggctgaagatgctgccacttattactgccagcaaaggagtagttacccacccacgttcggaggggggga
ccaagctggaaataaagagaaccgtggctgccccaagcgtgtttatcttccctccatctgatgagcagctgaagtctggcacagctagcgt
ggtgtgcctgctgaataacttctaccccagagaggccaaggtgcagtggaaggtggataacgctctgcagtctggcaactcccaggagt
ctgtgacagagcaggattccaaggacagcacatactccctgtctagcaccctgacactgagcaaggctgactacgagaagcacaaggtg
tacgcttgcgaggtcactcatcagggactgtcatctcctgtcactaagagttttaatcgcggcgagtgttga

SEQ ID NO: 10 atgggatggagctgtatcatcctcttcttggtagcaacagctacaggtgtccactcccaggtccaactgcagcagcctggggctgagctgg
tgaggcctggggcttcagtgaagctgtcctgcaaggcttctggctacaccttcaccagctactggataaactgggtgaagcagaggcctg
gacaaggccttgagtggatcggaaatatttatccttctgatagttatactaactacaatcaaaagttcaaggacaaggccacattgactgtag
acaaatcctccagcacagcctacatgcagctcagcagcccgacatctgaggactctgcggtctattactgtacaagatcgtggaggggta
actcctttgactactggggccaaggcaccactctcacagtctcctcagcctctacaaagggccccagcgtgtttccactggctccctcctct
aagagcacaagcggcggcaccgctgccctgggctgtctggtgaaggactactttccagagcctgtgacagtgagctggaattccggcg
ctctgacctctggcgtgcacacctttccagccgtgctgcagtcttccggcctgtactccctgtctagcgtggtgaccgtgcccagctcctctc
tgggcacccagacatatatctgcaacgtgaatcacaagccttccaatacaaaggtggacaagaaggtggagccaaagtcctgtgacaag
acccatacatgcccccccatgtcctgctcccgagctgctgggcggcccttccgtgttcctgtttcccccaaagcccaaggataccctgatgat
cagcagaaccccagaggtgacatgcgtggtggtggacgtgtcccatgaggatcccgaggtgaagttcaactggtacgtggacggcgtg
gaggtgcataacgccaagacaaagcctagagaggagcagtacaactccacctaccgggtggtgtccgtgctgaccgtgctgcaccagg
actggctgaatggcaaggagtacaagtgcaaggtgtctaataaggccctgcctgctccaatcgagaagacaatctctaaggctaagggc
cagcctcgggagccccaggtgtataccctgcctccatccagagacgagctgaccaagaatcaggtgtctctgacatgcctggtgaaggg
cttctatccatccgatatcgctgtggagtgggagagcaatggccagcctgagaacaattataagacaaccccacctgtgctggattctgac
ggcagctttttcctgtattccaagctgaccgtggataagtctagatggcagcagggcaacgtgttctcctgtagcgtgatgcacgaggcact
gcataatcactacacccagaagtcactgtcactgagtccaggcaaataa

SEQ ID NO: 11

Atggaatcacagactcaggtcctcatgtccctgctgttctgggtatctggtacctgtggggacattgtgatgacacagtctccatcctccctg
actgtgacagcaggagagaaggtcactatgagctgcaagtccagtcagagtctgttaaacagtggaaatcaaaagaactacttgacctgg
taccagcagaaaccagggcagcctcctaaactgttgatctactgggcatccactagggaatctggggtccctgatcgcttcacaggcagt
ggatctggaacagatttcactctcaccatcagcagtgtgcaggctgaagacctggcagtttattactgtcagaatgattatagttatccattca
cgttcggctcggggacaaagttggaaataaagagaaccgtggctgccccaagcgtgtttatcttccctccatctgatgagcagctgaagtc
tggcacagctagcgtggtgtgcctgctgaataacttctaccccagagaggccaaggtgcagtggaaggtggataacgctctgcagtctgg
caactcccaggagtctgtgacagagcaggattccaaggacagcacatactccctgtctagcaccctgacactgagcaaggctgactacg
agaagcacaaggtgtacgcttgcgaggtcactcatcagggactgtcatctcctgtcactaagagttttaatcgcggcgagtgttga

SEQ ID NO: 12 atggattggctgtggaacttgctattcctgatggcagctgcccaaagtatccaagcacagatccagttggtgcagtctggacctgagctgaa
gaagcctggagagacagtcaagatctcctgcaaggcttctgggtataccttcacaaactatggaatgaactgggtgaagcaggctccagg
aaagggtttaaagtggatgggctggataaacaccaacactggagagccaacatatgctgaagagttcaagggacggtttgccttctctttg
gaaacctctgccagcactgcctatttgcagatcaacaacctcaaaaatgaggacacggctacatatttctgtgcaagactgggttttggtaat
gctatggactactggggtcaaggaacctcagtcaccgtctcctcagcctctacaaagggccccagcgtgtttccactggctccctcctctaa
gagcacaagcggcggcaccgctgccctgggctgtctggtgaaggactactttccagagcctgtgacagtgagctggaattccggcgctc
tgacctctggcgtgcacacctttccagccgtgctgcagtcttccggcctgtactccctgtctagcgtggtgaccgtgcccagctcctctctgg
gcacccagacatatatctgcaacgtgaatcacaagccttccaatacaaaggtggacaagaaggtggagccaaagtcctgtgacaagacc
catacatgcccccccatgtcctgctcccgagctgctgggcggcccttccgtgttcctgtttcccccaaagcccaaggataccctgatgatcag
cagaaccccagaggtgacatgcgtggtggtggacgtgtcccatgaggatcccgaggtgaagttcaactggtacgtggacggcgtggag
gtgcataacgccaagacaaagcctagagaggagcagtacaactccacctaccgggtggtgtccgtgctgaccgtgctgcaccaggact
ggctgaatggcaaggagtacaagtgcaaggtgtctaataaggccctgcctgctccaatcgagaagacaatctctaaggctaagggccag
cctcgggagccccaggtgtataccctgcctccatccagagacgagctgaccaagaatcaggtgtctctgacatgcctggtgaagggcttc
tatccatccgatatcgctgtggagtgggagagcaatggccagcctgagaacaattataagacaaccccacctgtgctggattctgacggc
agctttttcctgtattccaagctgaccgtggataagtctagatggcagcagggcaacgtgttctcctgtagcgtgatgcacgaggcactgca
taatcactacacccagaagtcactgtcactgagtccaggcaaataa

SEQ ID NO: 13 atggaatcacagactcaggtcctcatgtccctgctgttctgggtatctggtacctgtggggacattgtgatgacacagtctccatcctccctg
actgtgacagcaggagagaaggtcactatgagctgcaagtccagtcagagtctgttaaacagtggaaatcaaaagaactacttgacctgg
taccagcagaaaccagggcagcctcctaaactgttgatctactgggcatccactagggaatctggggtccctgatcgcttcacaggcagt
ggatctggaacagatttcactctcaccatcagcagtgtgcaggctgaagacctggcagtttattactgtcagaatgattatagttatccgctca
cgttcggtgctgggaccaagctggagctgaagagaaccgtggctgccccaagcgtgtttatcttccctccatctgatgagcagctgaagtc
tggcacagctagcgtggtgtgcctgctgaataacttctaccccagagaggccaaggtgcagtggaaggtggataacgctctgcagtctgg
caactcccaggagtctgtgacagagcaggattccaaggacagcacatactccctgtctagcaccctgacactgagcaaggctgactacg
agaagcacaaggtgtacgcttgcgaggtcactcatcagggactgtcatctcctgtcactaagagttttaatcgcggcgagtgttga -continued

| Sequence Listing |
|---|

SEQ ID NO: 14
CAGGTACAGCTGAAGGAGTCAGGACCTGTCCTGGTGGCGCCCTCACAGAGCCTGTC
CATCACTTGCACTGTCTCTGGGTTTTCATTAACCACCTATGGTGTACAGTGGGTTCGC
CAGCCTCCAGGAAAGGGTCTGGAGTGGCTGGGAGCAATATGGGCTGGTGGAAACA
CAAATTATAATTCAGCTCTCATGTCCAGACTGAGCATCAGCAAAGACAACTCCAAGA
GCCAAGTTTTCTTAAAAATGAACAGTCTGCAAACTGATGACACAGCCATATACTACT
GTGCCAAAGGGGGTTACGGGAATGCTATGGACTACTGGGGTCAAGGAACCTCAGTC
ACCGTCGCCTCA

SEQ ID NO: 15
GAGATCCAGCTGCAGCAGTCTGGAGCTGAGCTGGTGAAGCCTGGGGCTTCAGTGAA
GATATCCTGCAAGGCTTCTGGTTATTCATTCACTGACTACCACATGAACTGGGTGAGG
CAGAGCCATGGAAAGAGCCTTGAGTGGATTGGAAATATTGATCCTTACTATGGTAGT
CCTACCTACAATCATAAATTCAAGGGCAAGGCCACATTGACTGTAGACAAATCTTCC
AGCACAGCCTACATGCAGCTCATCAGCCTGACATCTGAGGACTCTGCAGTCTATTAC
TGTGCAAACTACGGAAGGGGAAATTCGTTTCCTTACTGGGGCCAAGGGACTCTGGT
CACTGTCTCTGCA

SEQ ID NO: 16
GACATTGTGATGACACAGTCTCCATCCTCCCTGACTGTGACAGCAGGAGAGAGGGT
CACTATGAGCTGCAAGTCCAGTCAGAGTCTGTTAAACAGTGGAAATCAAAAGAACT
ACTTGACCTGGTACCAACAGAAATCAGGGCAGCCTCCTAAATTGTTGATCTACTGGG
CATCCACTAGGGAATCTGGGGTCCCTGATCGCTTCACAGGCAGTGGATCTGGAACAG
ATTTCACTCTCACCATCAGCAGTGTGCAGGCTGAAGACCTGGCAGTTTATTACTGTC
AGAATGATTATTTTTTTCCATTCACGTTCGGCTCGGGGACAAAGTTGGAAATAAAA

SEQ ID NO: 17
GACATTGTGATGACACAGTCTCCATCCTCCCTGACTGTGACAGCAGGAGAGAAGGT
CACTATGAGCTGCAAGTCCAGTCAGAGTCTGTTAAACAGTGGAAATCAAAGGAACT
ACTTGACCTGGTACCAGCAGAAACCAGGGCAGCCTCCTAAACTGTTACTCTACTGG
GCATCCACTAGGGAATCTGGGGTCCCTGATCGCTTCACAGGCAGTGGATCTGGAACA
GATTTCACTCTCACCATCAGCAGTGTGCAGGCTGAAGACCTGGCAGTTTATTACTGT
CAGAATGATTATAGTTTTCCATTCACGTTCGGCTCGGGGACAAAGTTGGAAATAAAA

SEQ ID NO: 18
GFSLTTY

SEQ ID NO: 19
WAGGN

SEQ ID NO: 20
GGYGNAMDY

SEQ ID NO: 21
GYSFTDY

SEQ ID NO: 22
DPYYGS

SEQ ID NO: 23
YGRGNSFPY

SEQ ID NO: 24
KSSQSLLNSGNQKNYLT

SEQ ID NO: 25
WASTRES

SEQ ID NO: 26
QNDYFFPFT

SEQ ID NO: 27
KSSQSLLNSGNQRNYLT

SEQ ID NO: 28
WASTRES

SEQ ID NO: 29
QNDYSFPFT

SEQ ID NO: 30
QVQLKESGPVLVAPSQSLSITCTVSGFSLTTYGVQWVRQPPGKGLEWLGAIWAGGNTN
YNSALMSRLSISKDNSKSQVFLKMNSLQTDDTAIYYCAKGGYGNAMDYWGQGTSVT
VAS

| Sequence Listing |
|---|

SEQ ID NO: 31
EIQLQQSGAELVKPGASVKISCKASGYSFTDYHMNWVRQSHGKSLEWIGNIDPYYGSP
TYNHKFKGKATLTVDKSSSTAYMQLISLTSEDSAVYYCANYGRGNSFPYWGQGTLVT
VSA

SEQ ID NO: 32
DIVMTQSPSSLTVTAGERVTMSCKSSQSLLNSGNQKNYLTWYQQKSGQPPKLLIYWAS
TRESGVPDRFTGSGSGTDFTLTISSVQAEDLAVYYCQNDYFFPFTFGSGTKLEIK

SEQ ID NO: 33
DIVMTQSPSSLTVTAGEKVTMSCKSSQSLLNSGNQRNYLTWYQQKPGQPPKLLLYWA
STRESGVPDRFTGSGSGTDFTLTISSVQAEDLAVYYCQNDYSFPFTFGSGTKLEIK

SEQ ID NO: 34
QVQLKESGPGLVAPSETLSITCTVSGFSLTTYGVQWVRQPPGKGLEWLGAIWAGGNTN
YNSALMSRLTISKDNSKSQVSLKMSSVTAADTAIYYCAKGGYGNAMDYWGQGTLVTV
SS

SEQ ID NO: 35
DIVMTQSPSSLAVSLGERATMNCKSSQSLLNSGNQKNYLTWYQQKPGQPPKLLIYWAS
TRESGVPDRFSGSGSGTDFTLTISSVQAEDLAVYYCQNDYFFPFTFGQGTKLEIK

SEQ ID NO: 36
QVQLKESGPGLVAPSETLSITCTVSGFSLTTYGVQWVRQPPGKGLEWLGAIWAGGNTN
YNSALMSRLTISKDNSKSQVSLKMSSLTAADTAIYYCAKGGYGNAMDYWGQGTLVTV
SS

SEQ ID NO: 37
DIVMTQSPSSLAVSLGERVTMNCKSSQSLLNSGNQKNYLTWYQQKPGQPPKLLIYWAS
TRESGVPDRFTGSGSGTDFTLTISSVQAEDLAVYYCQNDYFFPFTFGSGTKLEIK

SEQ ID NO: 38
ASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKKVEPKSCDKTHTCPPCPAPELLG
GPSVFLFPPKPKDTLMISRTPEVTCVVVDVSHEDPEVKFNWYVDGVEVHNAKTKPREE
QYNSTYRVVSVLTVLHQDWLNGKEYKCKVSNKALPAPIEKTISKAKGQPREPQVYTLP
PSRDELTKNQVSLTCLVKGFYPSDIAVEWESNGQPENNYKTTPPVLDSDGSFFLYSKLTV
DKSRWQQGNVFSCSVMHEALHNHYTQKSLSLSPG

SEQ ID NO: 39
RTVAAPSVFIFPPSDEQLKSGTASVVCLLNNFYPREAKVQWKVDNALQSGNSQESVTEQ
DSKDSTYSLSSTLTLSKADYEKHKVYACEVTHQGLSSPVTKSFNRGEC

SEQ ID NO: 40
QIQLVQSGAEVKKPGASVKISCKASGYSFTDYHMNWVRQAPGKGLEWIGNIDPYYGSP
TYNHKFKGRVTLTVDTSTSTAYMELSSLRSEDTAVYYCANYGRGNSFPYWGQGTLVTV
SS

SEQ ID NO: 41
DIVMTQSPSSLAVSLGERATINCKSSQSLLNSGNQRNYLTWYQQKPGQPPKLLIYWAST
RESGVPDRFSGSGSGTDFTLTISSLQAEDVAVYYCQNDYSFPFTFGQGTKLEIK

SEQ ID NO: 42
DIVMTQSPSSLAVSLGERATINCKSSQSLLNSGNQRNYLTWYQQKPGQPPKLLLYWAST
RESGVPDRFSGSGSGTDFTLTISSLQAEDLAVYYCQNDYSFPFTFGQGTKLEIK

SEQ ID NO: 43
QVQLKESGPVLVAPSQSLSITCTVS

SEQ ID NO: 44
GVQWVRQPPGKGLEWLGAI

SEQ ID NO: 45
TNYNSALMSRLSISKDNSKSQVFLKMNSLQTDDTAIYYCAK

SEQ ID NO: 46
WGQGTSVTVAS

SEQ ID NO: 47
EIQLQQSGAELVKPGASVKISCKAS

SEQ ID NO: 48
HMNWVRQSHGKSLEWIGNI

SEQ ID NO: 49
PTYNHKFKGKATLTVDKSSSTAYMQLISLTSEDSAVYYCAN

-continued

| Sequence Listing |
|---|
| SEQ ID NO: 50<br>WGQGTLVTVSA |
| SEQ ID NO: 51<br>DIVMTQSPSSLTVTAGERVTMSC |
| SEQ ID NO: 52<br>WYQQKSGQPPKLLIY |
| SEQ ID NO: 53<br>GVPDRFTGSGSGTDFTLTISSVQAEDLAVYYC |
| SEQ ID NO: 54<br>FGSGTKLEIK |
| SEQ ID NO: 55<br>DIVMTQSPSSLTVTAGEKVTMSC |
| SEQ ID NO: 56<br>WYQQKPGQPPKLLLY |
| SEQ ID NO: 57<br>GVPDRFTGSGSGTDFTLTISSVQAEDLAVYYC |
| SEQ ID NO: 58<br>FGSGTKLEIK |

The invention claimed is:

1. A claudin 18.2 (CLDN18.2) antibody comprising a binding domain comprising:

(a) heavy chain CDRs comprising: CDR1 comprising the amino acid sequence as shown by SEQ ID NO:18, CDR2 comprising the amino acid sequence as shown by SEQ ID NO: 19, and CDR3 comprising the amino acid sequence as shown by SEQ ID NO:20; and light chain CDRs comprising: CDR1 comprising the amino acid sequence as shown by SEQ ID NO:24, CDR2 comprising the amino acid sequence as shown by SEQ ID NO:25, and CDR3 comprising the amino acid sequence as shown by SEQ ID NO: 26; or (b) heavy chain CDRs comprising:

CDR1 comprising the amino acid sequence as shown by SEQ ID NO:21, CDR2 comprising the amino acid sequence as shown by SEQ ID NO:22, and CDR3 comprising the amino acid sequence as shown by SEQ ID NO:23; and light chain CDRs comprising:

CDR1 comprising the amino acid sequence as shown by SEQ ID NO:27, CDR2 comprising the amino acid sequence as shown by SEQ ID NO:28, and CDR3 comprising the amino acid sequence as shown by SEQ ID NO:29.

2. The CLDN18.2 antibody of claim 1, comprising a heavy chain variable region as shown by SEQ ID NO:30, SEQ ID NO:31, SEQ ID NO:34, SEQ ID NO:36, or SEQ ID NO:40.

3. The CLDN18.2 antibody of claim 1, comprising a light chain variable region as shown by SEQ ID NO:32, SEQ ID NO:33, SEQ ID NO:35, SEQ ID NO: 37, SEQ ID NO:41, or SEQ ID NO:42.

4. The CLDN18.2 antibody of claim 1, comprising a heavy chain variable region and a light chain variable region, wherein:

1) The heavy chain variable region is shown by SEQ ID NO:30 and the light chain variable region is shown by SEQ ID NO:32; or 2) The heavy chain variable region is shown by SEQ ID NO:31 and the light chain variable region is shown by SEQ ID NO:33.

5. The CLDN18.2 antibody of claim 1, comprising a heavy chain variable region and a light chain variable region, wherein:

1) The heavy chain variable region is shown by SEQ ID NO:34 and the light chain variable region is shown by SEQ ID NO:35;

2) The heavy chain variable region is shown by SEQ ID NO:36 and the light chain variable region is shown by SEQ ID NO:35;

3) The heavy chain variable region is shown by SEQ ID NO:36 and the light chain variable region is shown by SEQ ID NO:37;

4) The heavy chain variable region is shown by SEQ ID NO:40 and the light chain variable region is shown by SEQ ID NO:41; or 5) The heavy chain variable region is shown by SEQ ID NO:40 and the light chain variable region is shown by SEQ ID NO:42.

6. The CLDN18.2 antibody of claim 1, which is a chimeric antibody, a humanized antibody, or a fully human antibody.

7. The CLDN18.2 antibody of claim 1, wherein the antibody is a full-length antibody.

8. The CLDN18.2 antibody of claim 7, which is an IgG antibody.

9. The CLDN18.2 antibody of claim 1, wherein the antibody is a Fab, a Fab'-SH, a Fv, scFv or a $(Fab')_2$.

10. The CLDN18.2 antibody of claim 1, which is a multispecific antibody or a bispecific antibody.

11. The CLDN18.2 antibody of claim 10, wherein the multispecific antibody or the bispecific antibody binds a cell surface antigen.

12. The CLDN18.2 antibody of claim 11, wherein the cell surface antigen is selected from the group consisting of: CD3, CD20, FcRH5, HER2, LYPD1, LY6G6D, PMEL17, LY6E, CD19, CD33, CD22, CD79A, CD79B, EDAR, GFRA1, MRP4, RET, Steap1, and TenB2.

13. An immunoconjugate, comprising a therapeutic agent, a stimulating factor for interferon gene (STING) receptor agonist, a cytokine, a radionuclide, or an enzyme linked to the CLDN18.2 antibody of claim 1.

14. The immunoconjugate of claim 13, wherein the therapeutic agent is a chemotherapeutic drug or a cytotoxic agent.

15. A fusion protein or polypeptide comprising the CLDN18.2 antibody of claim 1.

16. A pharmaceutical composition comprising the CLDN18.2 antibody of claim 1.

17. An isolated nucleic acid comprising a polynucleotide sequence encoding the CLDN18.2 antibody of claim 1.

18. A vector, comprising the polynucleotide sequence of claim 17.

19. A host cell, comprising the polynucleotide sequence of claim 17.

20. A method for preparing a CLDN18.2 antibody, comprising culturing the host cell of claim 19 under conditions for the expression of the antibody and isolating the antibody produced by the host cell from the culture.

* * * * *

SEQUENCE LISTING

<160> NUMBER OF SEQ ID NOS: 65

<210> SEQ ID NO 1
<211> LENGTH: 786
<212> TYPE: DNA
<213> ORGANISM: Artificial Sequence
<220> FEATURE:
<223> OTHER INFORMATION: Description of Artificial Sequence:
artificially synthesized sequence

<400> SEQUENCE: 1
atggccgtga ctgcctgtca gggcttgggg ttcgtggttt cactgattgg gattgcgggc 60
atcattgctg ccacctgcat ggaccagtgg agcacccaag acttgtacaa caaccccgta 120
acagctgttt tcaactacca ggggctgtgg cgctcctgtg tccgagagag ctctggcttc 180
accgagtgcc ggggctactt caccctgctg gggctgccag ccatgctgca ggcagtgcga 240
gccctgatga tcgtaggcat cgtcctgggt gccattggcc tcctggtatc catctttgcc 300
ctgaaatgca tccgcattgg cagcatggag gactctgcca aagccaacat gacactgacc 360
tccgggatca tgttcattgt ctcaggtctt tgtgcaattg ctggagtgtc tgtgtttgcc 420
aacatgctgg tgactaactt ctggatgtcc acagctaaca tgtacaccgg catgggtggg 480
atggtgcaga ctgttcagac caggtacaca tttggtgcgg ctctgttcgt gggctgggtc 540
gctggaggcc tcacactaat tgggggtgtg atgatgtgca tcgcctgccg gggcctggca 600
ccagaagaaa ccaactacaa agccgtttct tatcatgcct caggccacag tgttgcctac 660
aagcctggag gcttcaaggc cagcactggc tttgggtcca acaccaaaaa caagaagata 720
tacgatggag gtgcccgcac agaggacgag gtacaatctt atccttccaa gcacgactat 780
gtgtaa 786

<210> SEQ ID NO 2
<211> LENGTH: 43
<212> TYPE: PRT

<213> ORGANISM: Artificial Sequence
<220> FEATURE:
<223> OTHER INFORMATION: Description of Artificial Sequence:
      artificially synthesized sequence

<400> SEQUENCE: 2

```
Thr Gln Asp Leu Tyr Asn Asn Pro Val Thr Ala Val Phe Asn Tyr Gln
1               5                   10                  15

Gly Leu Trp Arg Ser Cys Val Arg Glu Ser Ser Gly Phe Thr Glu Cys
            20                  25                  30

Arg Gly Tyr Phe Thr Leu Leu Gly Leu Pro Ala
        35                  40
```

<210> SEQ ID NO 3
<211> LENGTH: 218
<212> TYPE: PRT
<213> ORGANISM: Artificial Sequence
<220> FEATURE:
<223> OTHER INFORMATION: Description of Artificial Sequence:
      artificially synthesized sequence

<400> SEQUENCE: 3

```
Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Val Leu Cys Trp Gly Glu
    50                  55                  60

Leu Met Asn Leu Ala Thr Trp Val Gly Ser Asn Leu Glu Asp Gly Gly
65                  70                  75                  80

Gly Gly Ser Gly Gly Gly Gly Thr Gln Asp Leu Tyr Asn Asn Pro Val
                85                  90                  95

Thr Ala Val Phe Asn Tyr Gln Gly Leu Trp Arg Ser Cys Val Arg Glu
            100                 105                 110

Ser Ser Gly Phe Thr Glu Cys Arg Gly Tyr Phe Thr Leu Leu Gly Leu
        115                 120                 125

Pro Ala Gly Gly Gly Gly Ser Gly Gly Gly Gly Ser Arg Glu Leu Val
    130                 135                 140

Val Ser Tyr Val Asn Ile Asn Met Gly Leu Lys Ile Arg Gln Leu Leu
145                 150                 155                 160

Trp Phe His Ile Ser Cys Leu Thr Phe Gly Arg Glu Thr Val Leu Glu
                165                 170                 175

Tyr Leu Val Ser Phe Gly Val Trp Ile Arg Thr Pro Pro Ala Tyr Arg
            180                 185                 190

Pro Pro Asn Ala Pro Ile Leu Ser Thr Leu Pro Glu Thr Thr Val Val
        195                 200                 205

Arg Gly Gly Ser His His His His His His
    210                 215
```

<210> SEQ ID NO 4
<211> LENGTH: 786
<212> TYPE: DNA
<213> ORGANISM: Artificial Sequence
<220> FEATURE:
<223> OTHER INFORMATION: Description of Artificial Sequence:
      artificially synthesized sequence

<400> SEQUENCE: 4

```
atggccgtga ctgcctgtca gggcttgggg ttcgtggttt cactgattgg gattgcgggc     60

atcattgctg ccacctgcat ggaccagtgg agcacccaag acttgtacaa caaccccgta    120

acagctgttt tcaactacca ggggctgtgg cgctcctgtg tccgagagag ctctggcttc    180

accgagtgcc ggggctactt caccctgctg gggctgccag ccatgctgca ggcagtgcga    240

gccctgatga tcgtaggcat cgtcctgggt gccattggcc tcctggtatc catctttgcc    300

ctgaaatgca tccgcattgg cagcatggag gactctgcca aagccaacat gacactgacc    360

tccgggatca tgttcattgt ctcaggtctt tgtgcaattg ctggagtgtc tgtgtttgcc    420

aacatgctgg tgactaactt ctggatgtcc acagctaaca tgtacaccgg catgggtggg    480

atggtgcaga ctgttcagac caggtacaca tttggtgcgg ctctgttcgt gggctgggtc    540

gctggaggcc tcacactaat tgggggtgtg atgatgtgca tcgcctgccg gggcctggca    600

ccagaagaaa ccaactacaa agccgtttct tatcatgcct cgggccacag tgttgcctac    660

aagcctggag gcttcaaggc cagcactggc tttgggtcca acaccaaaaa caagaagata    720

tacgatggag gtgcccgcac agaggacgag gtacaatctt atccttccaa gcacgactat    780

gtgtaa                                                                786
```

<210> SEQ ID NO 5
<211> LENGTH: 786
<212> TYPE: DNA
<213> ORGANISM: Artificial Sequence
<220> FEATURE:
<223> OTHER INFORMATION: Description of Artificial Sequence: artificially synthesized sequence

<400> SEQUENCE: 5

```
atgtccacca ccacatgcca agtggtggcg ttcctcctgt ccatcctggg gctggccggc     60

tgcatcgcgg ccaccgggat ggacatgtgg agcacccagg acctgtacga caaccccgtc    120

acctccgtgt tccagtacga agggctctgg aggagctgcg tgaggcagag ttcaggcttc    180

accgaatgca ggccctattt caccatcctg ggacttccag ccatgctgca ggcagtgcga    240

gccctgatga tcgtaggcat cgtcctgggt gccattggcc tcctggtatc catctttgcc    300

ctgaaatgca tccgcattgg cagcatggag gactctgcca aagccaacat gacactgacc    360

tccgggatca tgttcattgt ctcaggtctt tgtgcaattg ctggagtgtc tgtgtttgcc    420

aacatgctgg tgactaactt ctggatgtcc acagctaaca tgtacaccgg catgggtggg    480

atggtgcaga ctgttcagac caggtacaca tttggtgcgg ctctgttcgt gggctgggtc    540

gctggaggcc tcacactaat tgggggtgtg atgatgtgca tcgcctgccg gggcctggca    600

ccagaagaaa ccaactacaa agccgtttct tatcatgcct caggccacag tgttgcctac    660

aagcctggag gcttcaaggc cagcactggc tttgggtcca acaccaaaaa caagaagata    720

tacgatggag gtgcccgcac agaggacgag gtacaatctt atccttccaa gcacgactat    780

gtgtaa                                                                786
```

<210> SEQ ID NO 6
<211> LENGTH: 795
<212> TYPE: DNA
<213> ORGANISM: Artificial Sequence
<220> FEATURE:
<223> OTHER INFORMATION: Description of Artificial Sequence: artificially synthesized sequence

<400> SEQUENCE: 6

```
atgtcggtga ccgcctgcca gggcttgggg tttgtggtgt cactgatcgg gtttgcgggc     60

atcattgcag ccacttgtat ggaccagtgg agcacccagg atttatacaa caacccggtg    120

accgctgtat tcaactacca agggctatgg cgttcatgcg tccgagagag ctctggcttc    180

accgagtgcc gaggctactt caccctgttg ggttgccag ccatgctgca agctgtacga    240

gccctgatga tcgtgggcat tgttctgggg gtcatcggta tcctcgtgtc catcttcgcc    300

ctgaagtgca ttcgcattgg tagcatggat gactctgcca aggccaagat gactctgact    360

tctgggatct tgttcatcat ctccggcatc tgtgcaatca ttggtgtgtc tgtgtttgcc    420

aacatgctgg tgaccaactt ctggatgtcc acagctaaca tgtacagcgg catgggcggc    480

atgggtggca tggtgcagac cgttcagacc aggtacacct ttggtgcagc tctgttcgtg    540

ggctgggttg ctggaggcct caccctgatt gggggagtga tgatgtgcat cgcctgccgt    600

ggcctgacac cagatgacag caacttcaaa gctgtgtctt accatgcctc tggccaaaat    660

gttgcctaca ggcctggagg ctttaaggcc agcactggct ttgggtccaa caccagaaac    720

aagaagatct acgatggggg tgcccgcaca gaagacgatg aacagtctca tcctaccaag    780

tatgactatg tgtag                                                     795
```

<210> SEQ ID NO 7
<211> LENGTH: 795
<212> TYPE: DNA
<213> ORGANISM: Artificial Sequence
<220> FEATURE:
<223> OTHER INFORMATION: Description of Artificial Sequence:
      artificially synthesized sequence

<400> SEQUENCE: 7

```
atggccacca ccacgtgcca ggtggtaggg cttctcctgt ccctcctggg tctggccggc     60

tgcatagccg ccactgggat ggacatgtgg agcactcaag acctgtatga caacccagtc    120

accgccgtgt tccagtatga agggctctgg aggagttgcg tgcaacagag ctcggggttc    180

accgagtgcc ggccatactt caccatcctg ggccttccag ccatgctgca agctgtacga    240

gccctgatga tcgtgggcat tgttctgggg gtcatcggta tcctcgtgtc catcttcgcc    300

ctgaagtgca ttcgcattgg tagcatggat gactctgcca aggccaagat gactctgact    360

tctgggatct tgttcatcat ctccggcatc tgtgcaatca ttggtgtgtc tgtgtttgcc    420

aacatgctgg tgaccaactt ctggatgtcc acagctaaca tgtacagcgg catgggcggc    480

atgggtggca tggtgcagac cgttcagacc aggtacacct ttggtgcagc tctgttcgtg    540

ggctgggttg ctggaggcct caccctgatt gggggagtga tgatgtgcat cgcctgccgt    600

ggcctgacac cagatgacag caacttcaaa gctgtgtctt accatgcctc tggccaaaat    660

gttgcctaca ggcctggagg ctttaaggcc agcactggct ttgggtccaa caccagaaac    720

aagaagatct acgatggggg tgcccgcaca gaagacgatg aacagtctca tcctaccaag    780

tatgactatg tgtag                                                     795
```

<210> SEQ ID NO 8
<211> LENGTH: 1401
<212> TYPE: DNA
<213> ORGANISM: Artificial Sequence
<220> FEATURE:
<223> OTHER INFORMATION: Description of Artificial Sequence:
      artificially synthesized sequence

<400> SEQUENCE: 8

```
atggaatgga cctgggtctt tctcttcctc ctgtcagtaa ctgcaggtgt ccactcccag     60
```

gttcagctgc agcagtctgg agctgagctg atgaagcctg gggcctcagt gaagatatcc 120
tgcaaggcta ctggctacac attcagtagc tactggatag agtgggtaaa gcagaggcct 180
ggacatggcc ttgagtggat tggagagatt ttacctggaa gtggtagtac taactacaat 240
gagaagttca agggcaaggc cacattcact gcagatacat cctccaacac agcctacatg 300
caactcagca gcctgacatc tgaggactct gccgtctatt actgtgcaag atatgattac 360
ccctggtttg cttactgggg ccaagggact ctggtcactg tctctgcagc ctctacaaag 420
ggccccagcg tgtttccact ggctccctcc tctaagagca caagcggcgg caccgctgcc 480
ctgggctgtc tggtgaagga ctactttcca gagcctgtga cagtgagctg gaattccggc 540
gctctgacct ctggcgtgca cacctttcca gccgtgctgc agtcttccgg cctgtactcc 600
ctgtctagcg tggtgaccgt gcccagctcc tctctgggca cccagacata tatctgcaac 660
gtgaatcaca agccttccaa tacaaaggtg gacaagaagg tggagccaaa gtcctgtgac 720
aagacccata catgcccccc atgtcctgct cccgagctgc tgggcggccc ttccgtgttc 780
ctgtttcccc caaagcccaa ggataccctg atgatcagca gaaccccaga ggtgacatgc 840
gtggtggtgg acgtgtccca tgaggatccc gaggtgaagt tcaactggta cgtggacggc 900
gtggaggtgc ataacgccaa gacaaagcct agagaggagc agtacaactc cacctaccgg 960
gtggtgtccg tgctgaccgt gctgcaccag gactggctga atggcaagga gtacaagtgc 1020
aaggtgtcta ataaggccct gcctgctcca atcgagaaga caatctctaa ggctaagggc 1080
cagcctcggg agccccaggt gtataccctg cctccatcca gagacgagct gaccaagaat 1140
caggtgtctc tgacatgcct ggtgaagggc ttctatccat ccgatatcgc tgtggagtgg 1200
gagagcaatg gccagcctga gaacaattat aagacaaccc cacctgtgct ggattctgac 1260
ggcagctttt tcctgtattc caagctgacc gtggataagt ctagatggca gcagggcaac 1320
gtgttctcct gtagcgtgat gcacgaggca ctgcataatc actacaccca gaagtcactg 1380
tcactgagtc caggcaaata a 1401

<210> SEQ ID NO 9
<211> LENGTH: 708
<212> TYPE: DNA
<213> ORGANISM: Artificial Sequence
<220> FEATURE:
<223> OTHER INFORMATION: Description of Artificial Sequence:
artificially synthesized sequence

<400> SEQUENCE: 9
atgcattttc aagtgcagat tttcagcttc ctgctaatca gtgcctcagt cataatgtcc 60
agaggacaaa ttgttctcac ccagtctcca gcaatcatgt ctgcatctcc aggggagaag 120
gtcaccataa cctgcagtgc cagctcaagt gtaagttaca tgcactggtt ccagcagaag 180
ccaggcactt ctcccaaact ctggatttat agcacatcca acctggcttc tggagtccct 240
gctcgcttca gtggcagtgg atctgggacc tcttactctc tcacaatcag ccgaatggag 300
gctgaagatg ctgccactta ttactgccag caaaggagta gttacccacc cacgttcgga 360
ggggggacca agctggaaat aaagagaacc gtggctgccc caagcgtgtt tatcttccct 420
ccatctgatg agcagctgaa gtctggcaca gctagcgtgg tgtgcctgct gaataacttc 480
taccccagag aggccaaggt gcagtggaag gtggataacg ctctgcagtc tggcaactcc 540
caggagtctg tgacagagca ggattccaag gacagcacat actccctgtc tagcaccctg 600
acactgagca aggctgacta cgagaagcac aaggtgtacg cttgcgaggt cactcatcag 660

```
ggactgtcat ctcctgtcac taagagtttt aatcgcggcg agtgttga                708


<210> SEQ ID NO 10
<211> LENGTH: 1404
<212> TYPE: DNA
<213> ORGANISM: Artificial Sequence
<220> FEATURE:
<223> OTHER INFORMATION: Description of Artificial Sequence:
      artificially synthesized sequence

<400> SEQUENCE: 10

atgggatgga gctgtatcat cctcttcttg gtagcaacag ctacaggtgt ccactcccag     60

gtccaactgc agcagcctgg ggctgagctg gtgaggcctg gggcttcagt gaagctgtcc    120

tgcaaggctt ctggctacac cttcaccagc tactggataa actgggtgaa gcagaggcct    180

ggacaaggcc ttgagtggat cggaaatatt tatccttctg atagttatac taactacaat    240

caaaagttca aggacaaggc cacattgact gtagacaaat cctccagcac agcctacatg    300

cagctcagca gcccgacatc tgaggactct gcggtctatt actgtacaag atcgtggagg    360

ggtaactcct ttgactactg gggccaaggc accactctca cagtctcctc agcctctaca    420

aagggcccca gcgtgtttcc actggctccc tcctctaaga gcacaagcgg cggcaccgct    480

gccctgggct gtctggtgaa ggactacttt ccagagcctg tgacagtgag ctggaattcc    540

ggcgctctga cctctggcgt gcacaccttt ccagccgtgc tgcagtcttc cggcctgtac    600

tccctgtcta gcgtggtgac cgtgcccagc tcctctctgg gcacccagac atatatctgc    660

aacgtgaatc acaagccttc caatacaaag gtggacaaga aggtggagcc aaagtcctgt    720

gacaagaccc atacatgccc cccatgtcct gctcccgagc tgctgggcgg cccttccgtg    780

ttcctgtttc ccccaaagcc caaggatacc ctgatgatca gcagaacccc agaggtgaca    840

tgcgtggtgg tggacgtgtc ccatgaggat cccgaggtga agttcaactg gtacgtggac    900

ggcgtggagg tgcataacgc caagacaaag cctagagagg agcagtacaa ctccacctac    960

cgggtggtgt ccgtgctgac cgtgctgcac caggactggc tgaatggcaa ggagtacaag   1020

tgcaaggtgt ctaataaggc cctgcctgct ccaatcgaga agacaatctc taaggctaag   1080

ggccagcctc gggagcccca ggtgtatacc ctgcctccat ccagagacga gctgaccaag   1140

aatcaggtgt ctctgacatg cctggtgaag ggcttctatc catccgatat cgctgtggag   1200

tgggagagca atggccagcc tgagaacaat tataagacaa ccccacctgt gctggattct   1260

gacggcagct ttttcctgta ttccaagctg accgtggata agtctagatg gcagcagggc   1320

aacgtgttct cctgtagcgt gatgcacgag gcactgcata atcactacac ccagaagtca   1380

ctgtcactga gtccaggcaa ataa                                          1404


<210> SEQ ID NO 11
<211> LENGTH: 723
<212> TYPE: DNA
<213> ORGANISM: Artificial Sequence
<220> FEATURE:
<223> OTHER INFORMATION: Description of Artificial Sequence:
      artificially synthesized sequence

<400> SEQUENCE: 11

atggaatcac agactcaggt cctcatgtcc ctgctgttct gggtatctgg tacctgtggg     60

gacattgtga tgacacagtc tccatcctcc ctgactgtga cagcaggaga gaaggtcact    120

atgagctgca agtccagtca gagtctgtta aacagtggaa atcaaaagaa ctacttgacc    180
```

-continued

```
tggtaccagc agaaaccagg gcagcctcct aaactgttga tctactgggc atccactagg    240

gaatctgggg tccctgatcg cttcacaggc agtggatctg gaacagattt cactctcacc    300

atcagcagtg tgcaggctga agacctggca gtttattact gtcagaatga ttatagttat    360

ccattcacgt tcggctcggg gacaaagttg gaaataaaga gaaccgtggc tgccccaagc    420

gtgtttatct tccctccatc tgatgagcag ctgaagtctg gcacagctag cgtggtgtgc    480

ctgctgaata acttctaccc cagagaggcc aaggtgcagt ggaaggtgga taacgctctg    540

cagtctggca actcccagga gtctgtgaca gagcaggatt ccaaggacag cacatactcc    600

ctgtctagca ccctgacact gagcaaggct gactacgaga agcacaaggt gtacgcttgc    660

gaggtcactc atcagggact gtcatctcct gtcactaaga gttttaatcg cggcgagtgt    720

tga                                                                  723
```

<210> SEQ ID NO 12
<211> LENGTH: 1404
<212> TYPE: DNA
<213> ORGANISM: Artificial Sequence
<220> FEATURE:
<223> OTHER INFORMATION: Description of Artificial Sequence:
      artificially synthesized sequence

<400> SEQUENCE: 12

```
atggattggc tgtggaactt gctattcctg atggcagctg cccaaagtat ccaagcacag     60

atccagttgg tgcagtctgg acctgagctg aagaagcctg gagagacagt caagatctcc    120

tgcaaggctt ctgggtatac cttcacaaac tatggaatga actgggtgaa gcaggctcca    180

ggaaagggtt taaagtggat gggctggata aacaccaaca ctggagagcc aacatatgct    240

gaagagttca agggacggtt tgccttctct ttggaaacct ctgccagcac tgcctatttg    300

cagatcaaca acctcaaaaa tgaggacacg gctacatatt tctgtgcaag actgggtttt    360

ggtaatgcta tggactactg gggtcaagga acctcagtca ccgtctcctc agcctctaca    420

aagggcccca gcgtgtttcc actggctccc tcctctaaga gcacaagcgg cggcaccgct    480

gccctgggct gtctggtgaa ggactacttt ccagagcctg tgacagtgag ctggaattcc    540

ggcgctctga cctctggcgt gcacaccttt ccagccgtgc tgcagtcttc cggcctgtac    600

tccctgtcta gcgtggtgac cgtgcccagc tcctctctgg gcacccagac atatatctgc    660

aacgtgaatc acaagccttc caatacaaag gtggacaaga aggtggagcc aaagtcctgt    720

gacaagaccc atacatgccc cccatgtcct gctcccgagc tgctgggcgg cccttccgtg    780

ttcctgtttc ccccaaagcc caaggatacc ctgatgatca gcagaacccc agaggtgaca    840

tgcgtggtgg tggacgtgtc ccatgaggat cccgaggtga agttcaactg gtacgtggac    900

ggcgtggagg tgcataacgc caagacaaag cctagagagg agcagtacaa ctccacctac    960

cgggtggtgt ccgtgctgac cgtgctgcac caggactggc tgaatggcaa ggagtacaag   1020

tgcaaggtgt ctaataaggc cctgcctgct ccaatcgaga agacaatctc taaggctaag   1080

ggccagcctc gggagcccca ggtgtatacc ctgcctccat ccagagacga gctgaccaag   1140

aatcaggtgt ctctgacatg cctggtgaag ggcttctatc catccgatat cgctgtggag   1200

tgggagagca atggccagcc tgagaacaat tataagacaa ccccacctgt gctggattct   1260

gacggcagct ttttcctgta ttccaagctg accgtggata agtctagatg gcagcagggc   1320

aacgtgttct cctgtagcgt gatgcacgag gcactgcata atcactacac ccagaagtca   1380

ctgtcactga gtccaggcaa ataa                                          1404
```

<210> SEQ ID NO 13
<211> LENGTH: 723
<212> TYPE: DNA
<213> ORGANISM: Artificial Sequence
<220> FEATURE:
<223> OTHER INFORMATION: Description of Artificial Sequence:
artificially synthesized sequence

<400> SEQUENCE: 13
atggaatcac agactcaggt cctcatgtcc ctgctgttct gggtatctgg tacctgtggg 60
gacattgtga tgacacagtc tccatcctcc ctgactgtga cagcaggaga gaaggtcact 120
atgagctgca agtccagtca gagtctgtta aacagtggaa atcaaaagaa ctacttgacc 180
tggtaccagc agaaaccagg gcagcctcct aaactgttga tctactgggc atccactagg 240
gaatctgggg tccctgatcg cttcacaggc agtggatctg gaacagattt cactctcacc 300
atcagcagtg tgcaggctga agacctggca gtttattact gtcagaatga ttatagttat 360
ccgctcacgt tcggtgctgg gaccaagctg gagctgaaga gaaccgtggc tgccccaagc 420
gtgtttatct tccctccatc tgatgagcag ctgaagtctg gcacagctag cgtggtgtgc 480
ctgctgaata acttctaccc cagagaggcc aaggtgcagt ggaaggtgga taacgctctg 540
cagtctggca actcccagga gtctgtgaca gagcaggatt ccaaggacag cacatactcc 600
ctgtctagca ccctgacact gagcaaggct gactacgaga agcacaaggt gtacgcttgc 660
gaggtcactc atcagggact gtcatctcct gtcactaaga gttttaatcg cggcgagtgt 720
tga 723

<210> SEQ ID NO 14
<211> LENGTH: 351
<212> TYPE: DNA
<213> ORGANISM: Artificial Sequence
<220> FEATURE:
<223> OTHER INFORMATION: Description of Artificial Sequence:
artificially synthesized sequence

<400> SEQUENCE: 14
caggtacagc tgaaggagtc aggacctgtc ctggtggcgc cctcacagag cctgtccatc 60
acttgcactg tctctgggtt ttcattaacc acctatggtg tacagtgggt tcgccagcct 120
ccaggaaagg gtctggagtg gctgggagca atatgggctg gtggaaacac aaattataat 180
tcagctctca tgtccagact gagcatcagc aaagacaact ccaagagcca agttttctta 240
aaaatgaaca gtctgcaaac tgatgacaca gccatatact actgtgccaa agggggttac 300
gggaatgcta tggactactg gggtcaagga acctcagtca ccgtcgcctc a 351

<210> SEQ ID NO 15
<211> LENGTH: 354
<212> TYPE: DNA
<213> ORGANISM: Artificial Sequence
<220> FEATURE:
<223> OTHER INFORMATION: Description of Artificial Sequence:
artificially synthesized sequence

<400> SEQUENCE: 15
gagatccagc tgcagcagtc tggagctgag ctggtgaagc ctggggcttc agtgaagata 60
tcctgcaagg cttctggtta ttcattcact gactaccaca tgaactgggt gaggcagagc 120
catggaaaga gccttgagtg gattggaaat attgatcctt actatggtag tcctacctac 180
aatcataaat tcaagggcaa ggccacattg actgtagaca aatcttccag cacagcctac 240

-continued

```
atgcagctca tcagcctgac atctgaggac tctgcagtct attactgtgc aaactacgga    300

aggggaaatt cgtttcctta ctggggccaa gggactctgg tcactgtctc tgca          354


<210> SEQ ID NO 16
<211> LENGTH: 339
<212> TYPE: DNA
<213> ORGANISM: Artificial Sequence
<220> FEATURE:
<223> OTHER INFORMATION: Description of Artificial Sequence:
      artificially synthesized sequence

<400> SEQUENCE: 16

gacattgtga tgacacagtc tccatcctcc ctgactgtga cagcaggaga gagggtcact     60

atgagctgca agtccagtca gagtctgtta aacagtggaa atcaaaagaa ctacttgacc    120

tggtaccaac agaaatcagg gcagcctcct aaattgttga tctactgggc atccactagg    180

gaatctgggg tccctgatcg cttcacaggc agtggatctg gaacagattt cactctcacc    240

atcagcagtg tgcaggctga agacctggca gtttattact gtcagaatga ttattttttt    300

ccattcacgt tcggctcggg gacaaagttg gaaataaaa                           339


<210> SEQ ID NO 17
<211> LENGTH: 339
<212> TYPE: DNA
<213> ORGANISM: Artificial Sequence
<220> FEATURE:
<223> OTHER INFORMATION: Description of Artificial Sequence:
      artificially synthesized sequence

<400> SEQUENCE: 17

gacattgtga tgacacagtc tccatcctcc ctgactgtga cagcaggaga gaaggtcact     60

atgagctgca agtccagtca gagtctgtta aacagtggaa atcaaaggaa ctacttgacc    120

tggtaccagc agaaaccagg gcagcctcct aaactgttac tctactgggc atccactagg    180

gaatctgggg tccctgatcg cttcacaggc agtggatctg gaacagattt cactctcacc    240

atcagcagtg tgcaggctga agacctggca gtttattact gtcagaatga ttatagtttt    300

ccattcacgt tcggctcggg gacaaagttg gaaataaaa                           339


<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence:
      artificially synthesized sequence

<400> SEQUENCE: 18

Gly Phe Ser Leu Thr Thr Tyr
1               5


<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence:
      artificially synthesized sequence

<400> SEQUENCE: 19

Trp Ala Gly Gly Asn
1               5
```

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: artificially synthesized sequence

<400> SEQUENCE: 20

Gly Gly Tyr Gly Asn Ala Met Asp Tyr
1 5

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: artificially synthesized sequence

<400> SEQUENCE: 21

Gly Tyr Ser Phe Thr Asp Tyr
1 5

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence: artificially synthesized sequence

<400> SEQUENCE: 22

Asp Pro Tyr Tyr Gly Ser
1 5

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: artificially synthesized sequence

<400> SEQUENCE: 23

Tyr Gly Arg Gly Asn Ser Phe Pro Tyr
1 5

<210> SEQ ID NO 24
<211> LENGTH: 17
<212> TYPE: PRT
<213> ORGANISM: Artificial Sequence
<220> FEATURE:
<223> OTHER INFORMATION: Description of Artificial Sequence: artificially synthesized sequence

<400> SEQUENCE: 24

Lys Ser Ser Gln Ser Leu Leu Asn Ser Gly Asn Gln Lys Asn Tyr Leu
1 5 10 15

Thr

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: artificially synthesized sequence

<400> SEQUENCE: 25

Trp Ala Ser Thr Arg Glu Ser
1               5

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence:
      artificially synthesized sequence

<400> SEQUENCE: 26

Gln Asn Asp Tyr Phe Phe Pro Phe Thr
1               5

<210> SEQ ID NO 27
<211> LENGTH: 17
<212> TYPE: PRT
<213> ORGANISM: Artificial Sequence
<220> FEATURE:
<223> OTHER INFORMATION: Description of Artificial Sequence:
      artificially synthesized sequence

<400> SEQUENCE: 27

Lys Ser Ser Gln Ser Leu Leu Asn Ser Gly Asn Gln Arg Asn Tyr Leu
1               5                   10                  15

Thr

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence:
      artificially synthesized sequence

<400> SEQUENCE: 28

Trp Ala Ser Thr Arg Glu Ser
1               5

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence:
      artificially synthesized sequence

<400> SEQUENCE: 29

Gln Asn Asp Tyr Ser Phe Pro Phe Thr
1               5

<210> SEQ ID NO 30
<211> LENGTH: 117
<212> TYPE: PRT
<213> ORGANISM: Artificial Sequence
<220> FEATURE:
<223> OTHER INFORMATION: Description of Artificial Sequence:
      artificially synthesized sequence

<400> SEQUENCE: 30

Gln Val Gln Leu Lys Glu Ser Gly Pro Val Leu Val Ala Pro Ser Gln
1               5                   10                  15

Ser Leu Ser Ile Thr Cys Thr Val Ser Gly Phe Ser Leu Thr Thr Tyr

```
            20                  25                  30

Gly Val Gln Trp Val Arg Gln Pro Pro Gly Lys Gly Leu Glu Trp Leu
        35                  40                  45

Gly Ala Ile Trp Ala Gly Gly Asn Thr Asn Tyr Asn Ser Ala Leu Met
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Ile Tyr Tyr Cys Ala
                85                  90                  95

Lys Gly Gly Tyr Gly Asn Ala Met Asp Tyr Trp Gly Gln Gly Thr Ser
            100                 105                 110

Val Thr Val Ala Ser
        115


<210> SEQ ID NO 31
<211> LENGTH: 118
<212> TYPE: PRT
<213> ORGANISM: Artificial Sequence
<220> FEATURE:
<223> OTHER INFORMATION: Description of Artificial Sequence:
      artificially synthesized sequence

<400> SEQUENCE: 31

Glu Ile Gln Leu Gln Gln Ser Gly Ala Glu Leu Val Lys Pro Gly Ala
1               5                   10                  15

Ser Val Lys Ile Ser Cys Lys Ala Ser Gly Tyr Ser Phe Thr Asp Tyr
            20                  25                  30

His Met Asn Trp Val Arg Gln Ser His Gly Lys Ser Leu Glu Trp Ile
        35                  40                  45

Gly Asn Ile Asp Pro Tyr Tyr Gly Ser Pro Thr Tyr Asn His Lys Phe
    50                  55                  60

Lys Gly Lys Ala Thr Leu Thr Val Asp Lys Ser Ser Ser Thr Ala Tyr
65                  70                  75                  80

Met Gln Leu Ile Ser Leu Thr Ser Glu Asp Ser Ala Val Tyr Tyr Cys
                85                  90                  95

Ala Asn Tyr Gly Arg Gly Asn Ser Phe Pro Tyr Trp Gly Gln Gly Thr
            100                 105                 110

Leu Val Thr Val Ser Ala
        115


<210> SEQ ID NO 32
<211> LENGTH: 113
<212> TYPE: PRT
<213> ORGANISM: Artificial Sequence
<220> FEATURE:
<223> OTHER INFORMATION: Description of Artificial Sequence:
      artificially synthesized sequence

<400> SEQUENCE: 32

Asp Ile Val Met Thr Gln Ser Pro Ser Ser Leu Thr Val Thr Ala Gly
1               5                   10                  15

Glu Arg Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Ser Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
```

```
65                  70                  75                  80

Ile Ser Ser Val Gln Ala Glu Asp Leu Ala Val Tyr Tyr Cys Gln Asn
                85                  90                  95

Asp Tyr Phe Phe Pro Phe Thr Phe Gly Ser Gly Thr Lys Leu Glu Ile
            100                 105                 110

Lys


<210> SEQ ID NO 33
<211> LENGTH: 113
<212> TYPE: PRT
<213> ORGANISM: Artificial Sequence
<220> FEATURE:
<223> OTHER INFORMATION: Description of Artificial Sequence:
      artificially synthesized sequence

<400> SEQUENCE: 33

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Arg Asn Tyr Leu Thr Trp Tyr Gln Gln Lys Pro Gly Gln
        35                  40                  45

Pro Pro Lys Leu Leu Leu Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Phe Pro Phe Thr Phe Gly Ser Gly Thr Lys Leu Glu Ile
            100                 105                 110

Lys


<210> SEQ ID NO 34
<211> LENGTH: 117
<212> TYPE: PRT
<213> ORGANISM: Artificial Sequence
<220> FEATURE:
<223> OTHER INFORMATION: Description of Artificial Sequence:
      artificially synthesized sequence

<400> SEQUENCE: 34

Gln Val Gln Leu Lys Glu Ser Gly Pro Gly Leu Val Ala Pro Ser Glu
1               5                   10                  15

Thr Leu Ser Ile Thr Cys Thr Val Ser Gly Phe Ser Leu Thr Thr Tyr
            20                  25                  30

Gly Val Gln Trp Val Arg Gln Pro Pro Gly Lys Gly Leu Glu Trp Leu
        35                  40                  45

Gly Ala Ile Trp Ala Gly Gly Asn Thr Asn Tyr Asn Ser Ala Leu Met
    50                  55                  60

Ser Arg Leu Thr Ile Ser Lys Asp Asn Ser Lys Ser Gln Val Ser Leu
65                  70                  75                  80

Lys Met Ser Ser Val Thr Ala Ala Asp Thr Ala Ile Tyr Tyr Cys Ala
                85                  90                  95

Lys Gly Gly Tyr Gly Asn Ala Met Asp Tyr Trp Gly Gln Gly Thr Leu
            100                 105                 110

Val Thr Val Ser Ser
        115
```

<210> SEQ ID NO 35
<211> LENGTH: 113
<212> TYPE: PRT
<213> ORGANISM: Artificial Sequence
<220> FEATURE:
<223> OTHER INFORMATION: Description of Artificial Sequence:
artificially synthesized sequence

<400> SEQUENCE: 35

```
Asp Ile Val Met Thr Gln Ser Pro Ser Ser Leu Ala Val Ser Leu Gly
1               5                   10                  15

Glu Arg Ala Thr Met Asn Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Phe Phe Pro Phe Thr Phe Gly Gln Gly Thr Lys Leu Glu Ile
            100                 105                 110

Lys
```

<210> SEQ ID NO 36
<211> LENGTH: 117
<212> TYPE: PRT
<213> ORGANISM: Artificial Sequence
<220> FEATURE:
<223> OTHER INFORMATION: Description of Artificial Sequence:
artificially synthesized sequence

<400> SEQUENCE: 36

```
Gln Val Gln Leu Lys Glu Ser Gly Pro Gly Leu Val Ala Pro Ser Glu
1               5                   10                  15

Thr Leu Ser Ile Thr Cys Thr Val Ser Gly Phe Ser Leu Thr Thr Tyr
            20                  25                  30

Gly Val Gln Trp Val Arg Gln Pro Pro Gly Lys Gly Leu Glu Trp Leu
        35                  40                  45

Gly Ala Ile Trp Ala Gly Gly Asn Thr Asn Tyr Asn Ser Ala Leu Met
    50                  55                  60

Ser Arg Leu Thr Ile Ser Lys Asp Asn Ser Lys Ser Gln Val Ser Leu
65                  70                  75                  80

Lys Met Ser Ser Leu Thr Ala Ala Asp Thr Ala Ile Tyr Tyr Cys Ala
                85                  90                  95

Lys Gly Gly Tyr Gly Asn Ala Met Asp Tyr Trp Gly Gln Gly Thr Leu
            100                 105                 110

Val Thr Val Ser Ser
        115
```

<210> SEQ ID NO 37
<211> LENGTH: 113
<212> TYPE: PRT
<213> ORGANISM: Artificial Sequence
<220> FEATURE:
<223> OTHER INFORMATION: Description of Artificial Sequence:
artificially synthesized sequence

<400> SEQUENCE: 37

```
Asp Ile Val Met Thr Gln Ser Pro Ser Ser Leu Ala Val Ser Leu Gly
1               5                   10                  15

Glu Arg Val Thr Met Asn Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Phe Phe Pro Phe Thr Phe Gly Ser Gly Thr Lys Leu Glu Ile
            100                 105                 110

Lys


<210> SEQ ID NO 38
<211> LENGTH: 329
<212> TYPE: PRT
<213> ORGANISM: Artificial Sequence
<220> FEATURE:
<223> OTHER INFORMATION: Description of Artificial Sequence:
      artificially synthesized sequence

<400> SEQUENCE: 38

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240
```

```
Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325


<210> SEQ ID NO 39
<211> LENGTH: 107
<212> TYPE: PRT
<213> ORGANISM: Artificial Sequence
<220> FEATURE:
<223> OTHER INFORMATION: Description of Artificial Sequence:
      artificially synthesized sequence

<400> SEQUENCE: 39

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 40
<211> LENGTH: 118
<212> TYPE: PRT
<213> ORGANISM: Artificial Sequence
<220> FEATURE:
<223> OTHER INFORMATION: Description of Artificial Sequence:
      artificially synthesized sequence

<400> SEQUENCE: 40

Gln Ile Gln Leu Val Gln Ser Gly Ala Glu Val Lys Lys Pro Gly Ala
1               5                   10                  15

Ser Val Lys Ile Ser Cys Lys Ala Ser Gly Tyr Ser Phe Thr Asp Tyr
            20                  25                  30

His Met Asn Trp Val Arg Gln Ala Pro Gly Lys Gly Leu Glu Trp Ile
        35                  40                  45

Gly Asn Ile Asp Pro Tyr Tyr Gly Ser Pro Thr Tyr Asn His Lys Phe
    50                  55                  60

Lys Gly Arg Val Thr Leu Thr Val Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

```
Ala Asn Tyr Gly Arg Gly Asn Ser Phe Pro Tyr Trp Gly Gln Gly Thr
            100                 105                 110

Leu Val Thr Val Ser Ser
        115


<210> SEQ ID NO 41
<211> LENGTH: 113
<212> TYPE: PRT
<213> ORGANISM: Artificial Sequence
<220> FEATURE:
<223> OTHER INFORMATION: Description of Artificial Sequence:
      artificially synthesized sequence

<400> SEQUENCE: 41

Asp Ile Val Met Thr Gln Ser Pro Ser Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Arg Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Phe Pro Phe Thr Phe Gly Gln Gly Thr Lys Leu Glu Ile
            100                 105                 110

Lys


<210> SEQ ID NO 42
<211> LENGTH: 113
<212> TYPE: PRT
<213> ORGANISM: Artificial Sequence
<220> FEATURE:
<223> OTHER INFORMATION: Description of Artificial Sequence:
      artificially synthesized sequence

<400> SEQUENCE: 42

Asp Ile Val Met Thr Gln Ser Pro Ser Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Arg Asn Tyr Leu Thr Trp Tyr Gln Gln Lys Pro Gly Gln
        35                  40                  45

Pro Pro Lys Leu Leu Leu Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Leu Ala Val Tyr Tyr Cys Gln Asn
                85                  90                  95

Asp Tyr Ser Phe Pro Phe Thr Phe Gly Gln Gly Thr Lys Leu Glu Ile
            100                 105                 110

Lys


<210> SEQ ID NO 43
<211> LENGTH: 25
<212> TYPE: PRT
```

<213> ORGANISM: Artificial Sequence
<220> FEATURE:
<223> OTHER INFORMATION: Description of Artificial Sequence: artificially synthesized sequence

<400> SEQUENCE: 43

```
Gln Val Gln Leu Lys Glu Ser Gly Pro Val Leu Val Ala Pro Ser Gln
1               5                   10                  15

Ser Leu Ser Ile Thr Cys Thr Val Ser
            20                  25
```

<210> SEQ ID NO 44
<211> LENGTH: 19
<212> TYPE: PRT
<213> ORGANISM: Artificial Sequence
<220> FEATURE:
<223> OTHER INFORMATION: Description of Artificial Sequence: artificially synthesized sequence

<400> SEQUENCE: 44

```
Gly Val Gln Trp Val Arg Gln Pro Pro Gly Lys Gly Leu Glu Trp Leu
1               5                   10                  15

Gly Ala Ile
```

<210> SEQ ID NO 45
<211> LENGTH: 41
<212> TYPE: PRT
<213> ORGANISM: Artificial Sequence
<220> FEATURE:
<223> OTHER INFORMATION: Description of Artificial Sequence: artificially synthesized sequence

<400> SEQUENCE: 45

```
Thr Asn Tyr Asn Ser Ala Leu Met Ser Arg Leu Ser Ile Ser Lys Asp
1               5                   10                  15

Asn Ser Lys Ser Gln Val Phe Leu Lys Met Asn Ser Leu Gln Thr Asp
            20                  25                  30

Asp Thr Ala Ile Tyr Tyr Cys Ala Lys
        35                  40
```

<210> SEQ ID NO 46
<211> LENGTH: 11
<212> TYPE: PRT
<213> ORGANISM: Artificial Sequence
<220> FEATURE:
<223> OTHER INFORMATION: Description of Artificial Sequence: artificially synthesized sequence

<400> SEQUENCE: 46

```
Trp Gly Gln Gly Thr Ser Val Thr Val Ala Ser
1               5                   10
```

<210> SEQ ID NO 47
<211> LENGTH: 25
<212> TYPE: PRT
<213> ORGANISM: Artificial Sequence
<220> FEATURE:
<223> OTHER INFORMATION: Description of Artificial Sequence: artificially synthesized sequence

<400> SEQUENCE: 47

```
Glu Ile Gln Leu Gln Gln Ser Gly Ala Glu Leu Val Lys Pro Gly Ala
1               5                   10                  15

Ser Val Lys Ile Ser Cys Lys Ala Ser
            20                  25
```

```
<210> SEQ ID NO 48
<211> LENGTH: 19
<212> TYPE: PRT
<213> ORGANISM: Artificial Sequence
<220> FEATURE:
<223> OTHER INFORMATION: Description of Artificial Sequence:
      artificially synthesized sequence

<400> SEQUENCE: 48

His Met Asn Trp Val Arg Gln Ser His Gly Lys Ser Leu Glu Trp Ile
1               5                   10                  15

Gly Asn Ile


<210> SEQ ID NO 49
<211> LENGTH: 41
<212> TYPE: PRT
<213> ORGANISM: Artificial Sequence
<220> FEATURE:
<223> OTHER INFORMATION: Description of Artificial Sequence:
      artificially synthesized sequence

<400> SEQUENCE: 49

Pro Thr Tyr Asn His Lys Phe Lys Gly Lys Ala Thr Leu Thr Val Asp
1               5                   10                  15

Lys Ser Ser Ser Thr Ala Tyr Met Gln Leu Ile Ser Leu Thr Ser Glu
            20                  25                  30

Asp Ser Ala Val Tyr Tyr Cys Ala Asn
        35                  40


<210> SEQ ID NO 50
<211> LENGTH: 11
<212> TYPE: PRT
<213> ORGANISM: Artificial Sequence
<220> FEATURE:
<223> OTHER INFORMATION: Description of Artificial Sequence:
      artificially synthesized sequence

<400> SEQUENCE: 50

Trp Gly Gln Gly Thr Leu Val Thr Val Ser Ala
1               5                   10


<210> SEQ ID NO 51
<211> LENGTH: 23
<212> TYPE: PRT
<213> ORGANISM: Artificial Sequence
<220> FEATURE:
<223> OTHER INFORMATION: Description of Artificial Sequence:
      artificially synthesized sequence

<400> SEQUENCE: 51

Asp Ile Val Met Thr Gln Ser Pro Ser Ser Leu Thr Val Thr Ala Gly
1               5                   10                  15

Glu Arg Val Thr Met Ser Cys
            20


<210> SEQ ID NO 52
<211> LENGTH: 15
<212> TYPE: PRT
<213> ORGANISM: Artificial Sequence
<220> FEATURE:
<223> OTHER INFORMATION: Description of Artificial Sequence:
      artificially synthesized sequence

<400> SEQUENCE: 52
```

Trp Tyr Gln Gln Lys Ser Gly Gln Pro Pro Lys Leu Leu Ile Tyr
1 5 10 15

<210> SEQ ID NO 53
<211> LENGTH: 32
<212> TYPE: PRT
<213> ORGANISM: Artificial Sequence
<220> FEATURE:
<223> OTHER INFORMATION: Description of Artificial Sequence: artificially synthesized sequence

<400> SEQUENCE: 53

Gly Val Pro Asp Arg Phe Thr Gly Ser Gly Ser Gly Thr Asp Phe Thr
1 5 10 15

Leu Thr Ile Ser Ser Val Gln Ala Glu Asp Leu Ala Val Tyr Tyr Cys
20 25 30

<210> SEQ ID NO 54
<211> LENGTH: 10
<212> TYPE: PRT
<213> ORGANISM: Artificial Sequence
<220> FEATURE:
<223> OTHER INFORMATION: Description of Artificial Sequence: artificially synthesized sequence

<400> SEQUENCE: 54

Phe Gly Ser Gly Thr Lys Leu Glu Ile Lys
1 5 10

<210> SEQ ID NO 55
<211> LENGTH: 23
<212> TYPE: PRT
<213> ORGANISM: Artificial Sequence
<220> FEATURE:
<223> OTHER INFORMATION: Description of Artificial Sequence: artificially synthesized sequence

<400> SEQUENCE: 55

Asp Ile Val Met Thr Gln Ser Pro Ser Ser Leu Thr Val Thr Ala Gly
1 5 10 15

Glu Lys Val Thr Met Ser Cys
20

<210> SEQ ID NO 56
<211> LENGTH: 15
<212> TYPE: PRT
<213> ORGANISM: Artificial Sequence
<220> FEATURE:
<223> OTHER INFORMATION: Description of Artificial Sequence: artificially synthesized sequence

<400> SEQUENCE: 56

Trp Tyr Gln Gln Lys Pro Gly Gln Pro Pro Lys Leu Leu Leu Tyr
1 5 10 15

<210> SEQ ID NO 57
<211> LENGTH: 32
<212> TYPE: PRT
<213> ORGANISM: Artificial Sequence
<220> FEATURE:
<223> OTHER INFORMATION: Description of Artificial Sequence: artificially synthesized sequence

<400> SEQUENCE: 57

Gly Val Pro Asp Arg Phe Thr Gly Ser Gly Ser Gly Thr Asp Phe Thr
1 5 10 15

```
Leu Thr Ile Ser Ser Val Gln Ala Glu Asp Leu Ala Val Tyr Tyr Cys
            20                  25                  30


<210> SEQ ID NO 58
<211> LENGTH: 10
<212> TYPE: PRT
<213> ORGANISM: Artificial Sequence
<220> FEATURE:
<223> OTHER INFORMATION: Description of Artificial Sequence:
      artificially synthesized sequence

<400> SEQUENCE: 58

Phe Gly Ser Gly Thr Lys Leu Glu Ile Lys
1               5                   10


<210> SEQ ID NO 59
<211> LENGTH: 97
<212> TYPE: PRT
<213> ORGANISM: Artificial Sequence
<220> FEATURE:
<223> OTHER INFORMATION: Description of Artificial Sequence:
      artificially synthesized sequence

<400> SEQUENCE: 59

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Thr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg


<210> SEQ ID NO 60
<211> LENGTH: 98
<212> TYPE: PRT
<213> ORGANISM: Artificial Sequence
<220> FEATURE:
<223> OTHER INFORMATION: Description of Artificial Sequence:
      artificially synthesized sequence

<400> SEQUENCE: 60

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg
```

<210> SEQ ID NO 61
<211> LENGTH: 101
<212> TYPE: PRT
<213> ORGANISM: Artificial Sequence
<220> FEATURE:
<223> OTHER INFORMATION: Description of Artificial Sequence:
artificially synthesized sequence

<400> SEQUENCE: 61

Asp Ile Val Met Thr Gln Ser Pro Asp Ser Leu Ala Val Ser Leu Gly
1 5 10 15

Glu Arg Ala Thr Ile Asn Cys Lys Ser Ser Gln Ser Val Leu Tyr Ser
20 25 30

Ser Asn Asn Lys Asn Tyr Leu Ala Trp Tyr Gln Gln Lys Pro Gly Gln
35 40 45

Pro Pro Lys Leu Leu Ile Tyr Trp Ala Ser Thr Arg Glu Ser Gly Val
50 55 60

Pro Asp Arg Phe Ser Gly Ser Gly Ser Gly Thr Asp Phe Thr Leu Thr
65 70 75 80

Ile Ser Ser Leu Gln Ala Glu Asp Val Ala Val Tyr Tyr Cys Gln Gln
85 90 95

Tyr Tyr Ser Thr Pro
100

<210> SEQ ID NO 62
<211> LENGTH: 117
<212> TYPE: PRT
<213> ORGANISM: Artificial Sequence
<220> FEATURE:
<223> OTHER INFORMATION: Description of Artificial Sequence:
artificially synthesized sequence
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (16)..(17)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa can be any naturally occurring amino acid
<220> FEATURE:
<221> NAME/KEY: misc_feature
<222> LOCATION: (29)..(31)
<223> OTHER INFORMATION: Xaa can be any naturally occurring amino acid
<220> FEATURE:
<221> NAME/KEY: misc_feature
<222> LOCATION: (33)..(35)
<223> OTHER INFORMATION: Xaa can be any naturally occurring amino acid
<220> FEATURE:
<221> NAME/KEY: misc_feature
<222> LOCATION: (37)..(37)
<223> OTHER INFORMATION: Xaa can be any naturally occurring amino acid
<220> FEATURE:
<221> NAME/KEY: misc_feature
<222> LOCATION: (48)..(48)

<223> OTHER INFORMATION: Xaa can be any naturally occurring amino acid
<220> FEATURE:
<221> NAME/KEY: misc_feature
<222> LOCATION: (50)..(54)
<223> OTHER INFORMATION: Xaa can be any naturally occurring amino acid
<220> FEATURE:
<221> NAME/KEY: misc_feature
<222> LOCATION: (56)..(56)
<223> OTHER INFORMATION: Xaa can be any naturally occurring amino acid
<220> FEATURE:
<221> NAME/KEY: misc_feature
<222> LOCATION: (61)..(62)
<223> OTHER INFORMATION: Xaa can be any naturally occurring amino acid
<220> FEATURE:
<221> NAME/KEY: misc_feature
<222> LOCATION: (64)..(64)
<223> OTHER INFORMATION: Xaa can be any naturally occurring amino acid
<220> FEATURE:
<221> NAME/KEY: misc_feature
<222> LOCATION: (67)..(68)
<223> OTHER INFORMATION: Xaa can be any naturally occurring amino acid
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (73)..(73)
<223> OTHER INFORMATION: Xaa can be any naturally occurring amino acid
<220> FEATURE:
<221> NAME/KEY: misc_feature
<222> LOCATION: (76)..(76)
<223> OTHER INFORMATION: Xaa can be any naturally occurring amino acid
<220> FEATURE:
<221> NAME/KEY: misc_feature
<222> LOCATION: (78)..(79)
<223> OTHER INFORMATION: Xaa can be any naturally occurring amino acid
<220> FEATURE:
<221> NAME/KEY: misc_feature
<222> LOCATION: (82)..(83)
<223> OTHER INFORMATION: Xaa can be any naturally occurring amino acid
<220> FEATURE:
<221> NAME/KEY: misc_feature
<222> LOCATION: (85)..(88)
<223> OTHER INFORMATION: Xaa can be any naturally occurring amino acid
<220> FEATURE:
<221> NAME/KEY: misc_feature
<222> LOCATION: (92)..(92)
<223> OTHER INFORMATION: Xaa can be any naturally occurring amino acid
<220> FEATURE:
<221> NAME/KEY: misc_feature
<222> LOCATION: (97)..(117)
<223> OTHER INFORMATION: Xaa can be any naturally occurring amino acid

<400> SEQUENCE: 62

```
Gln Val Gln Leu Xaa Glu Ser Gly Pro Xaa Leu Val Xaa Pro Ser Xaa
1               5                   10                  15

Xaa Leu Ser Xaa Thr Cys Thr Val Ser Gly Xaa Ser Xaa Xaa Xaa Tyr
            20                  25                  30

Xaa Xaa Xaa Trp Xaa Arg Gln Pro Pro Gly Lys Gly Leu Glu Trp Xaa
        35                  40                  45

Gly Xaa Xaa Xaa Xaa Xaa Gly Xaa Thr Asn Tyr Asn Xaa Xaa Leu Xaa
    50                  55                  60

Ser Arg Xaa Xaa Ile Ser Xaa Asp Xaa Ser Lys Xaa Gln Xaa Xaa Leu
65                  70                  75                  80

Lys Xaa Xaa Ser Xaa Xaa Xaa Xaa Asp Thr Ala Xaa Tyr Tyr Cys Ala
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa
        115
```

<210> SEQ ID NO 63
<211> LENGTH: 113
<212> TYPE: PRT
<213> ORGANISM: Artificial Sequence
<220> FEATURE:
<223> OTHER INFORMATION: Description of Artificial Sequence: artificially synthesized sequence
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (14)..(15)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (21)..(22)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (40)..(40)
<223> OTHER INFORMATION: Xaa can be any naturally occurring amino acid
<220> FEATURE:
<221> NAME/KEY: misc_feature
<222> LOCATION: (46)..(46)
<223> OTHER INFORMATION: Xaa can be any naturally occurring amino acid
<220> FEATURE:
<221> NAME/KEY: misc_feature
<222> LOCATION: (69)..(69)
<223> OTHER INFORMATION: Xaa can be any naturally occurring amino acid
<220> FEATURE:
<221> NAME/KEY: misc_feature
<222> LOCATION: (84)..(84)
<223> OTHER INFORMATION: Xaa can be any naturally occurring amino acid
<220> FEATURE:
<221> NAME/KEY: misc_feature
<222> LOCATION: (89)..(89)
<223> OTHER INFORMATION: Xaa can be any naturally occurring amino acid
<220> FEATURE:
<221> NAME/KEY: misc_feature
<222> LOCATION: (96)..(97)
<223> OTHER INFORMATION: Xaa can be any naturally occurring amino acid
<220> FEATURE:
<221> NAME/KEY: misc_feature
<222> LOCATION: (99)..(100)
<223> OTHER INFORMATION: Xaa can be any naturally occurring amino acid
<220> FEATURE:
<221> NAME/KEY: misc_feature
<222> LOCATION: (102)..(113)
<223> OTHER INFORMATION: Xaa can be any naturally occurring amino acid

<400> SEQUENCE: 63

```
Asp Ile Val Met Thr Gln Ser Pro Xaa Ser Leu Xaa Val Xaa Xaa Gly
1               5                   10                  15

Glu Arg Xaa Thr Xaa Xaa Cys Lys Ser Ser Gln Ser Xaa Leu Xaa Ser
            20                  25                  30

Xaa Asn Xaa Lys Asn Tyr Leu Xaa Trp Tyr Gln Gln Lys Xaa Gly Gln
        35                  40                  45

Pro Pro Lys Leu Leu Ile Tyr Trp Ala Ser Thr Arg Glu Ser Gly Val
    50                  55                  60

Pro Asp Arg Phe Xaa Gly Ser Gly Ser Gly Thr Asp Phe Thr Leu Thr
65                  70                  75                  80

Ile Ser Ser Xaa Gln Ala Glu Asp Xaa Ala Val Tyr Tyr Cys Gln Xaa
                85                  90                  95

Xaa Tyr Xaa Xaa Pro Xaa Xaa Xaa Xaa Xaa Xaa Xaa Xaa Xaa Xaa Xaa
            100                 105                 110

Xaa
```

<210> SEQ ID NO 64
<211> LENGTH: 118
<212> TYPE: PRT
<213> ORGANISM: Artificial Sequence
<220> FEATURE:
<223> OTHER INFORMATION: Description of Artificial Sequence: artificially synthesized sequence
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (11)..(12)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (40)..(41)
<223> OTHER INFORMATION: Xaa can be any naturally occurring amino acid
<220> FEATURE:
<221> NAME/KEY: misc_feature
<222> LOCATION: (43)..(44)
<223> OTHER INFORMATION: Xaa can be any naturally occurring amino acid
<220> FEATURE:
<221> NAME/KEY: misc_feature
<222> LOCATION: (48)..(48)
<223> OTHER INFORMATION: Xaa can be any naturally occurring amino acid
<220> FEATURE:
<221> NAME/KEY: misc_feature
<222> LOCATION: (50)..(50)

<223> OTHER INFORMATION: Xaa can be any naturally occurring amino acid
<220> FEATURE:
<221> NAME/KEY: misc_feature
<222> LOCATION: (52)..(52)
<223> OTHER INFORMATION: Xaa can be any naturally occurring amino acid
<220> FEATURE:
<221> NAME/KEY: misc_feature
<222> LOCATION: (54)..(55)
<223> OTHER INFORMATION: Xaa can be any naturally occurring amino acid
<220> FEATURE:
<221> NAME/KEY: misc_feature
<222> LOCATION: (58)..(59)
<223> OTHER INFORMATION: Xaa can be any naturally occurring amino acid
<220> FEATURE:
<221> NAME/KEY: misc_feature
<222> LOCATION: (61)..(62)
<223> OTHER INFORMATION: Xaa can be any naturally occurring amino acid
<220> FEATURE:
<221> NAME/KEY: misc_feature
<222> LOCATION: (65)..(65)
<223> OTHER INFORMATION: Xaa can be any naturally occurring amino acid
<220> FEATURE:
<221> NAME/KEY: misc_feature
<222> LOCATION: (67)..(68)
<223> OTHER INFORMATION: Xaa can be any naturally occurring amino acid
<220> FEATURE:
<221> NAME/KEY: misc_feature
<222> LOCATION: (70)..(70)
<223> OTHER INFORMATION: Xaa can be any naturally occurring amino acid
<220> FEATURE:
<221> NAME/KEY: misc_feature
<222> LOCATION: (72)..(72)
<223> OTHER INFORMATION: Xaa can be any naturally occurring amino acid
<220> FEATURE:
<221> NAME/KEY: misc_feature
<222> LOCATION: (74)..(74)
<223> OTHER INFORMATION: Xaa can be any naturally occurring amino acid
<220> FEATURE:
<221> NAME/KEY: misc_feature
<222> LOCATION: (76)..(76)
<223> OTHER INFORMATION: Xaa can be any naturally occurring amino acid
<220> FEATURE:
<221> NAME/KEY: misc_feature
<222> LOCATION: (79)..(79)
<223> OTHER INFORMATION: Xaa can be any naturally occurring amino acid
<220> FEATURE:
<221> NAME/KEY: misc_feature
<222> LOCATION: (82)..(82)
<223> OTHER INFORMATION: Xaa can be any naturally occurring amino acid
<220> FEATURE:
<221> NAME/KEY: misc_feature
<222> LOCATION: (84)..(84)
<223> OTHER INFORMATION: Xaa can be any naturally occurring amino acid
<220> FEATURE:
<221> NAME/KEY: misc_feature
<222> LOCATION: (87)..(87)
<223> OTHER INFORMATION: Xaa can be any naturally occurring amino acid
<220> FEATURE:
<221> NAME/KEY: misc_feature
<222> LOCATION: (91)..(91)
<223> OTHER INFORMATION: Xaa can be any naturally occurring amino acid
<220> FEATURE:
<221> NAME/KEY: misc_feature
<222> LOCATION: (98)..(118)
<223> OTHER INFORMATION: Xaa can be any naturally occurring amino acid

<400> SEQUENCE: 64

```
Xaa Xaa Gln Leu Xaa Gln Ser Gly Ala Glu Xaa Xaa Lys Pro Gly Ala
1               5                   10                  15

Ser Val Lys Xaa Ser Cys Lys Ala Ser Gly Tyr Xaa Phe Thr Xaa Tyr
            20                  25                  30

Xaa Met Xaa Trp Val Arg Gln Xaa Xaa Gly Xaa Xaa Leu Glu Trp Xaa
        35                  40                  45

Gly Xaa Ile Xaa Pro Xaa Xaa Gly Ser Xaa Xaa Tyr Xaa Xaa Lys Phe
    50                  55                  60
```

```
Xaa Gly Xaa Xaa Thr Xaa Thr Xaa Asp Xaa Ser Xaa Ser Thr Xaa Tyr
65                  70                  75                  80

Met Xaa Leu Xaa Ser Leu Xaa Ser Glu Asp Xaa Ala Val Tyr Tyr Cys
                85                  90                  95

Ala Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa
        115


<210> SEQ ID NO 65
<211> LENGTH: 113
<212> TYPE: PRT
<213> ORGANISM: Artificial Sequence
<220> FEATURE:
<223> OTHER INFORMATION: Description of Artificial Sequence:
      artificially synthesized sequence
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (14)..(15)
<223> OTHER INFORMATION: Xaa can be any naturally occurring amino acid
<220> FEATURE:
<221> NAME/KEY: misc_feature
<222> LOCATION: (18)..(19)
<223> OTHER INFORMATION: Xaa can be any naturally occurring amino acid
<220> FEATURE:
<221> NAME/KEY: misc_feature
<222> LOCATION: (21)..(22)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: misc_feature
<222> LOCATION: (35)..(36)
<223> OTHER INFORMATION: Xaa can be any naturally occurring amino acid
<220> FEATURE:
<221> NAME/KEY: misc_feature
<222> LOCATION: (40)..(40)
<223> OTHER INFORMATION: Xaa can be any naturally occurring amino acid
<220> FEATURE:
<221> NAME/KEY: misc_feature
<222> LOCATION: (54)..(54)
<223> OTHER INFORMATION: Xaa can be any naturally occurring amino acid
<220> FEATURE:
<221> NAME/KEY: misc_feature
<222> LOCATION: (69)..(69)
<223> OTHER INFORMATION: Xaa can be any naturally occurring amino acid
<220> FEATURE:
<221> NAME/KEY: misc_feature
<222> LOCATION: (84)..(84)
<223> OTHER INFORMATION: Xaa can be any naturally occurring amino acid
<220> FEATURE:
<221> NAME/KEY: misc_feature
<222> LOCATION: (89)..(89)
<223> OTHER INFORMATION: Xaa can be any naturally occurring amino acid
<220> FEATURE:
<221> NAME/KEY: misc_feature
```

```
<222> LOCATION: (96)..(97)
<223> OTHER INFORMATION: Xaa can be any naturally occurring amino acid
<220> FEATURE:
<221> NAME/KEY: misc_feature
<222> LOCATION: (100)..(100)
<223> OTHER INFORMATION: Xaa can be any naturally occurring amino acid
<220> FEATURE:
<221> NAME/KEY: misc_feature
<222> LOCATION: (102)..(113)
<223> OTHER INFORMATION: Xaa can be any naturally occurring amino acid

<400> SEQUENCE: 65

Asp Ile Val Met Thr Gln Ser Pro Xaa Ser Leu Xaa Val Xaa Xaa Gly
1               5                   10                  15

Glu Xaa Xaa Thr Xaa Xaa Cys Lys Ser Ser Gln Ser Xaa Leu Xaa Ser
            20                  25                  30

Xaa Asn Xaa Xaa Asn Tyr Leu Xaa Trp Tyr Gln Gln Lys Pro Gly Gln
        35                  40                  45

Pro Pro Lys Leu Leu Xaa Tyr Trp Ala Ser Thr Arg Glu Ser Gly Val
    50                  55                  60

Pro Asp Arg Phe Xaa Gly Ser Gly Ser Gly Thr Asp Phe Thr Leu Thr
65                  70                  75                  80

Ile Ser Ser Xaa Gln Ala Glu Asp Xaa Ala Val Tyr Tyr Cys Gln Xaa
                85                  90                  95

Xaa Tyr Ser Xaa Pro Xaa Xaa Xaa Xaa Xaa Xaa Xaa Xaa Xaa Xaa Xaa
            100                 105                 110

Xaa
```